United States Patent
Chan et al.

(10) Patent No.: US 10,987,426 B2
(45) Date of Patent: Apr. 27, 2021

(54) COMPOSITIONS IN THE FORM OF AN INJECTABLE AQUEOUS SOLUTION COMPRISING HUMAN GLUCAGON AND A CO-POLYAMINO ACID

(71) Applicant: ADOCIA, Lyons (FR)

(72) Inventors: You-Ping Chan, Ternay (FR); Alexandre Geissler, Lyons (FR); Romain Noel, Villeurbanne (FR); Walter Roger, Lyons (FR); Richard Charvet, Rillieux la Pape (FR); Nicolas Laurent, Miribel (FR)

(73) Assignee: ADOCIA, Lyons (FR)

( * ) Notice: Subject to any disclaimer, the term of this patent is extended or adjusted under 35 U.S.C. 154(b) by 0 days.

(21) Appl. No.: 16/213,707

(22) Filed: Dec. 7, 2018

(65) Prior Publication Data

US 2019/0275156 A1 Sep. 12, 2019

Related U.S. Application Data

(60) Provisional application No. 62/606,137, filed on Dec. 7, 2017.

(30) Foreign Application Priority Data

Jun. 29, 2018 (EP) .................................... 18181023

(51) Int. Cl.
| | |
|---|---|
| *A61K 47/34* | (2017.01) |
| *A61K 9/00* | (2006.01) |
| *A61K 9/08* | (2006.01) |
| *A61K 38/26* | (2006.01) |
| *C08G 69/10* | (2006.01) |

(52) U.S. Cl.
CPC ............ *A61K 47/34* (2013.01); *A61K 9/0019* (2013.01); *A61K 9/08* (2013.01); *A61K 38/26* (2013.01); *C08G 69/10* (2013.01); *C07K 2319/30* (2013.01)

(58) Field of Classification Search
CPC ...... A61K 38/26; A61K 47/34; A61K 9/0019; A61K 9/08; C07K 2319/30; C08G 69/10
See application file for complete search history.

(56) References Cited

U.S. PATENT DOCUMENTS

| | | | |
|---|---|---|---|
| 6,384,016 B1 | 5/2002 | Kaarsholm | |
| 10,383,918 B2 | 8/2019 | Geissler et al. | |
| 10,485,851 B2 | 11/2019 | Geissler et al. | |
| 2011/0082080 A1 | 4/2011 | Levetan | |
| 2011/0097386 A1 | 4/2011 | Steiner et al. | |
| 2015/0291680 A1 | 10/2015 | Ward et al. | |

FOREIGN PATENT DOCUMENTS

| | | | |
|---|---|---|---|
| FR | 2 801 226 A1 | 5/2001 | |
| FR | 2 840 614 A1 | 12/2003 | |
| FR | 3 052 071 A1 | 12/2017 | |
| GB | 1 202 607 A | 8/1970 | |
| WO | 2011/138802 A1 | 11/2011 | |
| WO | 2012/059764 A1 | 5/2012 | |
| WO | 2013/101749 A1 | 7/2013 | |
| WO | 2013/104861 A1 | 7/2013 | |
| WO | 2014/096440 A2 | 6/2014 | |
| WO | 2015/095389 A1 | 6/2015 | |
| WO | 2017/211918 A1 | 12/2017 | |
| WO | 2017211917 A1 | 12/2017 | |

OTHER PUBLICATIONS

Apr. 10, 2019 Search Report issued in International Application No. PCT/EP2018/084066.
Apr. 3, 2019 Search Report issued in International Application No. PCT/EP2018/084064.
Apr. 10, 2019 Search Report issued in International Application No. PCT/EP2018/084065.
U.S. Appl. No. 16/213,836, filed Dec. 7, 2018 in the name of Chan et al.
U.S. Appl. No. 16/213,929, filed Dec. 7, 2018 in the name of Geissler et al.
Onoue et al.; "Mishandling of the Therapeutic Peptide Glucagon Generates Cytotoxic Amyloidogenic Fibrils;" Pharmaceutical Research; 2004; pp. 1271-1284; vol. 21, No. 7.
Kirsch et al.; "The degradation pathways of glucagon in acidic solutions;" International Journal of Pharmaceutics; 2000; pp. 115-125; vol. 203.
Jackson et al.; "Stable Liquid Glucagon Formulations for Rescue Treatment and Bi-Hormonal Closed-Loop Pancreas;" Curr. Diab. Rep.; 2012; pp. 705-710; vol. 12.
Matilainen et al.; "The Effect of Cyclodextrins on Chemical and Physical Stability of Glucagon and Characterization of Glucagon/γ-CD Inclusion Complexes;" Journal of Pharmaceutical Sciences; 2008; pp. 2720-2729; vol. 97, No. 7.
Matilainen et al.; "The stability and dissolution properties of solid glucagon/γ-cyclodextrin powder;" European Journal of Pharmaceutical Sciences; 2009; pp. 412-420; vol. 36.
Garay et al.; "Antibodies against polyethylene glycol in healthy subjects and in patients treated with PEG-conjugated agents;" Expert Opinion Drug Delivery; 2012; pp. 1319-1323; vol. 9.
Ganson et al.; "Pre-existing anti-polyethylene glycol antibody linked to first-exposure allergic reactions to pegnivacogin, a PEGylated RNA aptamer;" J Allergy Clin Immunol; 2016; pp. 1-11.

(Continued)

*Primary Examiner* — James H Alstrum-Acevedo
*Assistant Examiner* — Erinne R Dabkowski
(74) *Attorney, Agent, or Firm* — Oliff PLC

(57) ABSTRACT

Physically stable compositions in the form of an injectable aqueous solution, wherein the pH is from 6.0 to 8.0, includes at least:
   a) human glucagon and
   b) a co-polyamino acid bearing carboxylate charges and hydrophobic radicals Hy. In one embodiment, the compositions further comprise a gut hormone.

23 Claims, 1 Drawing Sheet

(56) References Cited

OTHER PUBLICATIONS

Tan et al.; "Coadministration of Glucagon-Like Peptide-1 During Glucagon Infusion in Humans Results in Increased Energy Expenditure and Amelioration of Hyperglycemia;" Diabetes; 2013; pp. 1131-1138; vol. 62.

Deming; "Polypeptide and Polypeptide Hybrid Copolymer Synthesis via NCA Polymerization;" Adv. Polym. Sci; 2006; pp. 1-18; vol. 202.

Deming; "Facile synthesis of block copolypeptides of defined architecture;" Nature; 1997; pp. 386-389; vol. 390.

Lu et al.; "Hexamethyldisilazane-Mediated Controlled Polymerization of a-Amino Acid N-Carboxyanhydrides;" J. Am. Chem. Soc.; 2007; pp. 14114-14115; vol. 129.

Lu et al.; "N-Trimethylsilyl Amines for Controlled Ring-Opening Polymerization of Amino Acid N-Carboxyanhydrides and Facile End Group Functionalization of Polypeptides;" J. Am. Chem. Soc.; 2008; pp. 12562-12563; vol. 130.

Naiki et al.; "Fluorometric Determination of Amyloid Fibrils in Vitro Using the Fluorescent Dye, Thioflavine T1;" Analytical Biochemistry; 1989; pp. 244-249; vol. 177.

Levine III.; "Quantification of β-Sheet Amyloid Fibril Structures with Thioflavin T;" Methods in Enzymology;1999; pp. 274-284; vol. 309.

Dec. 13, 2019 Office Action issued in U.S. Appl. No. 16/213,929.
Oct. 28, 2020 Office Action issued in U.S. Appl. No. 16/213,836.

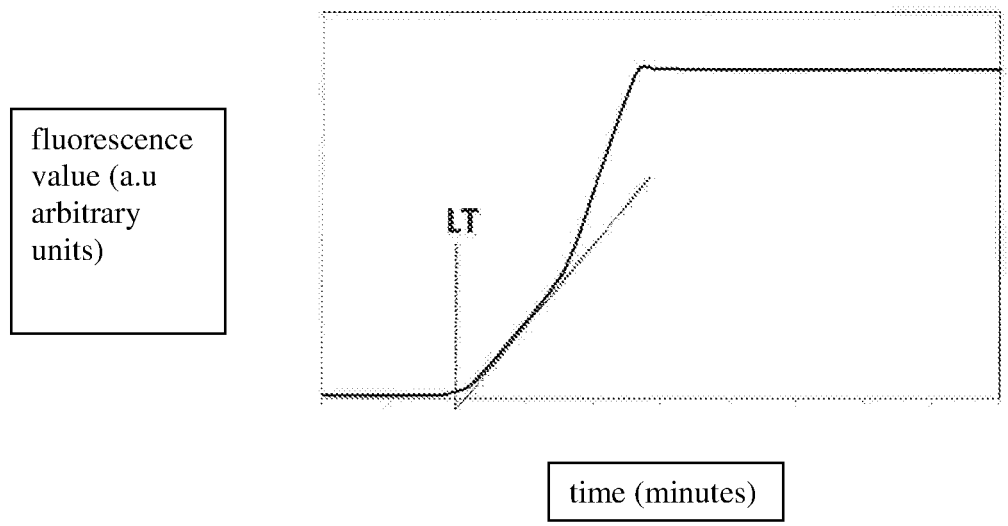

COMPOSITIONS IN THE FORM OF AN INJECTABLE AQUEOUS SOLUTION COMPRISING HUMAN GLUCAGON AND A CO-POLYAMINO ACID

Human glucagon is a short-acting hyperglycemic hormone that helps raise blood sugar, thus correcting a hypoglycemic level potentially resulting in excess insulin. It allows the release of glucose by stimulating glycogenolysis in the liver, and has insulin (hypoglycemic) antagonist properties. Human glucagon is normally secreted by alpha cells of the islets of Langerhans in the pancreas when hypoglycemia is detected.

Human glucagon is used for therapeutic purposes, such as the emergency, or "rescue", treatment of severe hypoglycemia, and also in a diagnostic context when conducting medical examinations, for example to inhibit gut motility. Further applications are also envisaged for human glucagon, in particular the use thereof in a bihormonal blood sugar regulation system also known as an artificial pancreas and in congenital hyperinsulinism which is a rare disease characterized by very elevated insulin levels.

The clinical use of human glucagon has been restricted due to some of the properties thereof that are unfavorable for developing a stable pharmaceutical product for therapeutic purposes. Indeed, human glucagon has a very low solubility at physiological pH, high physical instability, due to the tendency thereof to form fibrils over a wide pH range. For this reason, the only commercial products based on human glucagon (Glucagen®, NOVO NORDISK and Glucagon for injection, ELI LILLY) are freeze-dried forms for extemporaneous reconstitution.

The research by Onoue et al. (Pharm. Res. 2004, 21(7), 1274-83) demonstrated the potentially hazardous nature of these fibrils: fibrillated human glucagon being cytotoxic in mammalians cell in culture.

Besides the physical instability thereof, human glucagon is subject to various types of chemical degradation. In aqueous solution, it breaks down rapidly to form multiple degradation products. At least 16 degradation products of human glucagon have been identified by Kirsh et al. (International Journal of Pharmaceutics, 2000, 203, 115-125). The chemical degradation of this human glucagon is therefore rapid and complex.

The poor chemical and physical stability of human glucagon in solution has led pharmaceutical firms such as NOVO NORDISK, ELI LILLY and more recently FRESENIUS KABI to market this human glucagon in the form of a freeze-dried product to be reconstituted at acidic pH (pH<3) immediately prior to injection. Human glucagon in freeze-dried product form is more stable, and preparing the formulation at acidic pH immediately prior to use makes it possible to obtain a clear solution. However, once the product has been reconstituted, it must be used without delay as it is subject to extremely rapid chemical and physical degradation in the acidic reconstitution buffer, with the appearance of human glucagon fibrils within 24 hours following reconstitution, and/or gelling of the composition. This form of the product is however unsatisfactory as it requires very rapid use of the formulation. This instability not only renders use in a pump impossible, but it also has the drawback of giving rise to significant losses of product in diagnostic use. Indeed, as a composition of this type is only usable for a few hours after preparation, this causes waste.

Finally, even in the application of the rescue treatment of severe hypoglycemic reactions, liable to arise with insulin therapy in diabetic patients, the formulation to be reconstituted is not ideal either, as it involves time-consuming and complex preparation, for example the package insert of GlucaGeno describes a 5-stage process to inject the recommended dose. Moreover, a study by the company LOCEMIA demonstrates that very few subjects (about 10% of the participants) required to carry out emergency reconstitution were capable of dispensing the suitable dose. Finally, the acidic pH of human glucagon solutions may cause pain upon injection in the patient.

Therefore, there is a need for a ready-to-use human glucagon solution. At the present time, the most clinically advanced solutions for dispensing human glucagon overcome the problem in respect of the stability of human glucagon in various ways.

The company LOCEMIA has developed a freeze-dried human glucagon spray, currently being tested in phase 3 clinical trials, which is intended to be administered intranasally. This spray is suitable for so-called "rescue" use, namely in the case of severe hypoglycemia, as it is ready-to-use and therefore easy to use, unlike solutions to be reconstituted. However, this product is not suitable for use in a pump or use requiring accurate control of the quantity of human glucagon dispensed.

For its part, XERIS has developed a liquid human glucagon formulation based on a polar aprotic solvent, such as DMSO, currently tested in clinical trials. However, while the injection of solution of organic solvents for a "rescue" type use may be envisaged, it is largely preferable to have an aqueous solution of human glucagon for long-term use. Compositions comprising a combination with other peptides are envisaged particularly amylin or a GLP-1 RA (Glucagon like peptide-1 receptor agonist).

Finally, in view of the difficulties for formulating human glucagon, human glucagon analogs are under development by major pharmaceutical firms, such as NOVO NORDISK, SANOFI OR ELI LILLY, so as to obtain formulations having a stability compatible with pharmaceutical use. However, these peptides wherein the primary sequence has been modified with respect to the peptide of human origin may pose a safety risk for patients.

Therefore, there is major interest in a solution suitable for improving the solubilization and stability, both chemical and physical, of human glucagon in aqueous solution at a pH similar to physiological pH, namely from 6.0 to 8.0. This could make it possible to obtain a pharmaceutical product more readily usable by the patient in the event of an emergency, but also pave the way for new therapeutic applications of human glucagon, such as for example the use thereof in a bihormonal artificial pancreas.

The prior art proposes solutions to attempt to solve this problem.

Some documents propose applying a basic pH. For example, US2015291680 discloses the solubilization of 1 mg/ml human glucagon by placing it at a pH from 8.8 to 9.4 and using ferulic acid or tetrahydrocurcumin. However, besides being placed at a basic pH, this solution has the drawback of resulting in relatively limited stability of the human glucagon over time. The article by Jackson et al (Curr. Diab. Rep., 2012, 12, 705-710) proposes formulating human glucagon at a basic pH (about 10) so as to limit fibrils formation. However, this solution does not prevent rapid chemical degradation of the human glucagon.

The application WO2014096440 (NOVOZYME) envisages, on the other hand, using a slightly acidic pH (about 5.5) in the presence of albumin and polysorbate, so as to enhance the stability by lowering the fibrillation rate. However, this solution exhibits a limited improvement of stability. Most of the solutions described in the prior art suitable for obtaining a clear human glucagon solution and preventing the aggregation, gelling or precipitation of human glucagon involve the use of known surfactants, detergents or solubilizing agents.

For example, Matilainen et al (J. Pharm. Sci, 2008, 97, 2720-2729 and Eur. J. Pharm. Sci., 2009, 36, 412-420) described the use of cyclodextrin in order to limit the human glucagon fibril formation rate. However, the improvement provided appears insufficient to envisage a use in pumps.

The solutions proposed feature hydrophilic surfactants:
GB1202607 (NOVO NORDISK) describes the use of anionic or cationic detergents;
U.S. Pat. No. 6,384,016 (NOVO NORDISK) and US2011097386 (BIODEL) use lysophospholipids (or lysolecithins);
WO2015095389 (AEGIS) describes non-ionic surfactants, such as dodecyl maltoside, for enhancing the bioavailability of therapeutic agents, in the case of administration by mucosal or epidermal application, and in particular in the case of ocular, nasal, oral or nasolacrymal administration. This document describes that the presence of alkyl glycosides results in an improvement in the ocular uptake of human glucagon;
the application WO2012059764 (ARECOR) describes cationic surfactants, and more specifically aromatic ammonium chlorides.

The surfactants cited in the above documents may be too toxic or irritant for long-term subcutaneous use. For example, lysophospholipids (or lysolecithins) are known to lyse red blood cells due to the hemolytic properties thereof. Following a subcutaneous injection, this may induce local tissue damage and pain at the injection site. In the case of continuous injection by a pump, this may induce pain and/or irritation at the needle insertion site. The international application WO2011138802 (Sun Pharma) describes a ready-to-use human glucagon solution in micellar aqueous solution at a pH from 5 to 7.5 in the presence of a pegylated lipid (pegylated distearoyl-phosphotidylethanolamine). However, Garay et al. (Expert Opin Drug Deliv (2012) 9, 1319-1323) disclose that Poly Ethylene Glycol is both immunogenic and antigenic. This may be detrimental to patients presenting with anti-PEG antibodies. Moreover, Ganson et al. (J. Allergy Clin. Immunol. (2015) doi:10.1016/j.jaci.2015.10.034) describe that a clinical trial relating to pegnivacogin coupled with 40 kDa methoxypolyethylene glycol (mPEG) resulted in inflammatory responses from the first dose of pegnivacogin in 3 out of the 640 patients. Of these three patients, two met anaphylaxis criteria and one had an isolated dermal reaction, each event was deemed to be serious, and one was even deemed to be life-threatening. These adverse events caused the clinical trial to be discontinued and pose the problem of the adverse effects of pegylated compounds.

The document WO2013101749 (LATITUDE) describes nano-emulsions of human glucagon. However, it claims relatively modest performances in terms of chemical stability, namely that the composition comprises at least 75% of the initial concentration after 3-7 days at 37° C.

Furthermore, it should be noted that, to date, to the applicant's knowledge, no pharmaceutical formulation comprising human glucagon in aqueous solution form is being tested in clinical trials.

Therefore, there remains a need for a liquid aqueous formulation at a pH similar to physiological pH from 6.0 to 8.0 suitable for solubilizing and obtaining a satisfactory stability of human glucagon, both in terms of physical stability and chemical stability. More particularly, there is a need for such a formulation which can be used in a bihormonal pump (insulin/human glucagon).

This need is all the more clear as Tan et al. (Diabetes, 2013, 62, 1131-138) demonstrates that combining human glucagon with a GLP-1 RA is an attractive proposal for treating obesity and diabetes. However, being able to formulate human glucagon in a stable manner in aqueous solution at a pH similar to physiological pH from 6.0 to 8.0 makes it possible to set up more favorable conditions to be able to enhance the stability of GLP-1 RAs sensitive to acidic or basic conditions.

The co-polyamino acids bearing carboxylate charges and hydrophobic radicals Hy according to the invention exhibit an excellent resistance to hydrolysis. This may particularly be viewed under accelerated conditions, for example by hydrolysis tests at basic pH (pH 12).

Moreover, forced oxidation tests, for example of the Fenton oxidation type, demonstrate that the co-polyamino acids bearing carboxylate charges and hydrophobic radicals Hy exhibit a good resistance to oxidation.

The invention thus relates to physically stable compositions in the form of an injectable aqueous solution, wherein the pH is from 6.0 to 8.0, comprising at least:
a) human glucagon and
b) a co-polyamino acid bearing carboxylate charges and hydrophobic radicals Hy, said co-polyamino acid consisting of glutamic or aspartic units according to formula I, as defined hereinafter:

$$[Q(PLG)_k][Hy]_j[Hy]_{j'} \qquad \text{Formula I}$$ 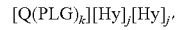

Wherein:
j≥1; 0≤j'≤n'1; j+j'≥1
k≥2
said co-polyamino acid according to formula I bearing at least one hydrophobic radical -Hy, carboxylate charges and consisting of at least two chains of glutamic or aspartic units PLG bound together by an at least divalent linear or branched radical or spacer $Q[-*]_k$ consisting of an alkyl chain comprising one or a plurality of heteroatoms chosen in the group consisting of nitrogen and oxygen atoms and/or bearing one or a plurality of heteroatoms consisting of nitrogen and oxygen radicals and/or radicals bearing one or a plurality of heteroatoms consisting of nitrogen and oxygen atoms and/or carboxyl functions,
said radical or spacer $Q[-*]_k$ being bound to at least two glutamic or aspartic unit chains PLG by an amide function and,
said amide functions binding said radical or spacer $Q[-*]_k$ bound to said at least two chains of glutamic or aspartic units result from the reaction between an amine function and an acid function respectively borne either by the precursor Q' of the radical or spacer $Q[-*]_k$ or by a glutamic or aspartic unit,
said hydrophobic radical -Hy being bound either to a terminal "amino acid" unit and then j≥1, or to a carboxyl function borne by one of the chains of the glutamic or aspartic units PLG and then j'=n'1 and n'1 is the mean number of monomeric glutamic or aspartic units bearing a hydrophobic radical -Hy.

In one embodiment, k is 2, 3, 4, 5 or 6.
In one embodiment, k=2.
In one embodiment, k=3.
In one embodiment, k=4.
In one embodiment, k=5.
In one embodiment, k=6.

In one embodiment, j is 1, 2, 3, 4, 5 or 6.
In one embodiment, j=1.
In one embodiment, j=2.
In one embodiment, j=3.
In one embodiment, j=4.
In one embodiment, j=5.
In one embodiment, j=6.

The invention further relates to a method for preparing stable injectable compositions.

The term "soluble" denotes suitable for enabling the preparation of a clear, particle-free solution at a concentration below 100 mg/ml in distilled water at 25° C.

The term "solution" denotes a liquid composition free from visible particles, using the procedure as per the pharmacopeias EP 8.0, section 2.9.20, and US <790>.

The term "physically stable composition" denotes compositions meeting, after a certain storage time at a certain temperature, the visual inspection criteria described in the European, US and international pharmacopeia, namely compositions which are clear and free from visible particles, but also colorless.

The term "chemically stable composition" denotes compositions which, after storing for a certain time and at a certain temperature, exhibit a minimum recovery of the active ingredients and meet the specifications applicable to pharmaceutical products.

A conventional method for measuring the stabilities of proteins or peptides consists of measuring the fibrils formation using Thioflavin T, also known as ThT. This method makes it possible to measure under temperature and stirring conditions enabling an acceleration of the phenomenon, the latent period prior to fibril formation by measuring the increase in fluorescence. The compositions according to the invention have a latent period prior to fibril formation markedly greater than that of glucagon at the pH of interest.

The term "injectable aqueous solution" denotes water-based solutions meeting EP and US pharmacopeia requirements, and which are sufficiently liquid to be injected.

The term "co-polyamino acid consisting of glutamic or aspartic units" denotes non-cyclic linear chains of glutamic acid or aspartic acid units bound together by peptide bonds, said chains having a C-terminal part, corresponding to the carboxylic acid of one extremity, and an N-terminal part, corresponding to the amine of the other extremity of the chain.

The term "alkyl radical" denotes a linear or branched carbon chain, which does not comprise a heteroatom.

Said co-polyamino acid is a statistical co-polyamino acid in the chain of glutamic and/or aspartic units.

In the formulas, the * indicate the binding sites of the different elements represented.

The compositions in the form of an injectable aqueous solution according to the invention are clear solutions. The term "clear solution" denotes compositions meeting the criteria described in the US and European pharmacopeias in respect of injectable solutions. In the US pharmacopeia, solutions are defined in part <1151> referring to injection <1> (referring to <788> as per USP 35 and specified in <788> as per USP 35 and in <787>, <788> and <790> USP 38 (from Aug. 1, 2014), as per USP 38). In the European pharmacopeia, injectable solutions must comply with the criteria provided in sections 2.9.19 and 2.9.20.

In one embodiment, the composition according to the invention is characterized in that Hy comprises from 15 to 100 carbon atoms.

In one embodiment, the composition according to the invention is characterized in that Hy comprises from 30 to 70 carbon atoms.

In one embodiment, the composition according to the invention is characterized in that Hy comprises from 40 to 60 carbon atoms.

In one embodiment, the composition according to the invention is characterized in that Hy comprises from 20 to 30 carbon atoms In one embodiment, Hy comprises more than 15 carbon atoms.

In one embodiment, Hy comprises more than 30 carbon atoms.

In one embodiment, the composition is characterized in that the pH is from 6.0 to 8.0.

In one embodiment, the composition is characterized in that the pH is from 6.6 to 7.8.

In one embodiment, the composition is characterized in that the pH is from 7.0 to 7.8.

In one embodiment, the composition is characterized in that the pH is from 6.8 to 7.4.

In one embodiment, the radical or spacer $Q[-*]_k$ is represented by a radical according to formula II:

$$Q[-*]_k = ([Q']_q)[-*]_k \qquad \text{Formula II}$$

wherein $1 \leq q \leq 5$ the radicals Q' being identical or different and chosen in the group consisting of radicals of the following formulas III to VI', to form $Q[-*]_k$:

by a radical according to formula III

Formula III

Wherein $1 \leq t \leq 8$ by a radical according to formula IV:

Formula IV wherein:
at least one of $u_1''$ or $u_2''$ is different to 0,
if $u_1'' \neq 0$ then $u_1' \neq 0$ and if $u_2'' \neq 0$ then $u_2' \neq 0$,
$u_1'$ and $u_2'$ are identical or different and,
$2 \leq u \leq 54$,
$0 \leq u_1' \leq 4$,
$0 \leq u_1'' \leq 4$,
$0 \leq u_2' \leq 4$
$0 \leq u_2'' \leq 4$,
by a radical according to formula V:

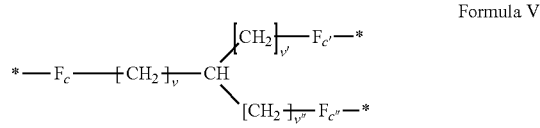

Formula V wherein:

v, v' and v" identical or different, are integers ≥0, and v+v'+v"≤15, by a radical according to formula VI:

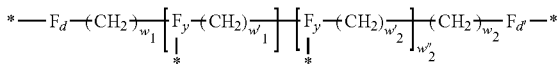

Formula VI wherein:

$w_1'$ is different to 0, $0 \leq w_2'' \leq 1$, $w_1 \leq 6$ and $w_1' \leq 6$ and/or $w_2 \leq 6$ and $w_2' \leq 6$ where Fd, and Fd' identical or different representing functions —NH— or —CO— and Fy representing a trivalent nitrogen atom —N=, two radicals Q' being bound together by a covalent bond between a carbonyl function, Fx=—CO—, and an amine function Fx=—NH— or Fy=—N=, thus forming an amide bond, a) where in each of the radicals represented above, Fx=Fa, Fb, Fc, Fd, Fa', Fb', Fc', Fc" and Fd' identical or different representing functions —NH— or —CO— and Fy representing a trivalent nitrogen atom —N=, b) two radicals Q' being bound together by a covalent bond between a carbonyl function, Fx=—CO—, and an amine function Fx=—NH— or Fy=—N=, thus forming an amide bond.

In one embodiment, said radical Q' is chosen among the radicals according to formula VI, wherein $w_2$=0 according to formula VI' as defined hereinafter:

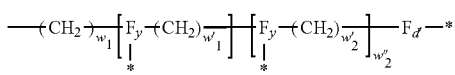

Formula VI' wherein:

$w_1'$ is different to 0, $0 \leq w_2'' \leq 1$, $w_1 \leq 6$ and $w_1' \leq 6$ and/or $w_2' \leq 6$ where Fd, and Fd' identical or different representing functions —NH— or —CO— and Fy representing a trivalent nitrogen atom —N=, two radicals Q' being bound together by a covalent bond between a carbonyl function, Fx=—CO—, and an amine function Fx=—NH— or Fy=—N=, thus forming an amide bond, a) where in each of the radicals represented above, Fx=Fa, Fb, Fc, Fd, Fa', Fb', Fc', Fc" and Fd' identical or different representing functions —NH— or —CO— and Fy representing a trivalent nitrogen atom —N=, b) two radicals Q' being bound together by a covalent bond between a carbonyl function, Fx=—CO—, and an amine function Fx=—NH— or Fy=—N=, thus forming an amide bond.

In one embodiment, if Fa and Fa' are —NH—, then t≥2.

In one embodiment, if Fa and Fa' are —CO—, then t≥1.

In one embodiment, if Fa and Fa' are —CO— and —NH—, then t≥1.

In one embodiment, if Fb and Fb' are —NH—, then u and $u_1' \geq 2$ and/or $u_2' \geq 2$.

In one embodiment, if Fc, Fc' and Fc" are —NH— then at least two of v, v' and v" are different to 0.

In one embodiment, if Fc, Fc' and Fc" are 2 —NH— and 1 —CO— then at least one of the indices of the —(CH₂)— bearing a nitrogen is different to 0.

In one embodiment, if Fc, Fc' and Fc" are 1 —NH— and 2 —CO— then no conditions.

In one embodiment, if Fc, Fc' and Fc" are —CO— then at least one of v, v' and v" is different to 0.

In one embodiment, if Fd and Fd' are —NH—, w1 and w1'≥2 and/or w2 and w'2≥2.

In one embodiment, if Fd and Fd' are —CO—, w1 and w1'≥1 and/or w2 and w2'≥1.

In one embodiment, if Fd and Fd' are —CO— and —NH—, w1 and w1'≥1 and/or w2 and w2'≥1.

The at least two chains of glutamic or aspartic units PLG being bound to $Q[-*]_k$ by a function Fx or Fy by a covalent bond to form an amide bond with a function —NH— or —CO— of the PLG.

In one embodiment, 1≤q≤5.

In one embodiment, v+v'+v"≤15.

In one embodiment, at least one of the Q' is a radical according to formula III,

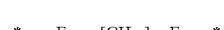

Formula III wherein the precursor is a diamine.

In one embodiment, the precursor of the radical according to formula III is a diamine chosen in the group consisting of ethylene diamine, butylenediamine, hexylenediamine, 1,3-diaminopropane and 1,5-diaminopentane, propylene diamine, pentylene diamine.

In one embodiment, t=2 and the precursor of the radical according to formula III is ethylene diamine.

In one embodiment, t=4 and the precursor of the radical according to formula III is butylenediamine.

In one embodiment, t=6 and the precursor of the radical according to formula III is hexylenediamine.

In one embodiment, t=3 and the precursor of the radical according to formula III is 1,3-diaminopropane.

In one embodiment, t=5 and the precursor of the radical according to formula III is 1,5-diaminopentane.

In one embodiment, the precursor of the radical according to formula III is an amino acid.

In one embodiment, the precursor of the radical according to formula III is an amino acid chosen in the group consisting of aminobutanoic acid, aminohexanoic acid and beta-alanine.

In one embodiment, t=2 and the precursor of the radical according to formula III is beta-alanine.

In one embodiment, t=6 and the precursor of the radical according to formula III is aminohexanoic acid.

In one embodiment, t=4 and the precursor of the radical according to formula III is aminobutanoic acid In one embodiment, the precursor of the radical according to formula III is a diacid.

In one embodiment, the precursor of the radical according to formula III is a diacid chosen in the group consisting of succinic acid, glutaric acid and adipic acid.

In one embodiment, t=2 and the precursor of the radical according to formula III is succinic acid.

In one embodiment, t=3 and the precursor of the radical according to formula III is glutaric acid.

In one embodiment, t=4 and the precursor of the radical according to formula III is adipic acid.

In one embodiment, at least one of the Q' is a radical according to formula IV,

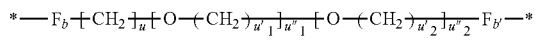

Formula IV wherein the precursor is a diamine.

In one embodiment, the precursor of the radical according to formula IV is a diamine chosen in the group consisting of diethyleneglycoldiamine, triethyleneglycol diamine, 1-amino-4,9-dioxa-12-dodecanamine and 1-amino-4,7,10-trioxa-13-tridecanamine.

In one embodiment, $u=u'_1=2$, $u''_1=1$, $u''_2=0$ and the precursor of the radical according to formula IV is diethyleneglycol diamine.

In one embodiment, $u=u'_1=u'_2=2$, $u''_1=u''_2=1$ and the precursor of the radical according to formula IV is triethyleneglycol diamine.

In one embodiment, $u=u'_2=3$, $u'_1=4$, $u''_1=u''_2=1$ and the precursor of the radical according to formula IV is 4,9-dioxa-1,12-dodecanediamine.

In one embodiment, $u=u'_2=3$, $u'_1=u''_1=2$, $u''_2=1$ and the precursor of the radical according to formula IV is 4,7,10-trioxa-1,13-tridecanediamine.

In one embodiment, at least one of the Q' is a radical according to formula V,

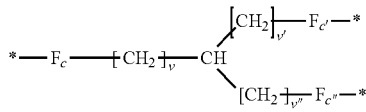

Formula V wherein the precursor is chosen in the group consisting of amino acids.

In one embodiment, the precursor of the radical according to formula V is an amino acid chosen in the group consisting of lysine, ornithine, 1,3-diaminopropionic acid.

In one embodiment, v=4, v'=v''=0 and the precursor of the radical according to formula V is lysine.

In one embodiment, v=3, v'=v''=0 and the precursor of the radical according to formula V is ornithine.

In one embodiment, v=2, v'=v''=0 and the precursor of the radical according to formula V is 2,3-diaminopropionic acid.

In one embodiment, at least one of the Q' is a radical according to formula V,

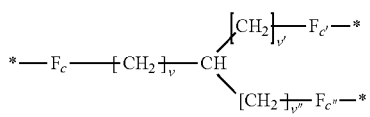

Formula V wherein the precursor is chosen in the group consisting of triacids.

In one embodiment, the precursor of the radical according to formula V is a triacid chosen in the group consisting of tricarballylic acid.

In one embodiment, v=0, v'=v''=1 and the precursor of the radical according to formula V is tricarballylic acid.

In one embodiment, the precursor of the radical according to formula V is a triacid chosen in the group consisting of tricarballylic acid.

In one embodiment, at least one of the Q' is a radical according to formula V,

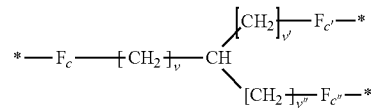

Formula V wherein the precursor is chosen in the group consisting of triamines.

In one embodiment, the precursor of the radical according to formula V is a triamine chosen in the group consisting of (2-(aminomethyl)propane-1,3-diamine).

In one embodiment, v=v'=v''=1 and the precursor of the radical according to formula V is (2-(aminomethyl)propane-1,3-diamine).

In one embodiment, at least one of the Q' is a radical according to formula VI,

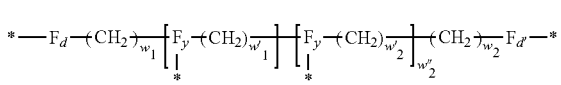

Formula VI wherein the precursor is a triamine.

In one embodiment, $w''_2=0$ and the precursor of the radical according to formula VI is a triamine chosen in the group consisting of spermidine, norspermidine, and diethylenetriamine and bis(hexamethylene)triamine.

In one embodiment, $w''_2=0$ and the precursor of the radical according to formula VI is spermidine.

In one embodiment, $w''_2=0$ and the precursor of the radical according to formula VI is norspermidine.

In one embodiment, $w''_2=0$ and the precursor of the radical according to formula VI is diethylenetriamine.

one embodiment, $w''_2=0$ and the precursor of the radical according to formula VI is bis(hexamethylene)triamine.

In one embodiment, $w''_2=1$ and the precursor of the radical according to formula VI is a tetramine.

In one embodiment, $w''_2=1$ and the precursor of the radical according to formula VI is a tetramine chosen in the group consisting of spermine and triethylenetetramine.

In one embodiment, $w''_2=1$ and the precursor of the radical according to formula VI is a tetramine chosen in the group consisting of spermine and triethylenetetramine.

In one embodiment, the precursor of the radical or spacer $Q[-*]_k$ has 4 reactive functions, chosen among the group of amine functions and carboxylic acid functions.

In one embodiment, the precursor of the radical or spacer $Q[-*]_k$ has 4 reactive functions and the precursor of the radical or spacer $Q[-*]_k$ is 1,2,3,4-butanetetraoic acid.

In one embodiment, at least one of the Q' is a radical according to formula VI',

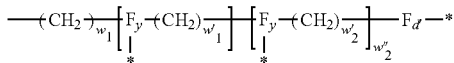
Formula VI' wherein the precursor is a triamine.

In one embodiment, w"$_2$=0 and the precursor of the radical according to formula VI' is a triamine chosen in the group consisting of spermidine, norspermidine, and diethylenetriamine and bis(hexamethylene)triamine.

In one embodiment, w"$_2$=0 and the precursor of the radical according to formula VI' is spermidine.

In one embodiment, w"$_2$=0 and the precursor of the radical according to formula VI' is norspermidine.

In one embodiment, w"$_2$=0 and the precursor of the radical according to formula VI' is diethylenetriamine.

In one embodiment, w"$_2$=0 and the precursor of the radical according to formula VI is bis(hexamethylene)triamine.

In one embodiment, at least one of the Q' is a radical according to formula VI',

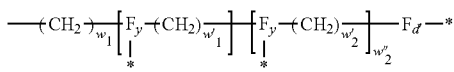
Formula VI' wherein the precursor is a tetramine.

In one embodiment, w"$_2$=1 and the precursor of the radical according to formula VI' is a tetramine.

In one embodiment, w"$_2$=1 and the precursor of the radical according to formula VI' is a tetramine chosen in the group consisting of spermine and triethylenetetramine.

In one embodiment, w"$_2$=1 and the precursor of the radical according to formula VI' is spermine.

In one embodiment, w'$_2$=1 and the precursor of the radical according to formula VI' is triethylenetetramine.

In one embodiment, the precursor of the radical or spacer Q[-*]$_k$ has 4 reactive functions, chosen among the amine and carboxylic acid functions.

In one embodiment, the precursor of the radical or spacer Q[-*]$_k$ has 4 reactive functions and the precursor of the radical or spacer Q[-*]$_k$ is 1,2,3,4-butanetetraoic acid.

In one embodiment, all the Fx are bound to the PLG or to other Fx or Fy.

In one embodiment, one or plurality of Fx are free, i.e. are not bound to the PLG, or to another Fx, or to an Fy.

In one embodiment, one Fx is free, i.e. is not bound to the PLG, or to another Fx, or to an Fy.

In one embodiment, the —CO— type Fx(s) is free, it is in carboxylic acid salt form.

In one embodiment, the free —CO— type Fx is borne by a radical Q' according to Formula V.

In one embodiment, the —NH— type Fx(s) is free, it is in amine or ammonium form.

In one embodiment, the PLG are bound to Fx where Fx=—NH— or to Fy by at least one carbonyl function of the PLG.

In one embodiment, the PLG are bound to Fx where Fx=—NH— or to Fy by at least one carbonyl function which is not in the C-terminal position of the PLG.

In one embodiment, the PLG are bound to Fx where Fx=—NH— or to Fy by the carbonyl function in the C-terminal function of the PLG.

In one embodiment, the PLG are bound to Fx where Fx=—NH— by the carbonyl function in the C-terminal function of the PLG.

In one embodiment, the PLG are bound to Fx where Fx=Fy by the carbonyl function in the C-terminal function of the PLG.

In one embodiment, the PLG are bound to Fx, where Fx=—CO— by the nitrogen atom in the N-terminal function of the PLG.

When the co-polyamino acid comprises one or a plurality of aspartic unit(s), the latter may to be subject to structural rearrangements.

In one embodiment, the composition according to the invention is characterized in that when the co-polyamino acids comprises aspartate units, then the co-polyamino acids may further comprise monomeric units according to formula XXXX and/or XXXX':

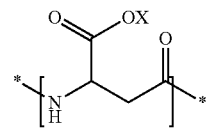
Formula XXXX

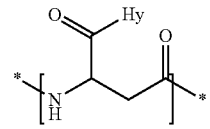
Formula XXXX'

The term "statistical grafting co-polyamino acid" denotes a co-polyamino acid bearing carboxylate charges and at least one hydrophobic radical, represented by a co-polyamino acid according to formula XXXa' and XXXb'.

The term "defined grafting co-polyamino acid" denotes a co-polyamino acid bearing carboxylate charges and at least one hydrophobic radical, represented by a co-polyamino acid according to formula, XXXa and XXXb.

In one embodiment, the composition according to the invention is characterized in that the co-polyamino acid bearing carboxylate charges and hydrophobic radicals is chosen among the co-polyamino acids according to formulas XXXa, XXXa', XXXb or XXXb' wherein the co-polyamino acid is chosen among the co-polyamino acids wherein the group D is a group —CH2- (aspartic unit).

In one embodiment, the composition according to the invention is characterized in that the co-polyamino acid bearing carboxylate charges and at least one hydrophobic radical -Hy is chosen among the co-polyamino acids according to formula XXXa hereinafter:

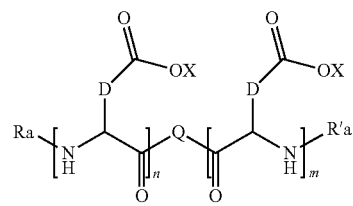
Formula XXXa wherein,

D represents, independently, either a group —CH$_2$— (aspartic acid) or a group —CH$_2$—CH$_2$— (glutamic acid), X represents a H or a cationic entity chosen in the group comprising metal cations, Ra and R'a, identical or different, are either a hydrophobic radical -Hy, or a radical chosen in the group consisting of a H, a C$_2$ to C$_{10}$ linear acyl group, a C$_3$ to C$_{10}$ branched acyl group, a benzyl, a terminal "amino acid" unit and a pyroglutamate, at least one of Ra and R'a being a hydrophobic radical -Hy, Q is as defined hereinafter -Hy is as defined above.

n+m is as defined above.

In one embodiment, the composition according to the invention is characterized in that the co-polyamino acid bearing carboxylate charges and at least one hydrophobic radical -Hy is chosen among the co-polyamino acids according to formula XXXa wherein R$_a$ and R'$_a$, identical, are a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXa wherein R$_a$ and R'$_a$, different, are hydrophobic radicals -Hy.

In one embodiment, the composition according to the invention is characterized in that the co-polyamino acid bearing carboxylate charges and at least one hydrophobic radical -Hy is chosen among the co-polyamino acids according to formula XXXa wherein R$_a$ is a hydrophobic radical -Hy and R'$_a$ is not a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXa wherein R'$_a$ is a hydrophobic radical -Hy, and R$_a$ is not a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXa' hereinafter:

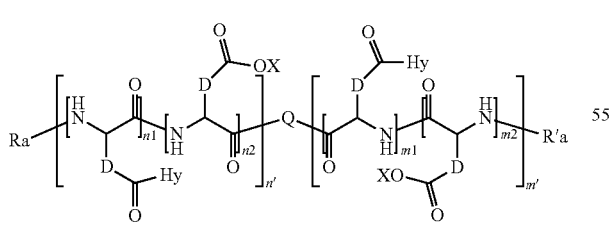

Formula XXXa'

Wherein:

D, X, Ra and R'a are as defined above,

Q and Hy are as defined above, n$_1$+m$_1$ represents the number of glutamic units or aspartic units of the PLG chains of the co-polyamino acid bearing a radical -Hy, n$_2$+m$_2$ represents the number of glutamic units or aspartic units of the PLG chains of the co-polyamino acid not bearing a radical -Hy, n$_1$+n$_2$=n' and m$_1$+m$_2$=m' n'+m' represents the degree of polymerization DP of the co-polyamino acid, namely the mean number of monomeric units per co-polyamino acid chain and 5≤n'+m'≤250.

In one embodiment, the composition according to the invention is characterized in that the co-polyamino acid bearing carboxylate charges and at least one hydrophobic radical -Hy is chosen among the co-polyamino acids according to formula XXXa' wherein Ra and R'a, identical, are a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXa' wherein Ra and R'a, different, are hydrophobic radicals -Hy.

In one embodiment, the composition according to the invention is characterized in that the co-polyamino acid bearing carboxylate charges and at least one hydrophobic radical -Hy is chosen among the co-polyamino acids according to formula XXXa' wherein Ra is a hydrophobic radical -Hy and R'a is not a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXa' wherein R'a is a hydrophobic radical -Hy, and Ra is not a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXb hereinafter:

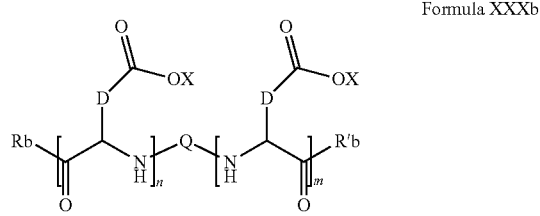

Formula XXXb wherein,

D and X are as defined above,

Rb and R'b, identical or different, are either a hydrophobic radical -Hy, or a radical chosen in the group consisting of an —OH, an amine group, a terminal "amino acid" unit and a pyroglutamate, at least one of Rb and R'b is a hydrophobic radical -Hy, Q and Hy are as defined above.

n+m is as defined above.

In one embodiment, the composition according to the invention is characterized in that the co-polyamino acid bearing carboxylate charges and at least one hydrophobic radical -Hy is chosen among the co-polyamino acids according to formula XXXb wherein Rb and R'b, identical, are a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXb wherein Rb and R'b, different, are hydrophobic radicals -Hy.

In one embodiment, the composition according to the invention is characterized in that the co-polyamino acid bearing carboxylate charges and at least one hydrophobic radical -Hy is chosen among the co-polyamino acids according to formula XXXb wherein Rb is a hydrophobic radical -Hy and R'b is not a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXb wherein R'b is a hydrophobic radical -Hy, and Rb is not a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXb' hereinafter:

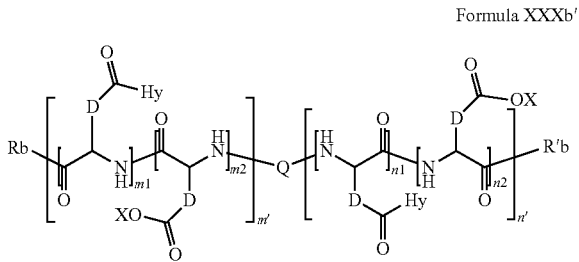

Formula XXXb' wherein:
D and X are as defined above,
Q and Hy are as defined above.
Rb and R'b, identical or different, are either a hydrophobic radical -Hy, or a radical chosen in the group consisting of an —OH, an amine group, a terminal "amino acid" unit and a pyroglutamate, at least one of Rb and R'b is a hydrophobic radical -Hy,
n1+m1 represents the number of glutamic units or aspartic units of the PLG chains of the co-polyamino acid bearing a radical -Hy,
n2+m2 represents the number of glutamic units or aspartic units of the PLG chains of the co-polyamino acid not bearing a radical -Hy,
n1+n2=n' and m1+m2=m',
n'+m' represents the degree of polymerization DP of the co-polyamino acid, namely the mean number of monomeric units per co-polyamino acid chain and $5 \leq n'+m' \leq 250$.

In one embodiment, the composition according to the invention is characterized in that the co-polyamino acid bearing carboxylate charges and at least one hydrophobic radical -Hy is chosen among the co-polyamino acids according to formula XXXb' wherein Rb and R'b, identical, are a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXb' wherein Rb and R'b, different, are hydrophobic radicals -Hy.

In one embodiment, the composition according to the invention is characterized in that the co-polyamino acid bearing carboxylate charges and at least one hydrophobic radical -Hy is chosen among the co-polyamino acids according to formula XXXb' wherein Rb is a hydrophobic radical -Hy and R'b is not a hydrophobic radical -Hy.

In one embodiment, the composition according to the invention is characterized in that the co-polyamino acid bearing carboxylate charges and at least one hydrophobic radical -Hy is chosen among the co-polyamino acids according to formula XXXb' wherein R'b is a hydrophobic radical -Hy, and Rb is not a hydrophobic radical -Hy.

In one embodiment, the co-polyamino acid is chosen among the co-polyamino acids according to formula XXXa, XXXa', XXXb, XXXb' wherein the hydrophobic radical -Hy is chosen in the group of hydrophobic radicals according to formula X wherein a'=1 and l'=1 and GpC is a radical according to formula IXe.

In one embodiment, the co-polyamino acid is chosen among the co-polyamino acids according to formula XXXa, XXXa', XXXb, XXXb' wherein the hydrophobic radical -Hy is chosen in the group of hydrophobic radicals according to formula X wherein a'=1 and l'=1 and GpC is a radical according to formula IX wherein e=0.

In one embodiment, the co-polyamino acid is chosen among the co-polyamino acids according to formula XXXa, XXXa', XXXb, XXXb' wherein the hydrophobic radical -Hy is chosen in the group of hydrophobic radicals according to formula X wherein a'=2 or l'=2 and GpC is a radical according to formula IXe.

In one embodiment, the co-polyamino acid is chosen among the co-polyamino acids according to formula XXXb wherein the hydrophobic radical -Hy is chosen in the group of hydrophobic radicals according to formula X wherein a'=2 or l'=2 and GpC is a radical according to formula IX wherein e=0.

In one embodiment, the composition according to the invention is characterized in that the co-polyamino acid bearing carboxylate charges and hydrophobic radicals is chosen among the co-polyamino acids according to formulas XXXa, XXXa', XXXb or XXXb' wherein the co-polyamino acid is chosen among the co-polyamino acids wherein the group D is a group —CH2- (aspartic unit).

In one embodiment, the composition according to the invention is characterized in that the co-polyamino acid bearing carboxylate charges and hydrophobic radicals is chosen among the co-polyamino acids according to formulas XXXa, XXXa', XXXb or XXXb' wherein the co-polyamino acid is chosen among the co-polyamino acids wherein the group D is a group —CH$_2$—CH$_2$— (glutamic unit).

In one embodiment, the composition according to the invention is characterized in that n+m is from 5 to 40.

In one embodiment, the composition according to the invention is characterized in that n+m is from 5 to 20.

In one embodiment, the composition according to the invention is characterized in that n+m is from 10 to 250.

In one embodiment, the composition according to the invention is characterized in that n+m is from 10 to 200.

In one embodiment, the composition according to the invention is characterized in that n+m is from 15 to 150.

In one embodiment, the composition according to the invention is characterized in that n+m is from 15 to 100.

In one embodiment, the composition according to the invention is characterized in that n+m is from 15 to 80.

In one embodiment, the composition according to the invention is characterized in that n+m is from 15 to 65.

In one embodiment, the composition according to the invention is characterized in that n+m is from 20 to 60.

In one embodiment, the composition according to the invention is characterized in that n+m is from 20 to 50.

In one embodiment, the composition according to the invention is characterized in that n+m is from 20 to 40.

In one embodiment, the composition is characterized in that said hydrophobic radicals -Hy are chosen among the radicals according to formula X as defined hereinafter.

In one embodiment said at least one hydrophobic radical -Hy is chosen among the radicals according to formula X as defined hereinafter:

Formula X

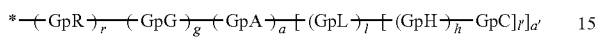

wherein
GpR is chosen among the radicals according to formulas VII, VII' or VII":

Formula VII

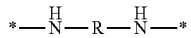

Formula VII'

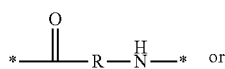

or

Formula VII"

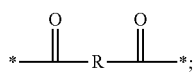

GpG and GpH identical or different are chosen among the radicals according to formulas XI or XI':

Formula XI

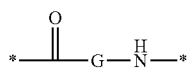

Formula XI'

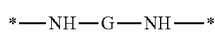

GpA is chosen among the radicals according to formula VIII

Formula VIII

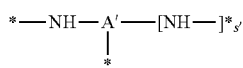

Wherein A' is chosen among the radicals according to VIII', VIII" or VIII'''

Formula VIII'

Formula VIII"

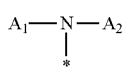

Formula VIII'''

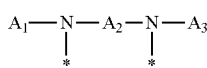

-GpL is chosen among the radicals according to formula XII

Formula XII

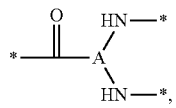

GpC is a radical according to formula IX:

Formula IX

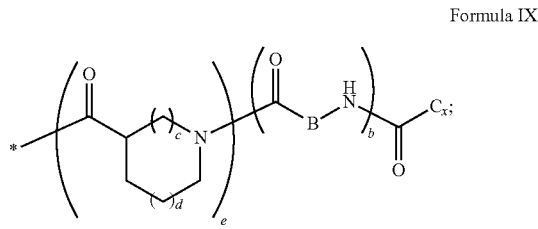

the * indicate the binding sites of the different groups bound by amide functions;

a is an integer equal to 0 or to 1 and a'=1 if a=0 and a'=1, 2 or 3 if a=1;

a' is an integer equal to 1, to 2 or to 3 b is an integer equal to 0 or to 1;

c is an integer equal to 0 or to 1, and if c is equal to 0 then d is equal to 1 or to 2;

d is an integer equal to 0, to 1 or to 2;

e is an integer equal to 0 or to 1;

g is an integer equal to 0, to 1, to 2, to 3 to 4 to 5 or to 6;

h is an integer equal to 0, to 1, to 2, to 3 to 4 to 5 or to 6;

l is an integer equal to 0 or 1 and l'=1 if l=0 and l'=2 if l=1;

l' is an integer equal to 1 or to 2;

r is an integer equal to 0, 1 or to 2, and s' is an integer equal to 0 or 1;

A, $A_1$, $A_2$ and $A_3$ identical or different are linear or branched alkyl radicals comprising from 1 to 8 carbon atoms and optionally substituted by a radical from a saturated, unsaturated or aromatic ring;

B is a radical chosen in the group consisting of a non-substituted ether or polyether radical comprising from 4 to 14 carbon atoms and from 1 to 5 oxygen atoms or a linear or branched alkyl radical, optionally comprising an aromatic ring, comprising from 1 to 9 carbon atoms;

$C_x$ is a radical chosen in the group consisting of a linear or branched monovalent alkyl radical, optionally comprising a cyclic part, wherein x indicates the number of carbon atoms and $6 \leq x \leq 25$:

When the hydrophobic radical -Hy bears 1 -GpC, then $9 \leq x \leq 25$,

When the hydrophobic radical -Hy bears 2 -GpC, then $9 \leq x \leq 15$,

When the hydrophobic radical -Hy bears 3 -GpC, then $7 \leq x \leq 13$,

When the hydrophobic radical -Hy bears 4 -GpC, then $7 \leq x \leq 11$,

When the hydrophobic radical -Hy bears at least 5 -GpC, then $6 \leq x \leq 11$, G is a linear or branched divalent alkyl radical comprising from 1 to 8 carbon atoms, said alkyl radical bearing one or a plurality of free carboxylic acid function(s).

R is a radical chosen in the group consisting of a linear or branched, divalent alkyl radical comprising from 1 to 12 carbon atoms, a linear or branched, divalent alkyl radical comprising from 1 to 12 carbon atoms bearing one or a plurality of functions —$CONH_2$ or a non-substituted ether or polyether radical comprising from 4 to 14 carbon atoms and from 1 to 5 oxygen atoms:

The hydrophobic radical(s) -Hy according to formula X being bound to the PLG:
  via a covalent bond between a carbonyl of the hydrophobic radical -Hy and a nitrogen atom borne by the PLG thus forming an amide function obtained from the reaction of an amine function borne by the PLG and an acid function borne by the precursor -Hy' of the hydrophobic radical -Hy, and
  via a covalent bond between a nitrogen atom of the hydrophobic radical -Hy and a carbonyl borne by the PLG thus forming an amide function obtained from the reaction of an amine function of the precursor -Hy' of the hydrophobic radical -Hy and an acid function borne by the PLG, the ratio M between the number of hydrophobic radicals and the number of glutamic or aspartic units being between $0 < M \leq 0.5$;

when a plurality of hydrophobic radicals are borne by a co-polyamino acid then they are identical or different, the degree of polymerization DP in glutamic or aspartic units for the PLG chains is from 5 to 250;

the free carboxylic acid functions being in the form of alkali cation salt chosen in the group consisting of $Na^+$ and $K^+$.

In one embodiment, when a'=1, x is from 11 to 25 ($11 \leq x \leq 25$). In particular, when x is from 15 to 16 (x=15 or 16) then r=1 and R is an ether or polyether radical and when x is greater than 17 ($x \geq 17$) then r=1 and R is an ether or polyether radical.

In one embodiment, when a'=2, x is from 9 to 15 ($9 \leq x \leq 15$).

In one embodiment, when r=2 then the group GpR bound to the PLG is chosen among the GpR according to formula VII.

In one embodiment, when r=2 then the group GpR bound to the PLG is chosen among the GpR according to formula VII and the second GpR is chosen among the GpR according to formula VII".

In one embodiment, when r=2 then the group GpR bound to the PLG is chosen among the GpR according to formula VII".

In one embodiment, when r=2 then the group GpR bound to the PLG is chosen among the GpR according to formula VII" and the second GpR is chosen among the GpR according to formula.

In one embodiment, said at least one hydrophobic radical -Hy is chosen among the radicals according to formula X wherein r=1 according to formula Xc, as defined hereinafter:

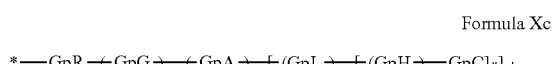

Formula Xc wherein GpR, GpG, GpA, GpL, GpH, GpC, R, a, a', g, h, l, a' and l' are as defined above.

In one embodiment, said at least one hydrophobic radical -Hy is chosen among the radicals according to formula X wherein r=1 according to formula Xc, as defined hereinafter:

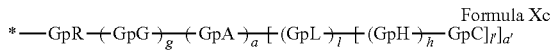

Formula Xc wherein GpR is a radical according to formula VII.

Formula VII wherein GpG, GpA, GpL, GpH, GpC, R, a, a', g, h, l and l' are as defined above.

In one embodiment, said at least one hydrophobic radical -Hy is chosen among the radicals according to formula Xc, as defined hereinafter:

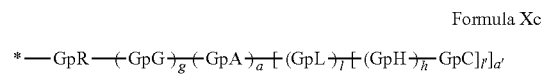

Formula Xc wherein GpR is a radical according to formula VII'.

Formula VII' wherein GpG, GpA, GpL, GpH, GpC, R, a, a', g, h, l and l' are as defined above.

In one embodiment, said at least one hydrophobic radical -Hy is chosen among the radicals according to formula Xc, as defined hereinafter:

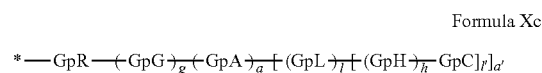

Formula Xc wherein GpR is a radical according to formula VII".

Formula VII"

wherein GpG, GpA, GpL, GpH, GpC, R, a, a', g, h, l and l' are as defined above.

In one embodiment, said at least one hydrophobic radical -Hy is chosen among the radicals according to formula X wherein r=2 according to formula Xc', as defined hereinafter:

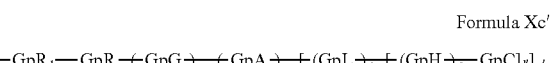

Formula Xc' wherein $GpR_1$ is a radical according to formula VII.

Formula VII

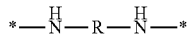

wherein GpR, GpG, GpA, GpL, GpH, GpC, R, a, a', g, h, l and l' are as defined above.

In one embodiment, said at least one hydrophobic radical -Hy is chosen among the radicals according to formula X wherein r=2 according to formula Xc', as defined hereinafter:

Formula Xc'

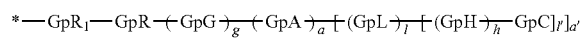

wherein $GpR_1$ is a radical according to formula VII".

Formula VII"

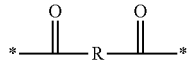

wherein GpR, GpG, GpA, GpL, GpH, GpC, R, a, a', g, h, l and l' are as defined above.

In one embodiment, said at least one hydrophobic radical -Hy is chosen among the radicals according to formula Xq as defined hereinafter:

Formula Xq

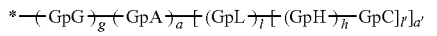

wherein GpG, GpA, GpL, GpH, GpC, g, a, a', l, h and l' are as defined above.

In one embodiment, said at least one hydrophobic radical -Hy is chosen among the radicals according to formula Xr as defined hereinafter:

Formula Xr

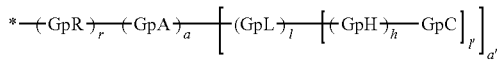

wherein GpR, GpA, GpL, GpH, GpC, r, a, a', l, h and l' are as defined above.

In one embodiment, the composition according to the invention is characterized in that said hydrophobic radicals are chosen among the hydrophobic radicals according to formula X wherein h=0 and g=0, represented by the formula Xj hereinafter:

Formula Xj

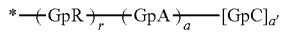

wherein GpR, GpA, GpC, r, a' and a are as defined above.

In one embodiment, the composition according to the invention is characterized in that said hydrophobic radicals are chosen among the hydrophobic radicals according to formula X wherein h=0 and g=0 and a'=1, represented by the formula Xk hereinafter:

Formula Xk

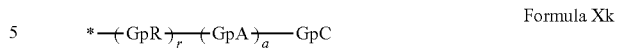

wherein GpR, GpA, GpC, r and a are as defined above.

In one embodiment, the composition according to the invention is characterized in that said hydrophobic radicals are chosen among the hydrophobic radicals according to formula X wherein h=0 and g=0 and a=1 and a'=2, represented by the formula Xl hereinafter:

Formula Xl

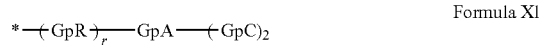

wherein GpR, GpA, GpC and r are as defined above.

In one embodiment, the composition according to the invention is characterized in that said hydrophobic radicals are chosen among the hydrophobic radicals according to formula X wherein a=1 and a'=1 and g=l=0, represented by the formula Xn hereinafter:

Formula Xn

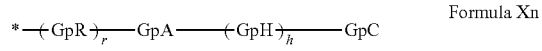

wherein GpR, GpA, GpH, GpC, r and h are as defined above.

In one embodiment, the composition according to the invention is characterized in that said hydrophobic radicals are chosen among the hydrophobic radicals according to formula X wherein a=1 and a'=2 and g=l=0, represented by the formula Xp hereinafter:

Formula Xp

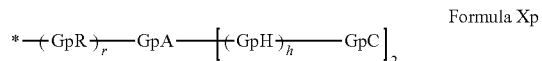

wherein GpR, GpA, GpH, GpC, r and h are as defined above.

In one embodiment, the composition according to the invention is characterized in that said hydrophobic radicals are chosen among the hydrophobic radicals according to formula X wherein a=1, g, h and l=0 and a'=3, represented by the formula Xm hereinafter:

Formula Xm

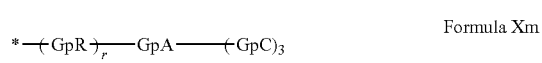

wherein GpA is a radical chosen among the radicals according to formula VIIId and GpR, GpC, r are as defined above.

In one embodiment, the composition according to the invention is characterized in that said hydrophobic radicals are chosen among the hydrophobic radicals according to formula X wherein a, g, h and l=0, represented by the formula Xm' hereinafter:

Formula Xm'

wherein GpR, GpC, r are as defined above.

In one embodiment, said at least one hydrophobic radical -Hy is chosen among the radicals according to formula X wherein r, g, a, l, h are equal to 0, according to formula Xo as defined hereinafter:

*-GpC      Formula Xo wherein GpC is as defined above.

In one embodiment, said at least one hydrophobic radical -Hy is chosen among the radicals according to formula X wherein r, g, a, l, h are equal to 0, according to formula Xo as defined hereinafter:

*-GpC      Formula Xo wherein GpC is a radical according to formula IX wherein e=0, b=0 and GpC is a radical according to formula IXc

IXc

In one embodiment, said at least one hydrophobic radical -Hy is chosen among the radicals according to formula Xs as defined hereinafter:

Formula Xs

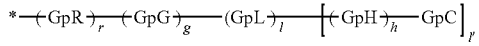

wherein GpR, GpG, GpL, GpH, GpC, r, g, l, h and l' are as defined above.

In one embodiment, said at least one hydrophobic radical -Hy is chosen among the radicals according to formula X wherein a=1 and a'=1 according to formula Xa as defined hereinafter:

Formula Xa

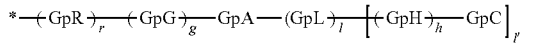

wherein GpA, GpR, GpG, GL, GpH, GpC, r, h, l and l' are as defined above.

In one embodiment, said at least one hydrophobic radical -Hy is chosen among the radicals according to formula X wherein a=1 and a'=1 according to formula Xa as defined hereinafter:

Formula Xa

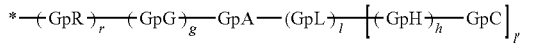

wherein GpA is a radical according to formula VIII and A' is chosen among the radicals according to formula VIII' where s'=0 and GpA is a radical according to formula VIIIb Formula VIIIb

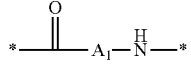

wherein GpR, GpG, GpL, GpH, GpC, r, g, h, l and l' are as defined above.

In one embodiment, said at least one hydrophobic radical -Hy is chosen among the radicals according to formula X wherein a=1 and a'=2 according to formula Xb as defined hereinafter:

Formula Xb

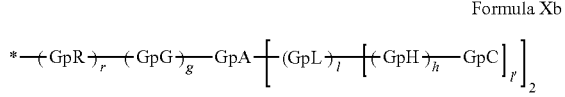

wherein GpA, GpR, GpG, GpL, GpH, GpC, r, g, h, l and l' are as defined above.

In one embodiment, said at least one hydrophobic radical -Hy is chosen among the radicals according to formula X wherein a=1 and a'=2 according to formula Xb as defined hereinafter:

Formula Xb

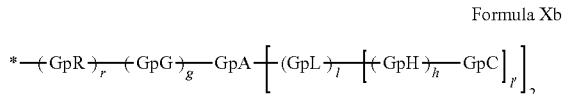

wherein GpA is a radical according to formula VIII and A' is chosen among the radicals according to formula VIII' where s'=1 and GpA is a radical according to formula VIIIa where a'=2

Formula VIIIa

wherein GpR, GpG, GpL, GpH, GpC, $A_1$, r, g, h, l and l' are as defined above.

In one embodiment, said at least one hydrophobic radical -Hy is chosen among the radicals according to formula X wherein a=1 and a'=2 as defined hereinafter:

Formula Xb

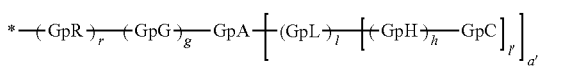

wherein GpA is a radical according to formula VIII and A is chosen among the radicals according to formula VIII" where s'=1 and GpA is a radical according to formula VIIIc Formula VIIIc

wherein GpR, GpG, GpL, GpH, GpC, $A_1$, $A_2$, r, g, h, l and l' are as defined above.

In one embodiment, said at least one hydrophobic radical -Hy is chosen among the radicals according to formula X wherein a=1 and a'=3 as defined hereinafter:

Formula Xb

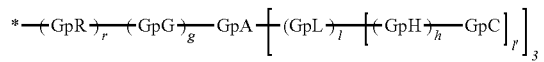

wherein GpA is a radical according to formula VIII and A is chosen among the radicals according to formula VIII''' where s'=1 and GpA is a radical according to formula VIIId Formula VIIId

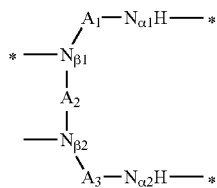

wherein GpR, GpG, GpL, GpH, GpC, $A_1$, $A_2$, $A_3$, r, g, h, l and l' are as defined above.

In one embodiment said at least one hydrophobic radical -Hy is chosen among the radicals according to formula X as defined above wherein l=0 according to formula Xd as defined hereinafter:

Formula Xd

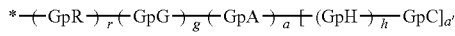

wherein GpR, GpG, GpA, GpH, GpC, r, g, a, h and a' are as defined above.

In one embodiment, said at least one hydrophobic radical -Hy is chosen among the radicals according to formula X wherein l=0, according to formula Xd as defined hereinafter Formula Xd

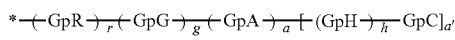

wherein

GpA is chosen among the radicals according to formula VIII wherein s'=1 represented by the formula VIIIa or according to formula VIII wherein s'=0 represented by the formula VIIIb:

Formula VIIIa

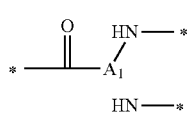

-continued

Formula VIIIb

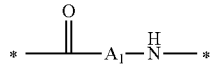

b, c, d, e, g, h, r, and s' are as defined above;
GpR, GpH, GpG GpC, $A_1$, B, Cx, G, H, R are as defined above;

In one embodiment said at least one hydrophobic radical -Hy is chosen among the radicals according to formula X as defined above wherein l=0 according to formula Xd as defined hereinafter:

Formula Xd

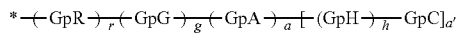

wherein

GpA is chosen among the radicals according to formula VIII wherein s'=1 represented by the formula VIIIc or the formula VIIId:

Formula VIIIc

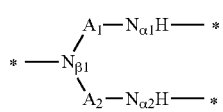

Formula VIIId

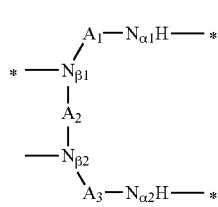

wherein GpR, GpG, GpH, GpC, $A_1$, $A_2$, $A_3$, r, g, a, h and a' are as defined above.

In one embodiment, the composition according to the invention is characterized in that said hydrophobic radicals are chosen among the hydrophobic radicals according to formula X wherein GpA is a radical according to formula VIIIb, a'=1 and l=0 represented by the formula Xe hereinafter:

Formula Xe

wherein GpR, GpG, GA, GpH, GpC, r, g, h, and a are as defined above.

In one embodiment, the composition according to the invention is characterized in that said hydrophobic radicals are chosen among the hydrophobic radicals according to formula X wherein a'=2 and a=1 and l=0 represented by the formula Xf hereinafter:

Formula Xf

wherein GpR, GpG, GpA, GpH, GpC, r, g and h are as defined above.

In one embodiment, the composition according to the invention is characterized in that said hydrophobic radicals are chosen among the hydrophobic radicals according to formula X wherein h=0, l=0 and l'=1 represented by the formula Xg hereinafter:

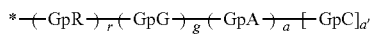

Formula Xg wherein GpR, GpG, GpA, GpC, r, g, a and a' are as defined above.

In one embodiment, the composition according to the invention is characterized in that said hydrophobic radicals are chosen among the hydrophobic radicals according to formula X wherein h=0, a'=1 represented by the formula Xh hereinafter:

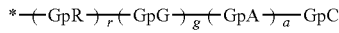

Formula Xh wherein GpR, GpG, GpA, GpC, r, a and g are as defined above.

In one embodiment, the composition according to the invention is characterized in that said hydrophobic radicals are chosen among the hydrophobic radicals according to formula X wherein h=0, a'=2 and a=1 represented by the formula Xi hereinafter:

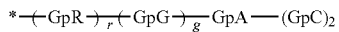

Formula Xi wherein GpR, GpG, GpA, GpC, r and g are as defined above.

In one embodiment said at least one hydrophobic radical -Hy is chosen among the radicals according to formula X as defined above wherein h=0 according to formula Xt as defined hereinafter:

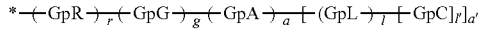

Formula Xt wherein GpR, GpG, GpA, GpL, GpC, r, g, a, l, l' and a' are as defined above.

In one embodiment said at least one hydrophobic radical -Hy is chosen among the radicals according to formula X as defined above wherein h and g=0 according to formula Xt' as defined hereinafter:

Formula Xt' wherein GpR, GpA, GpL, GpC and r are as defined above.

In one embodiment, the composition according to the invention is characterized in that said hydrophobic radicals are chosen among the hydrophobic radicals according to formula X wherein, l'=2 and a'=2 represented by the formula Xu hereinafter:

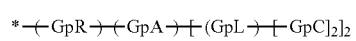

Formula Xu wherein GpR, GpA, GpL and GpC are as defined above.

In one embodiment, said at least one hydrophobic radical -Hy is chosen among the radicals according to formulas X, Xa to Xu:
  wherein at least one of g and/or h is greater than or equal to 1
  wherein GpC is a radical according to formula IX wherein e=0 and GpC is a radical according to formula IXa.

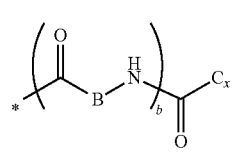

Formula IXa wherein B, b and Cx are as defined above.

In one embodiment, said at least one hydrophobic radical -Hy is chosen among the radicals according to formulas X, Xa to Xu wherein GpC is a radical according to formula IX wherein e=0 and GpC is a radical according to formula IXa,

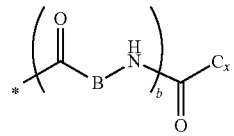

Formula IXa wherein B, b and Cx are as defined above.

In one embodiment, said at least one hydrophobic radical -Hy is chosen among the radicals according to formulas X, Xa to Xu wherein GpC is a radical according to formula IX wherein e=1, b=0 and GpC is a radical according to formula IXd.

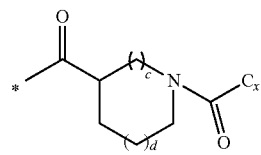

Formula IXd wherein c, d and Cx are as defined above.

In one embodiment, said at least one hydrophobic radical -Hy is chosen among the radicals according to formula X wherein GpC is a radical according to formula IX wherein e=0, b=0 and GpC is a radical according to formula IXc

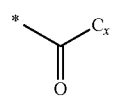

IXc wherein Cx is as defined above.

In one embodiment, said at least one hydrophobic radical -Hy is chosen among the radicals according to formulas X, Xa to Xu wherein GpC is a radical according to formula IX wherein e=1 and GpC is a radical according to formula IXb.

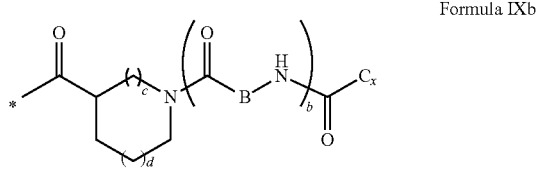

Formula IXb wherein c, d, B, b and Cx are as defined above.

In one embodiment, said at least one hydrophobic radical -Hy is chosen among the radicals according to formula X wherein
GpA is chosen among the radicals according to formula VIII wherein s'=1 represented by the formula VIIIa or according to formula VIII wherein s'=0 represented by the formula VIIIb:

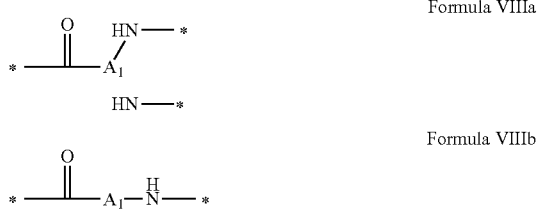

Formula VIIIa

Formula VIIIb wherein $A_1$ is as defined above.

In one embodiment, said at least one hydrophobic radical -Hy is chosen among the radicals according to formula X wherein
GpA is chosen among the radicals according to formula VIII wherein s'=1 represented by the formula VIIIc or the formula VIIId:

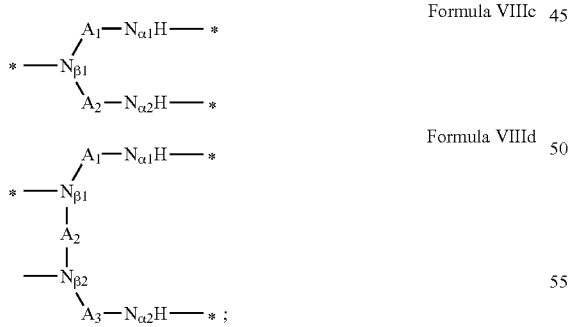

Formula VIIIc

Formula VIIId wherein $A_1$, $A_2$ and $A_3$ are as defined above.

In one embodiment, if GpA is a radical according to formula VIIIc and r=1, then:
the GpC are bound directly or indirectly to $N_{\square 1}$ and $N_{\square\square}$ and the PLG is bound directly or indirectly via -GpR to $N_{\square\square}$, or
the GpC are bound directly or indirectly to $N_{\square\square}$ and $N_{\square\square}$, and the PLG is bound directly or indirectly via GpR to $N_{\square\square}$; or
the GpC are bound directly or indirectly to $N_{\square\square}$ and $N_{\square\square}$, and the PLG is bound directly or indirectly via -GpR to $N_{\square\square}$.

In one embodiment, if GpA is a radical according to formula VIIIc and r=0, then:
the GpC are bound directly or indirectly to $N_{\square\square}$ and $N_{\square\square}$ and the PLG is bound directly or indirectly to $N_{\square\square}$; or
the GpC are bound directly or indirectly to $N_{\square\square}$ and $N_{\square\square}$, and the PLG is bound to directly or indirectly $N_{\square\square}$; or
the GpC are bound directly or indirectly to $N_{\square\square}$ and $N_{\square\square}$, and the PLG is bound directly or indirectly to $N_{\square\square}$.

In one embodiment, if GpA is a radical according to formula VIIId and r=1, then
the GpC are bound directly or indirectly to $N_{\square\square}$, $N_{\square\square}$ and $N_{\square\square}$ and the PLG is bound directly or indirectly via GpR to $N_{\square\square}$; or
the GpC are bound directly or indirectly to $N_{\square\square}$, $N_{\square\square}$ and $N_{\square\square}$ and the PLG is bound directly or indirectly via GpR to $N_{\square\square}$; or
the GpC are bound directly or indirectly to $N_{\square\square}$, $N_{\square\square}$ and $N_{\square\square}$ and the PLG is bound directly or indirectly via -GpR- to $N_{\square\square}$; or
the GpC are bound directly or indirectly to $N_{\square\square}$, $N_{\square\square}$ and $N_{\square\square}$ and the PLG is bound directly or indirectly via GpR to $N_{\square\square}\square$ In one embodiment, if GpA is a radical according to formula VIIId r=0, then
the GpC are bound directly or indirectly to $N_{\square\square}$, $N_{\square\square}$ and $N_{\square\square}$ and the PLG is bound directly or indirectly to $N_{\square\square}$; or
the GpC are bound directly or indirectly to $N_{\square\square}$, $N_{\square\square}$ and $N_{\square\square}$ and the PLG is bound directly or indirectly to $N_{\square\square}$; or
the GpC are bound directly or indirectly to $N_{\square\square}\square$ $N_{\square\square}$ and $N_{\square\square}$ and the PLG is bound directly or indirectly to $N_{\square\square}$; or
the GpC are bound directly or indirectly to $N_{\square\square}$, $N_{\square\square}$ and $N_{\square\square}$ and the PLG is bound directly or indirectly to $N_{\square\square}\square$ In one embodiment, a=0.
In one embodiment, h=1 and g=0.
In one embodiment, h=0 and g=1.
In one embodiment, r=0, g=1 and h=0.
In one embodiment, r=1 and GpR is chosen among the radicals according to formula VII' or VII" and h=0.
In one embodiment, r=1, g=0 and GpR is a radical according to formula VII' and h=0.
In one embodiment, r=1, g=0 and GpR is a radical according to formula VII' and h=1.
In one embodiment, r=1, g=0, GpR is a radical according to formula VII', GpA is chosen among the radicals according to formula VIIIa or VIIIb and h=0.
In one embodiment, r=1, g=0, GpR is a radical according formula VII', GpA is chosen among the radicals according to formula VIIIa or VIIIb and h=1.
In one embodiment, r=1, g=0, GpR is a radical according to formula VII', GpA is a radical according to formula VIIIa and h=0.
In one embodiment, r=1, g=0, GpR is a radical according to formula VII', GpA is a radical according to formula VIIIa and h=1.
In one embodiment, r=1, g=0, GpR is a radical according to formula VII', GpA is a radical according to formula VIIIb and h=0.

In one embodiment, r=1, g=0, GpR is a radical according to formula VII', GpA is a radical according to formula VIIIb and h=1.

In one embodiment, r=0, g=0 and GpA is chosen among the radicals according to formula VIIIa and VIIIb.

In one embodiment, r=0, g=0, GpA is chosen among the radicals according to formula VIIIa and VIIIb and h=0.

In one embodiment, g+h≥2.

In one embodiment, g is greater than or equal to 2 (g≥2).

In one embodiment, h is greater than or equal to 2 (h≥2).

In one embodiment, g+h≥2 and a and l are equal to 0 (a=l=0).

In one embodiment, g+h≥2 and b is equal to 0 (b=0).

In one embodiment, g or h is greater than or equal to 2 (g≥2) and b is equal to 0.

In one embodiment, g+h≥2, b is equal to 0 (b=0) and e is equal to 1 (e=1).

In one embodiment, g or h is greater than or equal to 2 (g≥2), b is equal to 0 (b=0) and e is equal to 1 (e=1).

In the formulas, the * indicate the binding sites of the hydrophobic radicals to the PLG or between the different groups GpR, GpG, GpA, GpL, GpH and GpC to form amide functions.

The radicals -Hy are bound to the PLG via amide functions.

In the formulas VII, VII' and VII", the * indicate, from left to right respectively, the binding sites of GpR:
to the PLG and
to GpG if g≥1 or to GpA if g=0 or to GpL if l=1 and g=a=0 or to GpH if h≥1 and g=a=l=0 or GpC if a'=1 and g=a=l=h=0.

In the formulas VIIIa, VIIIb, VIIIc and VIIId, the * indicate, from left to right respectively, the binding sites of GpA:
to GpG if g≥1 or to GpR if r=1 or 2 and g=0 or to the PLG if g=r=0 and
to GpL if l=1 or to GpH if h≥1 and l=0 or to GpC if l=h=0

In the formula IX, the * indicates the binding site of GpC:
to GpH if h≥1,
to GpL if l=1 and h=0
to GpA if a=1 and h=l=0
to GpG if g≥1 and h=l=a=0
to GpR if r=1 or 2 and h=l=a=g=0
to the PLG if h=l=a=g=r=0

The radicals -Hy, GpR, GpG, GpA, GpL, GpH and GpC are each independently identical or different from one residue to another.

In one embodiment, a=0,
In one embodiment, h=1 and g=0,
In one embodiment, h=0 and g=1,
In one embodiment, r=0, g=1 and h=0.

The radicals Hy, GpR, GpG, GpA, GpL, GpH and GpC are each independently identical or different from one residue to another.

In one embodiment, the composition is characterized in that the hydrophobic radical according to formula X is a radical wherein R is a divalent linear alkyl radical comprising from 2 to 12 carbon atoms.

In one embodiment, the composition is characterized in that the hydrophobic radical according to formula X is a radical wherein R is a divalent alkyl radical comprising from 2 to 6 carbon atoms.

In one embodiment, the composition is characterized in that the hydrophobic radical according to formula X is a radical wherein R is a divalent linear alkyl radical comprising from 2 to 6 carbon atoms.

In one embodiment, the composition is characterized in that the hydrophobic radical according to formula X is a radical wherein R is a divalent alkyl radical comprising from 2 to 4 carbon atoms.

In one embodiment, the composition is characterized in that the hydrophobic radical according to formula X is a radical wherein R is a divalent linear alkyl radical comprising from 2 to 4 carbon atoms.

In one embodiment, the composition is characterized in that the hydrophobic radical according to formula X is a radical wherein R is a divalent alkyl radical comprising 2 carbon atoms.

In one embodiment, the composition is characterized in that the hydrophobic radical according to formula X is a radical wherein R is a divalent linear alkyl radical comprising from 1 to 11 carbon atoms.

In one embodiment, the composition is characterized in that the hydrophobic radical according to formula X is a radical wherein R is a divalent alkyl radical comprising from 1 to 6 carbon atoms.

In one embodiment, the composition is characterized in that the hydrophobic radical according to formula X is a radical wherein R is a divalent alkyl radical comprising from 2 to 5 carbon atoms and bearing one or a plurality of amide functions ($-CONH_2$).

In one embodiment, the composition is characterized in that the hydrophobic radical according to formula X is a radical wherein R is a divalent linear alkyl radical comprising from 2 to 5 carbon atoms and bearing one or a plurality of amide functions ($-CONH_2$.

In one embodiment, the composition is characterized in that the hydrophobic radical according to formula X is a radical wherein R is radical chosen in the group consisting of the radicals represented by the formulas hereinafter:

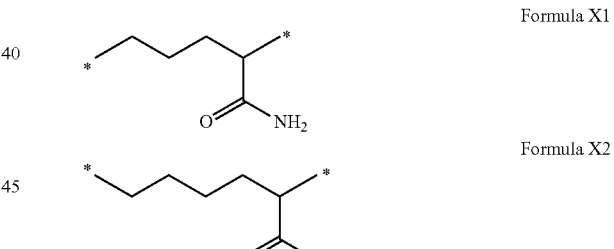

In one embodiment, the composition is characterized in that the hydrophobic radical according to formula X is a radical wherein R is a radical according to formula X1.

In one embodiment, the composition is characterized in that the hydrophobic radical according to formula X is a radical wherein R is a radical according to formula X2.

In one embodiment, the composition is characterized in that the hydrophobic radical according to formula X is a radical wherein R is bound to the co-polyamino acid via an amide function borne by the carbon in the delta or epsilon position (or in position 4 or 5) with respect to the amide function ($-CONH_2$).

In one embodiment, the composition is characterized in that the hydrophobic radical according to formula X is a radical wherein R is a non-substituted ether or polyether linear radical comprising from 4 to 14 carbon atoms and from 1 to 5 oxygen atoms.

In one embodiment, the composition is characterized in that the hydrophobic radical according to formula X is a radical wherein R is an ether radical.

In one embodiment, the composition is characterized in that the hydrophobic radical according to formula X is a radical wherein R is an ether radical comprising from 4 to 6 carbon atoms.

In one embodiment, the composition is characterized in that the hydrophobic radical according to formula X is a radical wherein R is a divalent alkyl radical comprising 6 carbon atoms.

In one embodiment, the composition is characterized in that the hydrophobic radical according to formula X is a radical wherein R is an ether radical represented by the formula

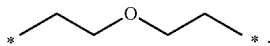

In one embodiment, the composition is characterized in that the hydrophobic radical according to formula X is a radical wherein R is a polyether radical.

In one embodiment, the composition is characterized in that the hydrophobic radical according to formula X is a radical wherein R is a polyether linear radical comprising from 6 to 10 carbon atoms and from 2 to 3 oxygen atoms.

In one embodiment, the composition is characterized in that the hydrophobic radical according to formula X is a radical wherein R is a polyether radical chosen in the group consisting of the radicals represented by the formulas hereinafter:

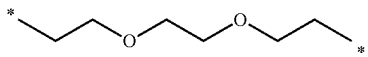

Formula X3

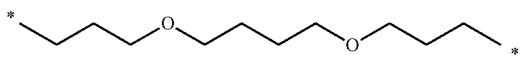

Formula X4

Formula X5

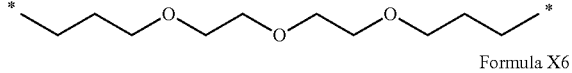

Formula X6

In one embodiment, the composition is characterized in that the hydrophobic radical according to formula X is a radical wherein R is a radical according to formula X3.

In one embodiment, the composition is characterized in that the hydrophobic radical according to formula X is a radical wherein R is a radical according to formula X4.

In one embodiment, the composition is characterized in that the hydrophobic radical according to formula X is a radical wherein R is a radical according to formula X5.

In one embodiment, the composition is characterized in that the hydrophobic radical according to formula X is a radical wherein R is a radical according to formula X6.

In one embodiment, the composition is characterized in that the hydrophobic radical according to formula X is a radical wherein R is a polyether radical chosen in the group consisting of the radicals represented by the formulas x5 and X6 hereinafter:

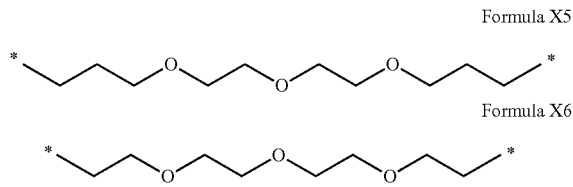

Formula X5

Formula X6

In one embodiment, the composition is characterized in that the hydrophobic radical according to formula X is a radical wherein R is a polyether radical according to formula X5.

In one embodiment, the composition is characterized in that the hydrophobic radical according to formula X is a radical wherein R is a polyether radical according to formula X6.

In one embodiment, the composition is characterized in that the hydrophobic radical according to formula X is a radical wherein the radical GpG and/or GpH is according to formula XI' wherein G is an alkyl radical comprising 6 carbon atoms represented by the formula Z hereinafter:

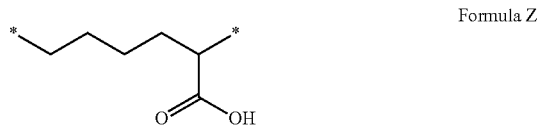 [SMILES: *CCCCC(*)C(=O)O]

Formula Z

In one embodiment, the composition is characterized in that the hydrophobic radical according to formula X is a radical wherein the radical GpG and/or GpH is according to formula XI wherein G is an alkyl radical comprising 4 carbon atoms represented by the formula Z' hereinafter:

Formula Z'

In one embodiment, the composition is characterized in that the hydrophobic radical according to formula X is a radical wherein the radical GpG and/or GpH is according to formula XI wherein G is an alkyl radical comprising 4 carbon atoms represented by —(CH2)$_2$—CH(COOH)—.

In one embodiment, the composition is characterized in that the hydrophobic radical according to formula X is a radical wherein the radical GpG and/or GpH is according to formula XI wherein G is an alkyl radical comprising 4 carbon atoms represented by —CH((CH2)$_2$COOH)—.

In one embodiment, the composition is characterized in that the hydrophobic radical according to formula X is a radical wherein the radical GpG and/or GpH is according to formula XI wherein G is an alkyl radical comprising 3 carbon atoms represented by —CH2-CH—(COOH)—.

In one embodiment, the composition is characterized in that the hydrophobic radical according to formula X is a radical wherein the radical GpG and/or GpH is according to formula XI wherein G is an alkyl radical comprising 3 carbon atoms represented by —CH(CH2COOH)—.

In one embodiment, the composition is characterized in that the hydrophobic radical according to formula X is a radical wherein the radical GpA is according to formula VIII and wherein $A_1$, $A_2$ or $A_3$ is chosen in the group consisting of radicals represented by the formulas hereinafter:

Formula Y1

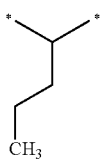

Formula Y2

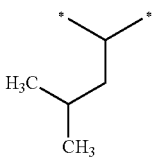

Formula Y3

Formula Y4

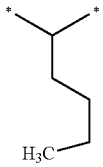

Formula Y5

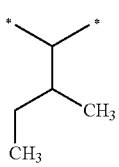

Formula Y6

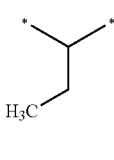

Formula Y7

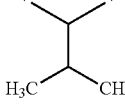

Formula Y8

Formula Y9

Formula Y10

In one embodiment, the composition is characterized in that the hydrophobic radical according to formula X is a radical wherein the radical GpC according to formula IX is chosen in the group consisting of the radicals according to formulas IXe, IXf or IXg represented hereinafter:

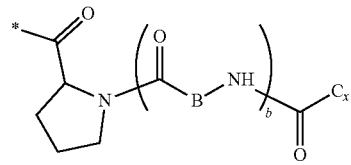

Formula IXe

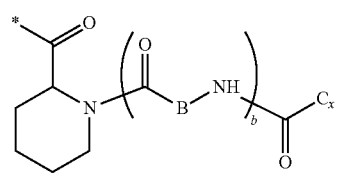

Formula IXf

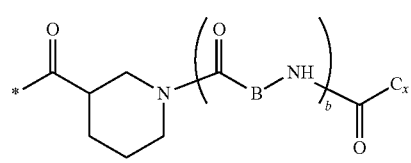

Formula IXg

In one embodiment, the composition is characterized in that the hydrophobic radical according to formula X is a radical wherein the radical GpC according to formula IX is chosen in the group consisting of the radicals according to formulas IXe, IXf or IXg wherein b is equal to 0, observing respectively the formulas IXh, IXi, and IXj represented hereinafter:

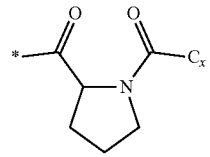

Formula IXh

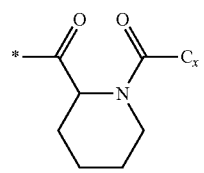

Formula IXi

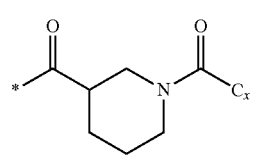

Formula IXj

In one embodiment, the composition is characterized in that the hydrophobic radical according to formula X is a radical wherein the radical GpC responds to the formula IX or IXe wherein b=0, and responds to the formula IXh.

In one embodiment, the composition is characterized in that the hydrophobic radical according to formula X is a radical wherein Cx is chosen in the group consisting of linear alkyl radicals.

In one embodiment, the composition is characterized in that the hydrophobic radical according to formula X is a radical wherein Cx is chosen in the group consisting of branched alkyl radicals.

In one embodiment, the composition is characterized in that the hydrophobic radical according to formula X is a radical wherein Cx is chosen in the group consisting of alkyl radicals comprising from 11 to 14 carbon atoms.

In one embodiment, the composition is characterized in that the hydrophobic radical according to formula X is a radical wherein Cx is chosen in the group consisting of the radicals represented by the formulas hereinafter:

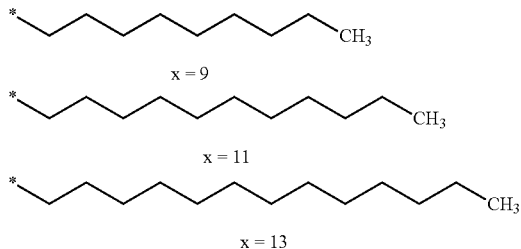

In one embodiment, the composition is characterized in that the hydrophobic radical according to formula X is a radical wherein Cx is chosen in the group consisting of alkyl radicals comprising from 15 to 16 carbon atoms.

In one embodiment, the composition is characterized in that the hydrophobic radical according to formula X is a radical wherein Cx is chosen in the group consisting of the radicals represented by the formulas hereinafter:

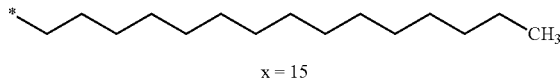

In one embodiment, the composition is characterized in that the hydrophobic radical according to formula X is a radical wherein Cx is chosen in the group consisting of the radicals represented by the formulas hereinafter:

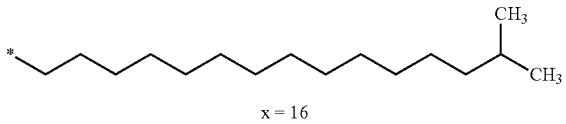 [SMILES: *CCCCCCCCCCCCCC(C)C]

In one embodiment, the composition is characterized in that the hydrophobic radical according to formula X is a radical wherein Cx is chosen in the group consisting of alkyl radicals comprising from 17 to 25 carbon atoms.

In one embodiment, the composition is characterized in that the hydrophobic radical according to formula X is a radical wherein Cx is chosen in the group consisting of alkyl radicals comprising from 17 to 18 carbon atoms.

In one embodiment, the composition is characterized in that the hydrophobic radical according to formula X is a radical wherein Cx is chosen in the group consisting of the alkyl radicals represented by the formulas hereinafter:

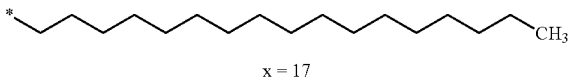 [SMILES: *CCCCCCCCCCCCCCCCC]

In one embodiment, the composition is characterized in that the hydrophobic radical according to formula X is a radical wherein Cx is chosen in the group consisting of alkyl radicals comprising from 18 to 25 carbon atoms.

In one embodiment, the composition is characterized in that the hydrophobic radical according to formula X is a radical wherein Cx is chosen in the group consisting of the alkyl radicals represented by the formulas hereinafter:

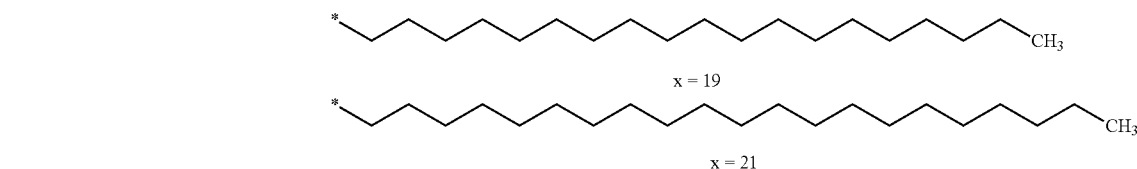

In one embodiment, the composition is characterized in that the hydrophobic radical is a radical according to formula X wherein the radical GpC according to formula IX is chosen in the group consisting of the radicals wherein Cx is chosen in the group consisting of alkyl radicals comprising 14 or 15 carbon atoms.

In one embodiment, the composition is characterized in that the hydrophobic radical is a radical according to formula VI wherein the radical GpC according to formula IV is chosen in the group consisting of the radicals wherein Cx is chosen in the group consisting of the radicals represented by the formulas hereinafter:

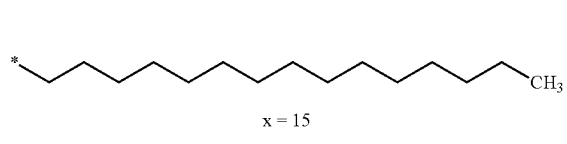 [SMILES: *CCCCCCCCCCCCCCC]

In one embodiment, the composition is characterized in that the ratio M between the number of hydrophobic radicals and the number of glutamic or aspartic units is from 0.007 to 0.35.

In one embodiment, the composition is characterized in that the ratio M between the number of hydrophobic radicals and the number of glutamic or aspartic units is from 0.007 to 0.3.

In one embodiment, the composition is characterized in that the ratio M between the number of hydrophobic radicals and the number of glutamic or aspartic units is from 0.01 to 0.3.

In one embodiment, the composition is characterized in that the ratio M between the number of hydrophobic radicals and the number of glutamic or aspartic units is from 0.02 to 0.2.

In one embodiment, the composition is characterized in that the hydrophobic radical responds to the formula X and the ratio M between the number of hydrophobic radicals and the number of glutamic or aspartic units is from 0.007 to 0.15.

In one embodiment, the composition is characterized in that the hydrophobic radical responds to the formula X and the ratio M between the number of hydrophobic radicals and the number of glutamic or aspartic units is from 0.01 to 0.1.

In one embodiment, the composition is characterized in that the hydrophobic radical responds to the formula X and the ratio M between the number of hydrophobic radicals and the number of glutamic or aspartic units is from 0.02 to 0.08.

In one embodiment, the composition is characterized in that the hydrophobic radical responds to the formula X wherein the radical Cx comprises from 9 to 10 carbon atoms and the ratio M between the number of hydrophobic radicals and the number of glutamic or aspartic units is from 0.03 to 0.15.

In one embodiment, the composition is characterized in that the hydrophobic radical responds to the formula X wherein the radical Cx comprises from 11 to 12 carbon atoms and the ratio M between the number of hydrophobic radicals and the number of glutamic or aspartic units is from 0.015 to 0.1.

In one embodiment, the composition is characterized in that the hydrophobic radical responds to the formula X wherein the radical Cx comprises from 11 to 12 carbon atoms and the ratio M between the number of hydrophobic radicals and the number of glutamic or aspartic units is from 0.02 to 0.08.

In one embodiment, the composition is characterized in that the hydrophobic radical responds to the formula X wherein the radical Cx comprises from 13 to 15 carbon atoms and the ratio M between the number of hydrophobic radicals and the number of glutamic or aspartic units is from 0.01 to 0.1.

In one embodiment, the composition is characterized in that the hydrophobic radical responds to the formula X wherein the radical Cx comprises from 13 to 15 carbon atoms and the ratio M between the number of hydrophobic radicals and the number of glutamic or aspartic units is from 0.01 to 0.06.

In one embodiment, the composition is characterized in that the hydrophobic radical responds to the formula X and the ratio M between the number of hydrophobic radicals and the number of glutamic or aspartic units is from 0.007 to 0.3.

In one embodiment, the composition is characterized in that the hydrophobic radical responds to the formula X and the ratio M between the number of hydrophobic radicals and the number of glutamic or aspartic units is from 0.01 to 0.3.

In one embodiment, the composition is characterized in that the hydrophobic radical responds to the formula X and the ratio M between the number of hydrophobic radicals and the number of glutamic or aspartic units is from 0.015 to 0.2.

In one embodiment, the composition is characterized in that the hydrophobic radical responds to the formula X and the ratio M between the number of hydrophobic radicals and the number of glutamic or aspartic units is from 0.1 to 0.35.

In one embodiment, the composition is characterized in that the hydrophobic radical responds to the formula X and the ratio M between the number of hydrophobic radicals and the number of glutamic or aspartic units is from 0.2 to 0.35.

In one embodiment, the composition is characterized in that the hydrophobic radical responds to the formula X wherein the radical Cx comprises from 11 to 14 carbon atoms and the ratio M between the number of hydrophobic radicals and the number of glutamic or aspartic units is from 0.1 to 0.2.

In one embodiment, the composition is characterized in that the hydrophobic radical responds to the formula X wherein the radical Cx comprises from 15 to 16 carbon atoms and the ratio M between the number of hydrophobic radicals and the number of glutamic or aspartic units is from 0.04 to 0.15.

In one embodiment, the composition is characterized in that the hydrophobic radical responds to the formula X wherein the radical Cx comprises from 17 to 18 carbon atoms and the ratio M between the number of hydrophobic radicals and the number of glutamic or aspartic units is from 0.02 to 0.06.

In one embodiment, the composition is characterized in that the hydrophobic radical responds to the formula X wherein the radical Cx comprises from 19 to 25 carbon atoms and the ratio M between the number of hydrophobic radicals and the number of glutamic or aspartic units is from 0.01 to 0.06.

In one embodiment, the composition is characterized in that the hydrophobic radical responds to the formula X wherein the radical Cx comprises from 19 to 25 carbon atoms and the ratio M between the number of hydrophobic radicals and the number of glutamic or aspartic units is from 0.01 to 0.05.

The invention also relates to said co-polyamino acids bearing carboxylate charges and hydrophobic radicals according to formula I and the precursors of said hydrophobic radicals.

The co-polyamino acids bearing carboxylate charges and hydrophobic radicals according to formula I are soluble in distilled water at a pH from 6 to 8, at a temperature of 25° C. and at a concentration below 100 mg/ml.

In one embodiment, the invention also relates to the precursors Hy' of said hydrophobic radicals according to formula X' as defined hereinafter:

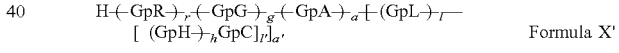

Formula X' wherein

GpR is chosen among the radicals according to formulas VII, VII' or VII":

Formula VII

Formula VII'

Formula VII"

GpG and GpH identical or different are chosen among the radicals according to formulas XI or XI':

Formula XI

Formula XI'

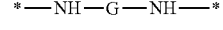

GpA is chosen among the radicals according to formula VIII

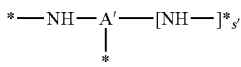

Formula VIII

Wherein A' is chosen among the radicals according to VIII', VIII" or VIII'''

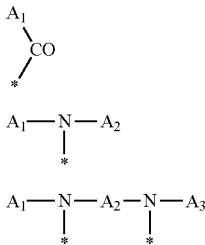

Formula VIII'

Formula VIII"

Formula VIII'''

-GpL is chosen among the radicals according to formula XII

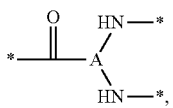

Formula XII

GpC is a radical according to formula IX:

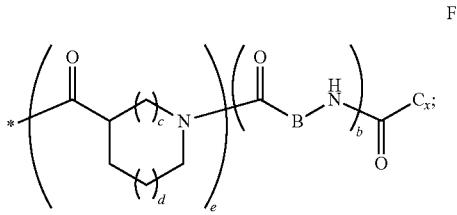

Formula IX the * indicate the binding sites of the different groups bound by amide functions;
a is an integer equal to 0 or to 1 and a'=1 if a=0 and a'=1, 2 or 3 if a=1;
a' is an integer equal to 1, to 2 or to 3
b is an integer equal to 0 or to 1;
c is an integer equal to 0 or to 1, and if c is equal to 0 then d is equal to 1 or to 2;
d is an integer equal to 0, to 1 or to 2;
e is an integer equal to 0 or to 1;
g is an integer equal to 0, to 1, to 2, to 3 to 4 to 5 or to 6;
h is an integer equal to 0, to 1, to 2, to 3 to 4 to 5 or to 6;
l is an integer equal to 0 or 1 and l'=1 if l=0 and l'=2 if l=1;
l' is an integer equal to 1 or to 2;
r is an integer equal to 0, 1 or to 2, and
s' is an integer equal to 0 or 1;
A, $A_1$, $A_2$ and $A_3$ identical or different are linear or branched alkyl radicals comprising from 1 to 8 carbon atoms and optionally substituted by a radical from a saturated, unsaturated or aromatic ring;
B is a radical chosen in the group consisting of a non-substituted ether or polyether radical comprising from 4 to 14 carbon atoms and from 1 to 5 oxygen atoms or a linear or branched alkyl radical, optionally comprising an aromatic ring, comprising from 1 to 9 carbon atoms;
$C_x$ is a radical chosen in the group consisting of a linear or branched monovalent alkyl radical, optionally comprising a cyclic part, wherein x indicates the number of carbon atoms and $6 \leq x \leq 25$:
  When the hydrophobic radical -Hy bears 1 -GpC, then $9 \leq x \leq 25$,
  When the hydrophobic radical -Hy bears 2 -GpC, then $9 \leq x \leq 15$,
  When the hydrophobic radical -Hy bears 3 -GpC, then $7 \leq x \leq 13$,
  When the hydrophobic radical -Hy bears 4 -GpC, then $7 \leq x \leq 11$,
  When the hydrophobic radical -Hy bears at least 5 -GpC, then $6 \leq x \leq 11$,
G is a linear or branched divalent alkyl radical comprising from 1 to 8 carbon atoms, said alkyl radical bearing one or a plurality of free carboxylic acid function(s).
R is a radical chosen in the group consisting of a linear or branched, divalent alkyl radical comprising from 1 to 12 carbon atoms, a linear or branched, divalent alkyl radical comprising from 1 to 12 carbon atoms bearing one or a plurality of functions —$CONH_2$ or a non-substituted ether or polyether radical comprising from 4 to 14 carbon atoms and from 1 to 5 oxygen atoms:
The hydrophobic radical(s) -Hy according to formula X being bound to the PLG:
  via a covalent bond between a carbonyl of the hydrophobic radical -Hy and a nitrogen atom borne by the PLG thus forming an amide function obtained from the reaction of an amine function borne by the PLG and an acid function borne by the precursor -Hy' of the hydrophobic radical -Hy, and
  via a covalent bond between a nitrogen atom of the hydrophobic radical -Hy and a carbonyl borne by the PLG thus forming an amide function obtained from the reaction of an amine function of the precursor -Hy' of the hydrophobic radical -Hy and an acid function borne by the PLG,
the ratio M between the number of hydrophobic radicals and the number of glutamic or aspartic units being between $0 < M \leq 0.5$;
when a plurality of hydrophobic radicals are borne by a co-polyamino acid then they are identical or different,
the degree of polymerization DP in glutamic or aspartic units for the PLG chains is from 5 to 250;
the free carboxylic acid functions being in the form of alkali cation salt chosen in the group consisting of $Na^+$ and $K^+$.

In one embodiment, the composition according to the invention is characterized in that the co-polyamino acid is obtained from a polyamino acid obtained by polymerization.

In one embodiment, the composition according to the invention is characterized in that the co-polyamino acid is obtained from a polyamino acid obtained by ring-opening polymerization of a glutamic acid N-carboxyanhydride derivative or of an aspartic acid N-carboxyanhydride derivative.

In one embodiment, the composition according to the invention is characterized in that the co-polyamino acid is obtained from a polyamino acid obtained by polymerization of a glutamic acid N-carboxyanhydride derivative or of an aspartic acid N-carboxyanhydride derivative as described in the journal article Adv. Polym. Sci. 2006, 202, 1-18 (Deming, T. J.).

In one embodiment, the composition according to the invention is characterized in that the co-polyamino acid is obtained from a polyamino acid obtained by polymerization of a glutamic acid N-carboxyanhydride derivative.

In one embodiment, the composition according to the invention is characterized in that the co-polyamino acid is obtained from a polyamino acid obtained by polymerization of a glutamic acid N-carboxyanhydride derivative chosen in the group consisting of methyl glutamate N-carboxyanhydride (GluOMe-NCA), benzyl glutamate N-carboxyanhydride (GluOBzl-NCA) and t-butyl glutamate N-carboxyanhydride (GluOtBu-NCA).

In one embodiment, the glutamic acid N-carboxyanhydride derivative is L-methyl glutamate N-carboxyanhydride (L-GluOMe-NCA).

In one embodiment, the glutamic acid N-carboxyanhydride derivative is L-benzyl glutamate N-carboxyanhydride (L-GluOBzl-NCA).

In one embodiment, the composition according to the invention is characterized in that the co-polyamino acid is obtained from a polyamino acid obtained by polymerization of a glutamic acid N-carboxyanhydride derivative or of an aspartic acid N-carboxyanhydride derivative using an organometallic complex as initiator as described in the publication Nature 1997, 390, 386-389 (Deming, T. J.).

In one embodiment, the composition according to the invention is characterized in that the co-polyamino acid is obtained from a polyamino acid obtained by polymerization of a glutamic acid N-carboxyanhydride derivative or of an aspartic acid N-carboxyanhydride derivative using ammonia or a primary amine as initiator as described in the patent FR 2,801,226 (Touraud, F.; et al.) and the references cited by this patent. Similarly, the initiator may be a polyamine so as to obtain polyamino acid comprising a plurality of PLG. Said polyamines may be chosen among diamines, triamines and tetramines. The amines of these polyamines may be primary amines.

In one embodiment, the composition according to the invention is characterized in that the co-polyamino acid is obtained from a polyamino acid obtained by polymerization of a glutamic acid N-carboxyanhydride derivative or of an aspartic acid N-carboxyanhydride derivative using hexamethyldisilazane as initiator as described in the publication J. Am. Chem. Soc. 2007, 129, 14114-14115 (Lu H.; et al.) or a silylated amine as described in the publication J. Am. Chem. Soc. 2008, 130, 12562-12563 (Lu H.; et al.).

In one embodiment, the composition according to the invention is characterized in that the synthesis method of the polyamino acid obtained by polymerization of a glutamic acid N-carboxyanhydride derivative or of an aspartic acid N-carboxyanhydride derivative from which the co-polyamino acid is obtained comprises an ester function hydrolysis step.

In one embodiment, this ester function hydrolysis step may consist of hydrolysis in acidic medium or hydrolysis in basic medium or be performed by hydrogenation.

In one embodiment, this ester group hydrolysis step is a hydrolysis in acidic medium.

In one embodiment, this ester group hydrolysis step is performed by hydrogenation.

In one embodiment, the composition according to the invention is characterized in that the co-polyamino acid is obtained from a polyamino acid obtained by depolymerization of a polyamino acid of higher molecular weight.

In one embodiment, the composition according to the invention is characterized in that the co-polyamino acid is obtained from a polyamino acid obtained by enzymatic depolymerization of a polyamino acid of higher molecular weight.

In one embodiment, the composition according to the invention is characterized in that the co-polyamino acid is obtained from a polyamino acid obtained by chemical depolymerization of a polyamino acid of higher molecular weight.

In one embodiment, the composition according to the invention is characterized in that the co-polyamino acid is obtained from a polyamino acid obtained by enzymatic and chemical depolymerization of a polyamino acid of higher molecular weight.

In one embodiment, the composition according to the invention is characterized in that the co-polyamino acid is obtained from a polyamino acid obtained by depolymerization of a polyamino acid of higher molecular weight chosen in the group consisting of sodium polyglutamate and sodium polyaspartate.

In one embodiment, the composition according to the invention is characterized in that the co-polyamino acid is obtained from a polyamino acid obtained by depolymerization of a sodium polyglutamate of higher molecular weight.

In one embodiment, the composition according to the invention is characterized in that the co-polyamino acid is obtained from a polyamino acid obtained by depolymerization of a sodium polyaspartate of higher molecular weight.

In one embodiment, the composition according to the invention is characterized in that the co-polyamino acid is obtained by grafting a hydrophobic group on a poly-L-glutamic acid or poly-L-aspartic acid using amide bond formation methods well-known to those skilled in the art.

In one embodiment, the composition according to the invention is characterized in that the co-polyamino acid is obtained by grafting a hydrophobic group on a poly-L-glutamic acid or poly-L-aspartic acid using amide bond formation methods used for peptide synthesis.

In one embodiment, the composition according to the invention is characterized in that the co-polyamino acid is obtained by grafting a hydrophobic group on a poly-L-glutamic acid or poly-L-aspartic acid as described in the patent FR 2,840,614 (Chan, Y. P.; et al.).

During synthesis of the intermediate compounds Hy and during grafting, conventional protection and deprotection techniques are used:

the one or a plurality of free carboxylic acid function(s) of Hy may be in protected form prior to grafting on the PLG via an acid protecting group, this protection is performed for example by esterification using methanol, ethanol, benzyl alcohol or t-Butanol. After grafting, the functions are deprotected, i.e. a deprotection reaction is carried out so that the carboxylic function(s) is/are free or in the form of alkali cation salt chosen in the group consisting of Na+ and K+.

the one or a plurality of amine function(s) may be in protected form prior to grafting on the PLG via an amine protecting group, this protection is performed for example by acid or basic hydrolysis with heat via the phenylmethoxycarbonyl group or the 1,1-dimethylethoxycarbonyl group. After grafting, the functions are deprotected, i.e. a deprotection reaction is carried out so that the amine functions is/are free.

In one embodiment, the concentration of co-polyamino acid bearing carboxylate charges and hydrophobic radicals is not more than 40 mg/mL.

In one embodiment, the concentration of co-polyamino acid bearing carboxylate charges and hydrophobic radicals is not more than 30 mg/mL.

In one embodiment, the concentration of co-polyamino acid bearing carboxylate charges and hydrophobic radicals is not more than 20 mg/mL.

In one embodiment, the concentration of co-polyamino acid bearing carboxylate charges and hydrophobic radicals is not more than 10 mg/mL.

In one embodiment, the concentration of co-polyamino acid bearing carboxylate charges and hydrophobic radicals is not more than 5 mg/mL.

In one embodiment, the concentration of co-polyamino acid bearing carboxylate charges and hydrophobic radicals is not more than 2.5 mg/mL.

In one embodiment, the concentration of co-polyamino acid bearing carboxylate charges and hydrophobic radicals is not more than 1 mg/mL.

In one embodiment, the concentration of co-polyamino acid bearing carboxylate charges and hydrophobic radicals is not more than 0.5 mg/mL.

Human glucagon is a highly conserved polypeptide comprising a single chain of 29 amino acid residues exhibiting the following sequence H-His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-OH.

It may be obtained in different manners, by recombination peptide synthesis.

Human glucagon is available via many sources. For example, it may consist of human glucagon produced by Bachem via peptide synthesis, particularly under the reference 407473.

In one embodiment, the mass ratio of co-polyamino acid bearing carboxylate charges and hydrophobic radicals to glucagon is from 1.0 to 25.

In one embodiment, the mass ratio of co-polyamino acid bearing carboxylate charges and hydrophobic radicals to glucagon is from 1.5 to 25.

In one embodiment, the mass ratio of co-polyamino acid bearing carboxylate charges and hydrophobic radicals to glucagon is from 2 to 20.

In one embodiment, the mass ratio of co-polyamino acid bearing carboxylate charges and hydrophobic radicals to glucagon is from 2.5 to 15.

In one embodiment, the mass ratio of co-polyamino acid bearing carboxylate charges and hydrophobic radicals to glucagon is from 2 to 10.

In one embodiment, the mass ratio of co-polyamino acid bearing carboxylate charges and hydrophobic radicals to glucagon is from 2 to 7.

Human glucagon is used at dosages varying according to the applications.

For emergency hypoglycemia treatment, the recommended dosage is 1 mg by the intramuscular or intravenous route (0.5 mg if the body mass is less than 25 kg). This administration is performed with a human glucagon solution at a concentration of 1 mg/ml.

In pumps, the envisaged daily dose is about 0.5 mg, the solutions may thus comprise from 0.25 mg/ml to 5 mg/ml of human glucagon.

According to one embodiment, the solutions may comprise from 0.5 mg/ml to 3 mg/ml of human glucagon.

In the treatment of obesity, the envisaged daily dose is about 0.5 mg, the solutions may thus comprise from 0.25 mg/ml to 5 mg/ml of human glucagon.

In one embodiment, the concentration of human glucagon is from 0.25 to 5 mg/mL.

In one embodiment, the concentration of human glucagon is from 0.5 to 4 mg/mL.

In one embodiment, the concentration of human glucagon is from 0.75 to 3 mg/mL.

In one embodiment, the concentration of human glucagon is from 0.75 to 2.5 mg/mL.

In one embodiment, the concentration of human glucagon is from 0.75 to 2 mg/mL.

In one embodiment, the concentration of human glucagon is from 1 to 2 mg/mL.

In one embodiment, the molar ratio of [hydrophobic radical]/[human glucagon] is less than 20.

In one embodiment, the molar ratio of [hydrophobic radical]/[human glucagon] is less than 15.

In one embodiment, the molar ratio of [hydrophobic radical]/[human glucagon] is less than 10.

In one embodiment, the molar ratio of [hydrophobic radical]/[human glucagon] is less than 5.

In one embodiment, the molar ratio of [hydrophobic radical]/[human glucagon] is less than 2.5.

In one embodiment, the molar ratio of [hydrophobic radical]/[human glucagon] is less than 1.5.

In one embodiment, the molar ratio of [co-polyamino acid bearing carboxylate charges and hydrophobic radicals Hy]/[human glucagon] is less than 20.

In one embodiment, the molar ratio of [co-polyamino acid bearing carboxylate charges and hydrophobic radicals Hy]/[human glucagon] is less than 15.

In one embodiment, the molar ratio of [co-polyamino acid bearing carboxylate charges and hydrophobic radicals Hy]/[human glucagon] is less than 10.

In one embodiment, the molar ratio of [co-polyamino acid bearing carboxylate charges and hydrophobic radicals Hy]/[human glucagon] is less than 5.

In one embodiment, the molar ratio of [co-polyamino acid bearing carboxylate charges and hydrophobic radicals Hy]/[human glucagon] is less than 2.5.

In one embodiment, the molar ratio of [co-polyamino acid bearing carboxylate charges and hydrophobic radicals Hy]/[human glucagon] is less than 1.5.

In one embodiment, the molar ratio of co-polyamino acid bearing carboxylate charges and hydrophobic radicals to glucagon is from 0.5 to 15.

In one embodiment, the molar ratio of co-polyamino acid bearing carboxylate charges and hydrophobic radicals to glucagon is from 1 to 10.

In one embodiment, the molar ratio of co-polyamino acid bearing carboxylate charges and hydrophobic radicals to glucagon is from 1 to 7.

In one embodiment, the molar ratio of co-polyamino acid bearing carboxylate charges and hydrophobic radicals to glucagon is from 1 to 5.

In one embodiment, the composition further comprises a nicotinic compound or any of the derivatives thereof.

In one embodiment, the composition comprises nicotinamide.

In one embodiment, the concentration of nicotinamide ranges from 10 to 160 mM.

In one embodiment, the concentration of nicotinamide ranges from 20 to 150 mM.

In one embodiment, the concentration of nicotinamide ranges from 40 to 120 mM.

In one embodiment, the concentration of nicotinamide ranges from 60 to 100 mM.

In one embodiment, the composition further comprises a polyanionic compound.

In one embodiment, the polyanionic compound is chosen in the group consisting of carboxylic polyacids and the Na$^+$, K$^+$, Ca$^{2+}$ or Mg$^{2+}$ salts thereof.

In one embodiment, the carboxylic polyacid is chosen in the group consisting of citric acid, tartaric acid, and the Na$^+$, K$^+$, Ca$^{2+}$ or Mg$^{2+}$ salts thereof.

In one embodiment, the polyanionic compound is chosen in the group consisting of phosphoric polyacids and the Na$^+$, K$^+$, Ca$^{2+}$ or Mg$^{2+}$ salts thereof.

In one embodiment, the phosphoric polyacid is triphosphate and the Na$^+$, K$^+$, Ca$^{2+}$ or Mg$^{2+}$ salts thereof.

In one embodiment, the polyanionic compound is citric acid and the Na$^+$, K$^+$, Ca$^{2+}$ or Mg$^{2+}$ salts thereof.

In one embodiment, the polyanionic compound is tartaric acid and the Na$^+$, K$^+$, Ca$^{2+}$ or Mg$^{2+}$ salts thereof.

In one embodiment, the polyanionic compound is triphosphoric acid and the Na$^+$, K$^+$, Ca$^{2+}$ or Mg$^{2+}$ salts thereof.

In one embodiment, the concentration of polyanionic compound is from 1 to 20 mM.

In one embodiment, the concentration of polyanionic compound is from 2 to 15 mM.

In one embodiment, the concentration of polyanionic compound is from 3 to 12 mM.

In one embodiment, the concentration of polyanionic compound is 10 mM.

In one embodiment, the concentration of polyanionic compound is 5 mM.

In one embodiment, the concentration of polyanionic compound is 10 mM for concentrations of glucagon from 0.5 mg/ml to 3 mg/ml.

In one embodiment, the concentration of polyanionic compound is 10 mM for concentrations of glucagon from 0.5 mg/ml to 2 mg/ml.

In one embodiment, the concentration of polyanionic compound is 10 mM for concentrations of glucagon from 1 mg/ml to 2 mg/ml.

In one embodiment, the concentration of polyanionic compound is 5 mM for concentrations of glucagon from 0.5 mg/ml to 3 mg/ml.

In one embodiment, the concentration of polyanionic compound is 5 mM for concentrations of glucagon from 0.5 mg/ml to 2 mg/ml.

In one embodiment, the concentration of polyanionic compound is 5 mM for concentrations of glucagon from 1 mg/ml to 2 mg/ml.

In one embodiment, the concentration of citric acid and the Na$^+$, K$^+$, Ca$^{2+}$ or Mg$^{2+}$ salts thereof is from 1 to 20 mM.

In one embodiment, the concentration of citric acid and the Na$^+$, K$^+$, Ca$^{2+}$ or Mg$^{2+}$ salts thereof is from 2 to 15 mM.

In one embodiment, the concentration of citric acid and the Na$^+$, K$^+$, Ca$^{2+}$ or Mg$^{2+}$ salts thereof is from 3 to 12 mM.

In one embodiment, the concentration of citric acid and the Na$^+$, K$^+$, Ca$^{2+}$ or Mg$^{2+}$ salts thereof is 10 mM.

In one embodiment, the concentration of citric acid and the Na$^+$, K$^+$, Ca$^{2+}$ or Mg$^{2+}$ salts thereof is 5 mM.

In one embodiment, the concentration of citric acid and the Na$^+$, K$^+$, Ca$^{2+}$ or Mg$^{2+}$ salts thereof is 10 mM for concentrations of glucagon from 0.5 mg/ml to 3 mg/ml.

In one embodiment, the concentration of citric acid and the Na$^+$, K$^+$, Ca$^{2+}$ or Mg$^{2+}$ salts thereof is 10 mM for concentrations of glucagon from 0.5 mg/ml to 2 mg/ml.

In one embodiment, the concentration of citric acid and the Na$^+$, K$^+$, Ca$^{2+}$ or Mg$^{2+}$ salts thereof is 10 mM for concentrations of glucagon from 1 mg/ml to 2 mg/ml.

In one embodiment, the concentration of citric acid and the Na$^+$, K$^+$, Ca$^{2+}$ or Mg$^{2+}$ salts thereof is 5 mM for concentrations of glucagon from 0.5 mg/ml to 3 mg/ml.

In one embodiment, the concentration of citric acid and the Na$^+$, K$^+$, Ca$^{2+}$ or Mg$^{2+}$ salts thereof is 5 mM for concentrations of glucagon from 0.5 mg/ml to 2 mg/ml.

In one embodiment, the concentration of citric acid and the Na$^+$, K$^+$, Ca$^{2+}$ or Mg$^{2+}$ salts thereof is 5 mM for concentrations of glucagon from 1 mg/ml to 2 mg/ml.

In one embodiment, the compositions according to the invention further comprise a gut hormone.

The term "gut hormones" denotes the hormones chosen in the group consisting of GLP-1 RAs or Glucagon like peptide-1 receptor agonists and GIP (Glucose-dependent insulinotropic peptide), oxyntomodulin (a derivative of proglucagon), peptide YY, amylin, cholecystokinin, pancreatic polypeptide (PP), ghrelin and enterostatin, the analogs or derivatives thereof and/or the pharmaceutically acceptable salts thereof.

In one embodiment, the gut hormones are analogs or derivatives of GLP-1 RA (Glucagon like peptide-1 receptor agonist) chosen in the group consisting of exenatide or Byetta® (ASTRA-ZENECA), liraglutide or Victoza® (NOVO NORDISK), lixisenatide or Lyxumia® (SANOFI), albiglutide or Tanzeum® (GSK) or dulaglutide or Trulicity® (ELI LILLY & CO), the analogs or derivatives thereof or the pharmaceutically acceptable salts thereof.

In one embodiment, the gut hormone is pramlintide or Symlin® (ASTRA-ZENECA).

In one embodiment, the gut hormone is exenatide or Byetta®, the analogs or derivatives thereof and the pharmaceutically acceptable salts thereof.

In one embodiment, the gut hormone is liraglutide or Victoza®, the analogs or derivatives thereof and the pharmaceutically acceptable salts thereof.

In one embodiment, the gut hormone is lixisenatide or Lyxumia®, the analogs or derivatives thereof and the pharmaceutically acceptable salts thereof.

In one embodiment, the gut hormone is albiglutide or Tanzeum®, the analogs or derivatives thereof and the pharmaceutically acceptable salts thereof.

In one embodiment, the gut hormone is dulaglutide or Trulicity®, the analogs or derivatives thereof and the pharmaceutically acceptable salts thereof.

In one embodiment, the gut hormone is pramlintide or Symlin®, the analogs or derivatives thereof and the pharmaceutically acceptable salts thereof.

The term "analog" denotes, when used with reference to a peptide or a protein, a peptide or a protein, wherein one or a plurality of constituent amino acid residues have been substituted by other amino acid residues and/or wherein one or a plurality of constituent amino acid residues have been removed and/or wherein one or a plurality of constituent amino acid residues have been added. The percentage of homology allowed for the present definition of an analog is 50%.

The term "derivative" denotes, when used with reference to a peptide or a protein, a peptide or a protein or an analog chemically modified by a substituent which is not present in the reference peptide or protein or analog, i.e. a peptide or a protein which has been modified by creating covalent bonds, to introduce substituents.

In one embodiment, the substituent is chosen in the group consisting of fatty chains.

In one embodiment, the concentration of gut hormone is within a range from 0.01 to 10 mg/mL.

In one embodiment, the concentration of exenatide, the analogs or derivatives thereof and the pharmaceutically acceptable salts thereof is within a range from 0.04 to 0.5 mg/mL.

In one embodiment, the concentration of liraglutide, the analogs or derivatives thereof and the pharmaceutically acceptable salts thereof is within a range from 1 to 10 mg/mL.

In one embodiment, the concentration of lixisenatide, the analogs or derivatives thereof and the pharmaceutically acceptable salts thereof is within a range from 0.01 to 1 mg/mL.

In one embodiment, the concentration of pramlintide, the analogs or derivatives thereof and the pharmaceutically acceptable salts thereof is from 0.1 to 5 mg/mL.

The invention also relates to compositions further comprising ionic species, said ionic species being suitable for improving the stability of the compositions.

The invention also relates to the use of ionic species chosen in the group of anions, cations and/or zwitterions for improving the physicochemical stability of the compositions.

In one embodiment, the ionic species comprise less than 10 carbon atoms.

Said ionic species are chosen in the group of anions, cations and/or zwitterions. The term zwitterion denotes a species bearing at least one positive charge and at least one negative charge on two non-adjacent atoms.

Said ionic species are used alone or in a mixture and preferably in a mixture.

In one embodiment, the anions are chosen among organic anions.

In one embodiment, the organic anions comprise less than 10 carbon atoms.

In one embodiment, the organic anions are chosen in the group consisting of acetate, citrate and succinate In one embodiment, the anions are chosen among inorganic anions.

In one embodiment, the inorganic anions are chosen in the group consisting of sulfates, phosphates and halides, particularly chlorides.

In one embodiment, the cations are chosen among organic cations.

In one embodiment, the organic cations comprise less than 10 carbon atoms.

In one embodiment, the organic cations are chosen in the group consisting of ammoniums, for example 2-Amino-2-(hydroxymethyl)propane-1,3-diol where the amine is in ammonium form.

In one embodiment, the cations are chosen among inorganic cations.

In one embodiment, the inorganic cations are chosen in the group consisting of zinc, in particular $Zn^{2+}$ and alkali metals, in particular $Na+$ and $K+$, In one embodiment, the zwitterions are chosen among organic zwitterions.

In one embodiment, the organic zwitterions are chosen among amino acids.

In one embodiment, the amino acids are chosen among aliphatic amino acids in the group consisting of glycine, alanine, valine, isoleucine and leucine.

In one embodiment, the amino acids are chosen among cyclic amino acids in the group consisting of proline.

In one embodiment, the amino acids are chosen among hydroxylated amino acids in the group consisting of cysteine, serine, threonine, and methionine.

In one embodiment, the amino acids are chosen among aromatic amino acids in the group consisting of phenylalanine, tyrosine and tryptophan.

In one embodiment, the amino acids are chosen among amino acids wherein the carboxyl function of the side chain is amidified in the group consisting of asparagine and glutamine.

In one embodiment, the organic zwitterions are chosen in the group consisting of amino acids having a non-charged side chain.

In one embodiment, the organic zwitterions are chosen in the group consisting of amino diacids or acidic amino acids.

In one embodiment, the amino diacids are chosen in the group consisting of glutamic acid and aspartic acid, optionally in salt form.

In one embodiment, the organic zwitterions are chosen in the group consisting of basic or so-called "cationic" amino acids.

In one embodiment, the so-called "cationic" amino acids are chosen among arginine, histidine and lysine, in particular arginine and lysine.

Most particularly, the zwitterions comprise as many negative charges as positive charges and therefore a nil overall charge at the isoelectric point and/or at a pH from 6 to 8.

Said ionic species are introduced into the compositions in salt form. The introduction thereof may be made in solid form prior to placing in solution in the compositions, or in solution form, in particular concentrated solution.

For example, the inorganic cations are added in the form of salts chosen among sodium chloride, zinc chloride, sodium phosphate, sodium sulfate, etc.

For example, the organic cations are added in the form of salts chosen among sodium or potassium citrate, sodium acetate.

For example, the amino acids are added in the form of salts chosen among arginine hydrochloride, histidine hydrochloride or in the non-salified form such as for example histidine, arginine.

In one embodiment, the total molar concentration of ionic species in the composition is greater than or equal to 10 mM.

In one embodiment, the total molar concentration of ionic species in the composition is greater than or equal to 20 mM.

In one embodiment, the total molar concentration of ionic species in the composition is greater than or equal to 30 mM.

In one embodiment, the total molar concentration of ionic species in the composition is greater than or equal to 50 mM.

In one embodiment, the total molar concentration of ionic species in the composition is greater than or equal to 75 mM.

In one embodiment, the total molar concentration of ionic species in the composition is greater than or equal to 100 mM.

In one embodiment, the total molar concentration of ionic species in the composition is greater than or equal to 200 mM.

In one embodiment, the total molar concentration of ionic species in the composition is greater than or equal to 300 mM.

In one embodiment, the total molar concentration of ionic species in the composition is greater than or equal to 500 mM.

In one embodiment, the total molar concentration of ionic species in the composition is greater than or equal to 600 mM.

In one embodiment, the total molar concentration of ionic species in the composition is greater than or equal to 700 mM.

In one embodiment, the total molar concentration of ionic species in the composition is greater than or equal to 800 mM.

In one embodiment, the total molar concentration of ionic species in the composition is greater than or equal to 900 mM.

In one embodiment, the total molar concentration of ionic species in the composition is less than or equal to 1000 mM.

In one embodiment, the total molar concentration of ionic species in the composition is less than or equal to 1500 mM.

In one embodiment, the total molar concentration of ionic species in the composition is less than or equal to 1200 mM.

In one embodiment, the total molar concentration of ionic species in the composition is less than or equal to 1000 mM.

In one embodiment, the total molar concentration of ionic species in the composition is less than or equal to 900 mM.

In one embodiment, the total molar concentration of ionic species in the composition is less than or equal to 800 mM.

In one embodiment, the total molar concentration of ionic species in the composition is less than or equal to 700 mM.

In one embodiment, the total molar concentration of ionic species in the composition is less than or equal to 600 mM.

In one embodiment, the total molar concentration of ionic species in the composition is less than or equal to 500 mM.

In one embodiment, the total molar concentration of ionic species in the composition is less than or equal to 400 mM.

In one embodiment, the total molar concentration of ionic species in the composition is less than or equal to 300 mM.

In one embodiment, the total molar concentration of ionic species in the composition is less than or equal to 200 mM.

In one embodiment, the total molar concentration of ionic species in the composition is less than or equal to 100 mM.

In one embodiment, the total molar concentration of ionic species in the composition is from 10 to 1000 mM.

In one embodiment, the total molar concentration of ionic species in the composition is from 20 to 1000 mM.

In one embodiment, the total molar concentration of ionic species in the composition is from 30 to 1000 mM.

In one embodiment, the total molar concentration of ionic species in the composition is from 50 to 1000 mM.

In one embodiment, the total molar concentration of ionic species in the composition is from 75 to 1000 mM.

In one embodiment, the total molar concentration of ionic species in the composition is from 100 to 1000 mM.

In one embodiment, the total molar concentration of ionic species in the composition is from 200 to 1000 mM.

In one embodiment, the total molar concentration of ionic species in the composition is from 300 to 1000 mM.

In one embodiment, the total molar concentration of ionic species in the composition is from 400 to 1000 mM.

In one embodiment, the total molar concentration of ionic species in the composition is from 500 to 1000 mM.

In one embodiment, the total molar concentration of ionic species in the composition is from 600 to 1000 mM.

In one embodiment, the total molar concentration of ionic species in the composition is from 10 to 900 mM.

In one embodiment, the total molar concentration of ionic species in the composition is from 20 to 900 mM.

In one embodiment, the total molar concentration of ionic species in the composition is from 30 to 900 mM.

In one embodiment, the total molar concentration of ionic species in the composition is from 50 to 900 mM.

In one embodiment, the total molar concentration of ionic species in the composition is from 75 to 900 mM.

In one embodiment, the total molar concentration of ionic species in the composition is from 100 to 900 mM.

In one embodiment, the total molar concentration of ionic species in the composition is from 200 to 900 mM.

In one embodiment, the total molar concentration of ionic species in the composition is from 300 to 900 mM.

In one embodiment, the total molar concentration of ionic species in the composition is from 400 to 900 mM.

In one embodiment, the total molar concentration of ionic species in the composition is from 500 to 900 mM.

In one embodiment, the total molar concentration of ionic species in the composition is from 600 to 900 mM.

In one embodiment, the total molar concentration of ionic species in the composition is from 10 to 800 mM.

In one embodiment, the total molar concentration of ionic species in the composition is from 20 to 800 mM.

In one embodiment, the total molar concentration of ionic species in the composition is from 30 to 800 mM.

In one embodiment, the total molar concentration of ionic species in the composition is from 50 to 800 mM.

In one embodiment, the total molar concentration of ionic species in the composition is from 75 to 800 mM.

In one embodiment, the total molar concentration of ionic species in the composition is from 100 to 800 mM.

In one embodiment, the total molar concentration of ionic species in the composition is from 200 to 800 mM.

In one embodiment, the total molar concentration of ionic species in the composition is from 300 to 800 mM.

In one embodiment, the total molar concentration of ionic species in the composition is from 400 to 800 mM.

In one embodiment, the total molar concentration of ionic species in the composition is from 500 to 800 mM.

In one embodiment, the total molar concentration of ionic species in the composition is from 600 to 800 mM.

In one embodiment, the total molar concentration of ionic species in the composition is from 10 to 700 mM.

In one embodiment, the total molar concentration of ionic species in the composition is from 20 to 700 mM.

In one embodiment, the total molar concentration of ionic species in the composition is from 30 to 700 mM.

In one embodiment, the total molar concentration of ionic species in the composition is from 50 to 700 mM.

In one embodiment, the total molar concentration of ionic species in the composition is from 75 to 700 mM.

In one embodiment, the total molar concentration of ionic species in the composition is from 100 to 700 mM.

In one embodiment, the total molar concentration of ionic species in the composition is from 200 to 700 mM.

In one embodiment, the total molar concentration of ionic species in the composition is from 300 to 700 mM.

In one embodiment, the total molar concentration of ionic species in the composition is from 400 to 700 mM.

In one embodiment, the total molar concentration of ionic species in the composition is from 500 to 700 mM.

In one embodiment, the total molar concentration of ionic species in the composition is from 600 to 700 mM.

In one embodiment, the total molar concentration of ionic species in the composition is from 10 to 600 mM.

In one embodiment, the total molar concentration of ionic species in the composition is from 20 to 600 mM.

In one embodiment, the total molar concentration of ionic species in the composition is from 30 to 600 mM.

In one embodiment, the total molar concentration of ionic species in the composition is from 50 to 600 mM.

In one embodiment, the total molar concentration of ionic species in the composition is from 75 to 600 mM.

In one embodiment, the total molar concentration of ionic species in the composition is from 100 to 600 mM.

In one embodiment, the total molar concentration of ionic species in the composition is from 200 to 600 mM.

In one embodiment, the total molar concentration of ionic species in the composition is from 300 to 600 mM.

In one embodiment, the total molar concentration of ionic species in the composition is from 400 to 600 mM.

In one embodiment, the total molar concentration of ionic species in the composition is from 500 to 600 mM.

In one embodiment, the total molar concentration of ionic species in the composition is from 10 to 500 mM.

In one embodiment, the total molar concentration of ionic species in the composition is from 20 to 500 mM.

In one embodiment, the total molar concentration of ionic species in the composition is from 30 to 500 mM.

In one embodiment, the total molar concentration of ionic species in the composition is from 50 to 500 mM.

In one embodiment, the total molar concentration of ionic species in the composition is from 75 to 500 mM.

In one embodiment, the total molar concentration of ionic species in the composition is from 100 to 500 mM.

In one embodiment, the total molar concentration of ionic species in the composition is from 200 to 500 mM.

In one embodiment, the total molar concentration of ionic species in the composition is from 300 to 500 mM.

In one embodiment, the total molar concentration of ionic species in the composition is from 400 to 500 mM.

In one embodiment, the total molar concentration of ionic species in the composition is from 10 to 400 mM.

In one embodiment, the total molar concentration of ionic species in the composition is from 20 to 400 mM.

In one embodiment, the total molar concentration of ionic species in the composition is from 30 to 400 mM.

In one embodiment, the total molar concentration of ionic species in the composition is from 50 to 400 mM.

In one embodiment, the total molar concentration of ionic species in the composition is from 75 to 400 mM.

In one embodiment, the total molar concentration of ionic species in the composition is from 100 to 400 mM.

In one embodiment, the total molar concentration of ionic species in the composition is from 200 to 400 mM.

In one embodiment, the total molar concentration of ionic species in the composition is from 300 to 400 mM.

In one embodiment, the total molar concentration of ionic species in the composition is from 10 to 300 mM.

In one embodiment, the total molar concentration of ionic species in the composition is from 20 to 300 mM.

In one embodiment, the total molar concentration of ionic species in the composition is from 30 to 300 mM.

In one embodiment, the total molar concentration of ionic species in the composition is from 50 to 300 mM.

In one embodiment, the total molar concentration of ionic species in the composition is from 75 to 300 mM.

In one embodiment, the total molar concentration of ionic species in the composition is from 100 to 300 mM.

In one embodiment, the total molar concentration of ionic species in the composition is from 200 to 300 mM.

In one embodiment, the total molar concentration of ionic species in the composition is from 10 to 200 mM.

In one embodiment, the total molar concentration of ionic species in the composition is from 20 to 200 mM.

In one embodiment, the total molar concentration of ionic species in the composition is from 30 to 200 mM.

In one embodiment, the total molar concentration of ionic species in the composition is from 50 to 200 mM.

In one embodiment, the total molar concentration of ionic species in the composition is from 75 to 200 mM.

In one embodiment, the total molar concentration of ionic species in the composition is from 100 to 200 mM.

In one embodiment, the total molar concentration of ionic species in the composition is from 10 to 100 mM.

In one embodiment, the total molar concentration of ionic species in the composition is from 20 to 100 mM.

In one embodiment, the total molar concentration of ionic species in the composition is from 30 to 100 mM.

In one embodiment, the total molar concentration of ionic species in the composition is from 50 to 100 mM.

In one embodiment, the total molar concentration of ionic species in the composition is from 75 to 100 mM.

In one embodiment, the total molar concentration of ionic species in the composition is from 10 to 75 mM.

In one embodiment, the total molar concentration of ionic species in the composition is from 20 to 75 mM.

In one embodiment, the total molar concentration of ionic species in the composition is from 30 to 75 mM.

In one embodiment, the total molar concentration of ionic species in the composition is from 50 to 75 mM.

In one embodiment, the total molar concentration of ionic species in the composition is from 10 to 50 mM.

In one embodiment, the total molar concentration of ionic species in the composition is from 20 to 50 mM.

In one embodiment, the total molar concentration of ionic species in the composition is from 30 to 50 mM.

In one embodiment, said ionic species are present at a concentration ranging from 5 to 400 mM.

In one embodiment, said ionic species are present at a concentration ranging from 5 to 300 mM.

In one embodiment, said ionic species are present at a concentration ranging from 5 to 200 mM.

In one embodiment, said ionic species are present at a concentration ranging from 5 to 100 mM.

In one embodiment, said ionic species are present at a concentration ranging from 5 to 75 mM.

In one embodiment, said ionic species are present at a concentration ranging from 5 to 50 mM.

In one embodiment, said ionic species are present at a concentration ranging from 5 to 25 mM.

In one embodiment, said ionic species are present at a concentration ranging from 5 to 20 mM.

In one embodiment, said ionic species are present at a concentration ranging from 5 to 10 mM.

In one embodiment, said ionic species are present at a concentration ranging from 10 to 400 mM.

In one embodiment, said ionic species are present at a concentration ranging from 10 to 300 mM.

In one embodiment, said ionic species are present at a concentration ranging from 10 to 200 mM.

In one embodiment, said ionic species are present at a concentration ranging from 10 to 100 mM.

In one embodiment, said ionic species are present at a concentration ranging from 10 to 75 mM.

In one embodiment, said ionic species are present at a concentration ranging from 10 to 50 mM.

In one embodiment, said ionic species are present at a concentration ranging from 10 to 25 mM.

In one embodiment, said ionic species are present at a concentration ranging from 10 to 20 mM.

In one embodiment, said ionic species are present at a concentration ranging from 20 to 300 mM.

In one embodiment, said ionic species are present at a concentration ranging from 20 to 200 mM.

In one embodiment, said ionic species are present at a concentration ranging from 20 to 100 mM.

In one embodiment, said ionic species are present at a concentration ranging from 20 to 75 mM.

In one embodiment, said ionic species are present at a concentration ranging from 20 to 50 mM.

In one embodiment, said ionic species are present at a concentration ranging from 20 to 25 mM.

In one embodiment, said ionic species are present at a concentration ranging from 50 to 300 mM.

In one embodiment, said ionic species are present at a concentration ranging from 50 to 200 mM.

In one embodiment, said ionic species are present at a concentration ranging from 50 to 100 mM.

In one embodiment, said ionic species are present at a concentration ranging from 50 to 75 mM.

In the case of inorganic cations and in particular of $Zn^{2+}$, the molar concentration thereof in the composition may be from 0.25 to 20 mM, in particular from 0.25 to 10 mM or from 0.25 to 5 mM.

In one embodiment, the ionic species present is NaCl.

In one embodiment, NaCl is present at a concentration ranging from 5 to 250 mM.

In one embodiment, NaCl is present at a concentration ranging from 10 to 150 mM.

In one embodiment, NaCl is present at a concentration ranging from 20 to 100 mM.

In one embodiment, the ionic species present is citric acid and/or the salts thereof In one embodiment, citric acid and/or the salts thereof is present at a concentration ranging from 5 to 40 mM.

In one embodiment, citric acid and/or the salts thereof is present at a concentration ranging from 7 to 30 mM.

In one embodiment, citric acid and/or the salts thereof is present at a concentration ranging from 8 to 20 mM.

In one embodiment, citric acid and/or the salts thereof is present at a concentration ranging from 10 to 15 mM.

In one embodiment, the pharmaceutical composition further comprises at least one absorption promoter chosen among absorption promoters, diffusion promoters or vasodilator agents, alone or in a mixture.

The absorption promoters include, without restricting same, surfactants, for example, bile salts, fatty acid salts or phospholipids; nicotinic agents, such as nicotinamides, nicotinic acids, niacin, niacinamide, vitamin B3 and the salts thereof; pancreatic trypsin inhibitors; magnesium salts; polyunsaturated fatty acids; didecanoyl phosphatidylcholine; aminopolycarboxylates; tolmetin; sodium caprate; salicylic acid; oleic acid; linoleic acid; eicosapentaenoic acid (EPA); docosahexaenoic acid (DHA); benzyl acid; nitrogen monoxide donors, for example, 3-(2-Hydroxy-1-(1-methylethyl)-2-nitrosohydrazino)-1-propanamine, N-ethyl-2-(1-ethyl-hydroxy-2-1-nitrosohydrazino)-ethanamine, or S-nitroso-N-acetylpenicillamine; bile acids, glycine in conjugate form with a bile acid; sodium ascorbate, potassium ascorbate; sodium salicylate, potassium salicylate, acetyl-salicylic acid, salicylosalicylic acid, aluminum acetylsalicylate, choline salicylate, salicylamide, lysine acetylsalicylate; exalamide; diflunisal; ethenzamide; EDTA; alone or in a mixture.

In one embodiment, the pharmaceutical composition further comprises at least one diffusion promoter. Examples of diffusion promoter include, without restricting same, glycosaminoglycanases, for example hyaluronidase.

In one embodiment, the pharmaceutical composition further comprises at least one vasodilator agent.

In one embodiment, the pharmaceutical composition further comprises at least one vasodilator agent inducing hyperpolarization by blocking the calcium ion channels.

In one embodiment, the vasodilator agent inducing hyperpolarization by blocking the calcium ion channels is adenosine, a hyperpolarizing agent derived from endothelium, a phosphodiesterase type 5 (PDE5) inhibitor, a potassium channel opening agent or any combination of these agents.

In one embodiment, the pharmaceutical composition further comprises at least one cAMP-mediated vasodilator agent.

In one embodiment, the pharmaceutical composition further comprises at least one cGMP-mediated vasodilator agent.

In one embodiment, the pharmaceutical composition further comprises at least one vasodilator agent chosen in the group comprising vasodilator agents acting by inducing hyperpolarization by blocking calcium ion channels, cAMP-mediated vasodilator agents, and cGMP-mediated vasodilator agents.

The at least one vasodilator agent is chosen in the group comprising, nitrogen monoxide donors, for example, nitroglycerine, isosorbide dinitrate, isosorbide mononitrate, amyl nitrate, erythrityl, tetranitrate, and nitroprussiate); prostacyclin and the analogs thereof, for example sodium epoprostenol, iloprost, epoprostenol, treprostinil or selexipag; histamine, 2-methylhistamine, 4-methylhistamine; 2-(2-pyridyl)ethylamine, 2-(2-thiazolyl)ethylamine; papaverine, papaverine hydrochloride; minoxidil; dipyridamole; hydralazine; adenosine, adenosine triphosphate; uridine trisphosphate; GPLC; L-carnitine; arginine; prostaglandin D2; potassium salts; and in some cases, α1 and α2 receptor antagonists, for example, prazosin, phenoxybenzamine, phentolamine, dibenamine, moxisylyte hydrochloride and tolazoline), betazole, dimaprit; β2 receptor agonists, for example, isoproterenol, dobutamine, albuterol, terbutaline, aminophylline, theophylline, caffeine; alprostadil, ambrisentan; cabergoline; diazoxide; dihydralazine mesilate; diltiazem hydrochloride; enoximone; flunarizine hydrochloride; *Ginkgo biloba* extract; levosimendan; molsidomine; naftidrofuryl acid oxalate; nicorandil; pentoxifylline; phenoxybenzamine chloride; piribedil base; piribedil mesilate; regadenoson monohydrate; riociguat; sildenafil citrate, tadalafil, vardenafil hydrochloride trihydrate; trimetazidine hydrochloride; trinitrine; verapamil hydrochloride; endothelin receptor antagonists, for example avanafil and bosentran monohydrate; and calcium channel inhibitors, for example, amlodipine, aranidipine, azelnidipine, barnidipine, benidipine, cilnidipine, clevidipine, isradipine, efonidipine, felodipine, lacidipine, lercanidipine, manidipine, nicardipine, nifedipine, nilvadipine, nimodipine, nisoldipine, nitrendipine, prandipine; alone or in a mixture.

According to one embodiment, the vasodilator agent is treprostinil.

In one embodiment, the composition comprises in combination a polyanionic compound and an absorption promoter.

In one embodiment, the composition comprises in combination citric acid and/or the $Na^+$, $K^+$, $Ca^{2+}$ or $Mg^{2+}$ salts thereof and an absorption promoter.

In one embodiment, the polyanionic compound is citric acid and the $Na^+$, $K^+$, $Ca^{2+}$ or $Mg^{2+}$ salts thereof.

In one embodiment, the composition comprises in combination a polyanionic compound, an absorption promoter and optionally NaCl.

In one embodiment, the composition comprises in combination citric acid and/or the $Na^+$, $K^+$, $Ca^{2+}$ or $Mg^{2+}$ salts thereof, nicotinamide or treprostinil and optionally NaCl.

In one embodiment, the composition comprises in combination citric acid and/or the $Na^+$, $K^+$, $Ca^{2+}$ or $Mg^{2+}$ salts thereof, nicotinamide or treprostinil and NaCl, and is intended to be administered via intramuscular route.

In one embodiment, the composition comprises in combination citric acid and/or the $Na^+$, $K^+$, $Ca^{2+}$ or $Mg^{2+}$ salts thereof, nicotinamide, optionally NaCl, and is intended to be administered via intramuscular route.

In one embodiment, the composition comprises in combination citric acid and/or the $Na^+$, $K^+$, $Ca^{2+}$ or $Mg^{2+}$ salts thereof, treprostinil and optionally NaCl, and is intended to be administered via intramuscular route.

In one embodiment, the composition comprises in combination citric acid and/or the $Na^+$, $K^+$, $Ca^{2+}$ or $Mg^{2+}$ salts thereof, nicotinamide or treprostinil and optionally NaCl, and is intended to be administered via the subcutaneous route.

In one embodiment, the composition comprises in combination citric acid and/or the $Na^+$, $K^+$, $Ca^{2+}$ or $Mg^{2+}$ salts thereof, nicotinamide and optionally NaCl, and is intended to be administered via the subcutaneous route.

In one embodiment, the composition comprises in combination citric acid and/or the $Na^+$, $K^+$, $Ca^{2+}$ or $Mg^{2+}$ salts thereof, treprostinil and optionally NaCl and is intended to be administered via the subcutaneous route.

In one embodiment, the compositions according to the invention are produced by mixing human glucagon solutions obtained by reconstituting freeze-dried product and solutions of GLP-1 RA (Glucagon like peptide-1 receptor agonist) GLP-1 RA, analog or derivative of GLP-1 RA said GLP-1 RA solutions being commercial or reconstituted from the freeze-dried product.

In one embodiment, the compositions according to the invention further comprise buffers.

In one embodiment, the compositions according to the invention comprise buffers at concentrations from 0 to 100 mM.

In one embodiment, the compositions according to the invention comprise buffers at concentrations from 15 to 50 mM.

In one embodiment, the compositions according to the invention comprise a buffer chosen in the group consisting of a phosphate buffer, Tris (trishydroxymethylaminomethane) or sodium citrate.

In one embodiment, the buffer is sodium phosphate.

In one embodiment, the buffer is Tris (trishydroxymethylaminomethane).

In one embodiment, the buffer is sodium citrate.

In one embodiment, the composition further comprises a zinc salt, in particular zinc chloride.

In one embodiment, the concentration of zinc chloride is from 50 to 5000 µM.

In one embodiment, the concentration of zinc chloride is from 100 to 2000 µM.

In one embodiment, the concentration of zinc chloride is from 200 to 1500 µM.

In one embodiment, the concentration of zinc chloride is from 200 to 1000 µM.

In one embodiment, the concentration of zinc is such that the molar ratio of [zinc]/[glucagon] is from 0.1 to 2.5.

In one embodiment, the concentration of zinc is such that the molar ratio of [zinc]/[glucagon] is from 0.2 to 2.

In one embodiment, the concentration of zinc is such that the molar ratio of [zinc]/[glucagon] is from 0.5 to 1.5.

In one embodiment, the concentration of zinc is such that the molar ratio of [zinc]/[glucagon] is 1.

In one embodiment, the compositions according to the invention further comprise preservatives.

In one embodiment, the preservatives are chosen in the group consisting of m-cresol and phenol alone or in a mixture.

In one embodiment, the compositions according to the invention further comprise antioxidants.

In one embodiment, the antioxidants are chosen among methionine.

In one embodiment, the concentration of the preservatives is from 10 to 50 mM.

In one embodiment, the concentration of the preservatives is from 10 to 40 mM.

In one embodiment, the compositions according to the invention further comprise a surfactant.

In one embodiment, the surfactant is chosen in the group consisting of propylene glycol or polysorbate.

The compositions according to the invention may further comprise additives such as tonicity agents.

In one embodiment, the tonicity agents are chosen in the group consisting of sodium chloride, mannitol, sucrose, sorbitol and glycerol.

The compositions according to the invention may further comprise any excipients complying with the pharmacopeias and compatible with human glucagon and gut hormones, particularly GLP-1 RAs, used at customary concentrations.

The invention also relates to a pharmaceutical formulation according to the invention, characterized in that it is obtained by drying and/or freeze-drying.

In the case of local and systemic releases, the routes of administration envisaged are by the intravenous, subcutaneous, intradermal or intramuscular route.

In one embodiment, the route of administration is the subcutaneous route.

In one embodiment, the route of administration is the intramuscular route.

The transdermal, oral, nasal, vaginal, ocular, buccal, pulmonary administration routes are also envisaged.

The invention also relates to single-dose formulations at pH from 6.6 to 7.8 comprising human glucagon.

The invention also relates to single-dose formulations at pH from 6.6 to 7.8 comprising human glucagon and a gut hormone, as defined above.

In one embodiment the single-dose formulations further comprise a substituted co-polyamino acid as defined above.

In one embodiment, the formulations are in the form of an injectable solution. In one embodiment, the GLP-1 RA, analog or derivative of GLP-1 RA is chosen in the group comprising exenatide (Byetta®), liraglutide (Victoza®), lixisenatide (Lyxumia®), albiglutide (Tanzeum®), dulaglutide (Trulicity®) or one of the derivatives thereof.

In one embodiment, the gut hormone is exenatide.

In one embodiment, the gut hormone is liraglutide.

In one embodiment, the gut hormone is lixisenatide.

In one embodiment, the gut hormone is albiglutide.

In one embodiment, the gut hormone is dulaglutide.

Moreover and equally importantly, the applicant was able to confirm that human glucagon in the presence of a co-polyamino acid bearing carboxylate charges and at least one hydrophobic radical according to the invention retains the action thereof whether alone or in combination with a gut hormone.

The preparation of a composition according to the invention offers the advantage of being suitable for being carried out by merely mixing a solution of human glucagon, a solution of GLP-1 RA, an analog or a derivative of GLP-1 RA, and a co-polyamino acid bearing carboxylate charges and at least one hydrophobic radical according to the invention, in aqueous solution or in freeze-dried form. If required, the pH of the preparation is adjusted to pH 7.

In one embodiment, the mixture of human glucagon and substituted co-polyamino acid is concentrated by ultrafiltration prior to mixing with the GLP-1 RA, analog or derivative of GLP-1 RA in aqueous solution or in freeze-dried form.

If required, the composition of the mixture is adjusted with excipients such as glycerol, m-cresol, and polysorbate (Tween®) by adding concentrated solutions of these excipients in the mixture. If required, the pH of the preparation is adjusted to 7.

DESCRIPTION OF THE FIGURES

FIG. 1: an example of graphic determination is shown in FIG. 1.

In this FIGURE, the determination of the latent period or "lag time" (LT) by monitoring the fluorescence of Thioflavin T is represented graphically, on a curve having on the y-axis the fluorescence value (in a.u arbitrary units) and on the x-axis the time in minutes.

The examples hereinafter illustrate, in a non-limiting manner, the invention.

Part A—Synthesis of Hydrophobic Intermediate Compounds Hyd for Obtaining the Radicals -Hy.

| # | HYDROPHOBIC INTERMEDIATE COMPOUNDS |
|---|---|
| A1 |  |
| A2 | 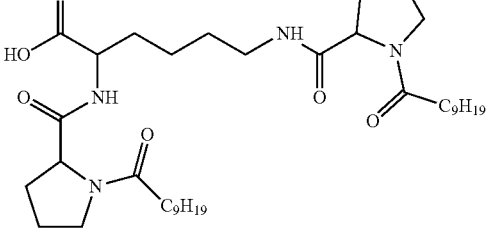 |
| A3 | 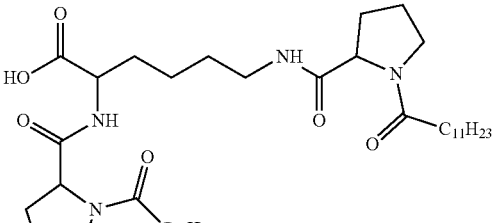 |
| A4 | 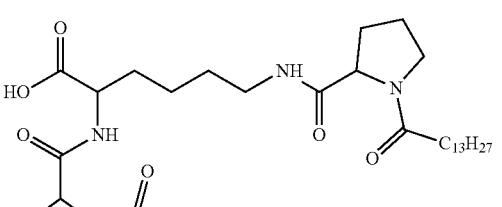 |
| A5 | 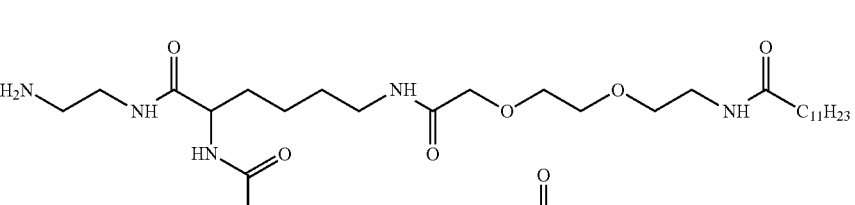 |

| # | HYDROPHOBIC INTERMEDIATE COMPOUNDS |
|---|---|
| A6 | 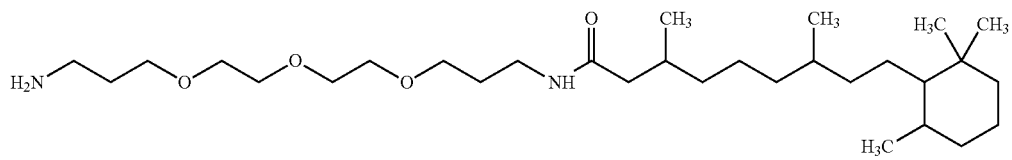 [SMILES: CC(CCCC(C)CC(=O)NCCCOCCOCCOCCCN)CCC1C(C)CCCC1(C)C] |
| A7 | 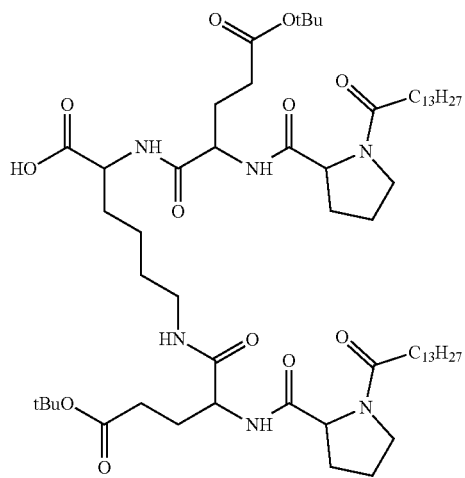 |
| A8 | 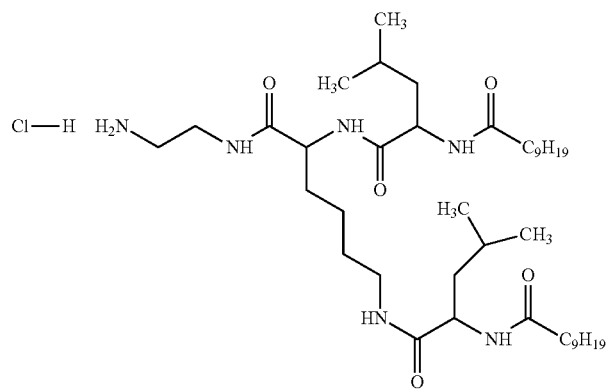 |
| A9 | 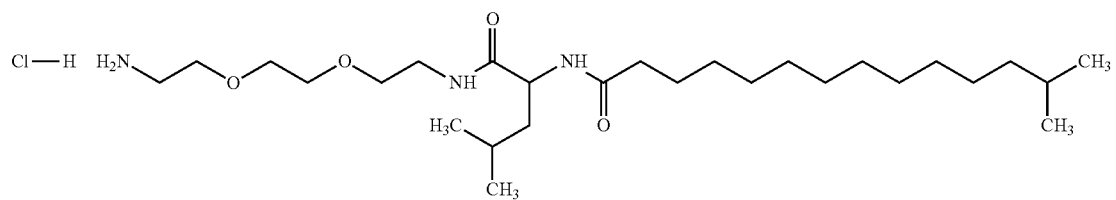 |

| # | HYDROPHOBIC INTERMEDIATE COMPOUNDS |
|---|---|
| A10 | 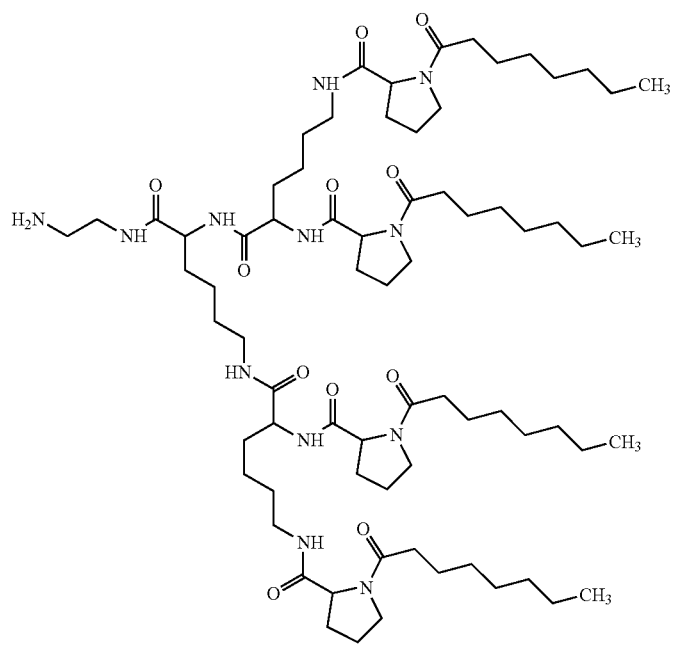 [SMILES: CCCCCCCC(=O)N1CCCC1C(=O)NCCCCC(NC(=O)C1CCCN1C(=O)CCCCCCC)C(=O)NCCCCC(NC(=O)C(CCCCNC(=O)C1CCCN1C(=O)CCCCCCC)NC(=O)C1CCCN1C(=O)CCCCCCC)C(=O)NCCN] |
| A11 | 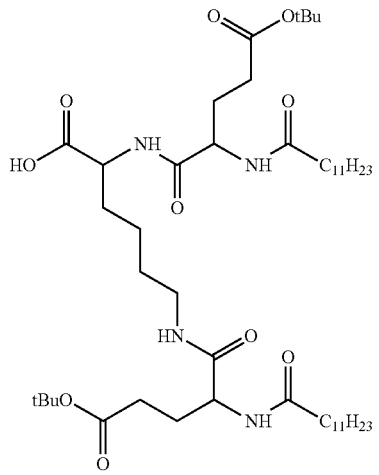 |
| A12 | 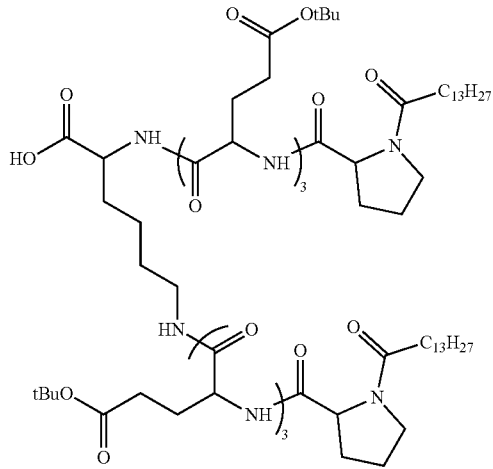 |

| # | HYDROPHOBIC INTERMEDIATE COMPOUNDS |
|---|---|
| A14 | 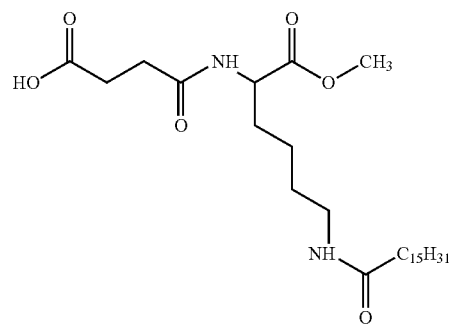 |
| A15 | 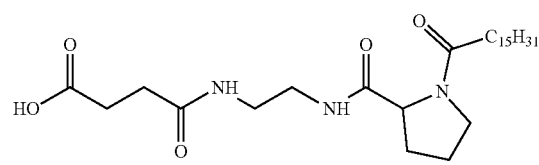 |
| A16 | 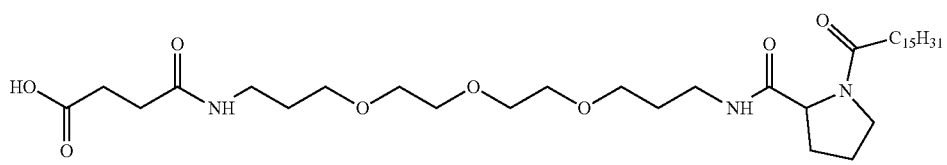 |
| A17 | 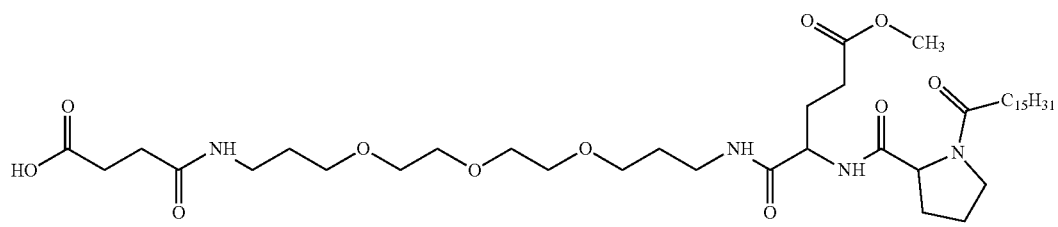 |
| A18 | 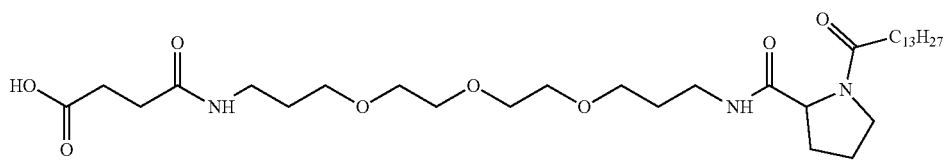 |
| A19 | 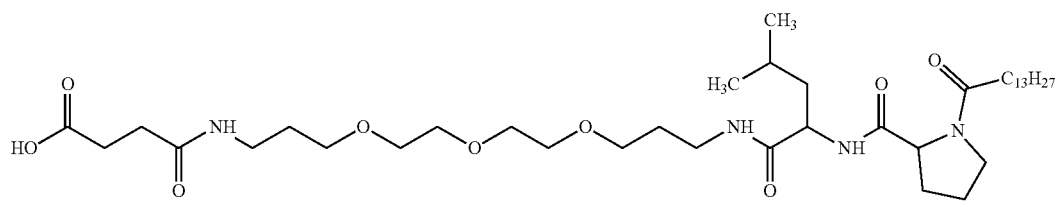 |
| A21 | 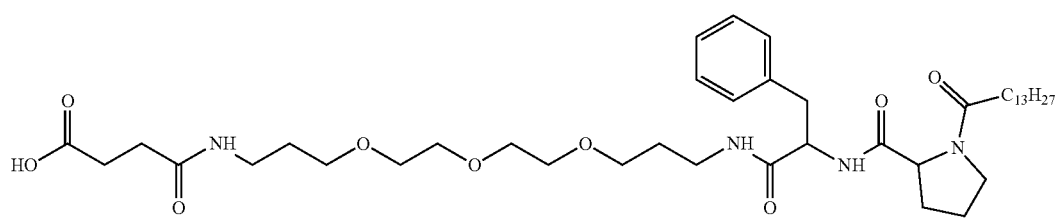 |

| # | HYDROPHOBIC INTERMEDIATE COMPOUNDS |
|---|---|
| A22 | |
| A23 | |
| A26 | |
| A27 | |

Example A1: Molecule A1

To a solution of L-proline (300.40 g, 2.61 mol) in 2 N aqueous sodium hydroxide (1.63 L) at 0° C. is added slowly over 1 h myristoyl chloride (322 g, 1.30 mol) in solution in dichloromethane (DCM, 1.63 L). At the end of the addition, the reaction medium is returned to 20° C. in 3 h, then stirred for a further 2 h. The mixture is cooled to 0° C. then a 37% HCl aqueous solution (215 mL) is added in 15 min. The reaction medium is stirred for 3 h from 0° C. to 20° C., then cooled to 3° C. 37% HCl (213 mL) is added in 15 min and the mixture is stirred for 1 h from 0° C. to 20° C. The organic phase is separated, washed with a 10% HCl aqueous solution (3×430 mL), an aqueous solution saturated with NaCl (430 mL), dried over $Na_2SO_4$, filtered on cotton then concentrated under reduced pressure. The residue is solubilized in heptane (1.31 L) at 50° C., then the solution is progressively returned to ambient temperature. After priming crystallization using a glass rod, the medium is once again heated to 40° C. for 30 min then returned to ambient temperature for 4 h. A white solid of molecule A1 is obtained after filtration on a sintered filter, washing with heptane (2×350 mL) and drying under reduced pressure.

Yield: 410 g (97%)

$^1$H NMR (CDCl$_3$, ppm): 0.88 (3H); 1.28 (20H); 1.70 (2H); 1.90-2.10 (3H); 2.36 (2H); 2.51 (1H); 3.47 (1H); 3.56 (1H); 4.61 (1H).

LC/MS (ESI): 326.4; 651.7; (calculated ([M+H]$^+$): 326.3; ([2M+H]$^+$): 651.6).

Example A2: Molecule A2

Molecule 1: Product Obtained by Reacting Decanoyl Chloride and L-Proline.

By means of a similar method to that used for the preparation of molecule A1 and applied to decanoyl chloride (75.0 g, 393.27 mmol) and to L-proline (90.55 g, 786.53 mmol), a colorless oil of molecule 1 is obtained after washing the organic phase with a 10% HCl aqueous solution (3×125 mL), an aqueous solution saturated with NaCl (125 mL), drying over Na2SO4, filtration on cotton followed by concentration under reduced pressure.

Yield: 104.64 g (99%)

$^1$H NMR (CDCl$_3$, ppm): 0.86 (3H); 1.10-1.51 (12H); 1.56-1.80 (2H); 1.83-2.46 (6H); 3.42-3.66 (2H); 4.37-4.41 (0.1H); 4.53-4.60 (0.9H); 10.12 (1H).

LC/MS (ESI): 270.1; (calculated ([M+H]$^+$): 270.2).

Molecule A2

To a solution of molecule 1 (90.0 g, 334.09 mmol) in THF (600 mL) at 0° C. are added successively N-hydroxysuccinimide (NHS, 40.4 g, 350.80 mmol) followed by dicyclohexylcarbodiimide (DCC, 72.38 g, 350.80 mmol) in solution in THF (60 mL). After 16 h of stirring at ambient temperature, the reaction medium is filtered and introduced onto a solution of L-lysine hydrochloride (30.51 g, 167.05 mmol) and N,N-diisopropylethylamine (DIPEA, 97.16 g, 751.71 mmol) in water (66 mL) and the mixture is stirred for 48 h at 20° C. After concentration under reduced pressure, water (360 mL) is added and the mixture obtained is treated by successive addition of ethyl acetate (AcOEt, 500 mL) followed by a 5% Na$_2$CO$_3$ aqueous solution (1 L). The aqueous phase is then washed once again with AcOEt (200 mL), acidified by adding a 6 N HCl aqueous solution and the product is extracted with dichloromethane (DCM, 3×250 mL). The organic phase is dried over $Na_2SO_4$, filtered and concentrated under vacuum. The white solid obtained after crystallization in AcOEt is solubilized in DCM (400 mL), the organic phase is washed with a 1 N HCl aqueous solution (200 mL) followed by an aqueous solution saturated with NaCl (200 mL), dried over $Na_2SO_4$, filtered and concentrated under vacuum. A white solid of molecule A2 is obtained after crystallization in AcOEt. Yield: 75.90 g (70%)

$^1$H NMR (DMSO-d6, ppm): 0.85 (6H); 1.10-2.04 (42 H); 2.07-2.30 (4H); 2.92-3.08 (2H); 3.28-3.57 (4H); 4.07-4.28 (2H); 4.32-4.40 (1H); 7.66-7.73 (0.6H); 7.96-8.09 (1H); 8.27 (0.4H); 12.51 (1H).

LC/MS (ESI): 649.5 (calculated ([M+H]$^+$): 649.5).

Example A3: Molecule A3

Molecule 2: Product Obtained by Reacting Lauroyl Chloride and L-Proline.

By means of a similar method to that used for the preparation of molecule A1 and applied to lauroyl chloride (27.42 g, 685.67 mmol) and to L-proline (60.0 g, 247.27 mmol), a white solid of molecule 2 is obtained.

Yield: 78.35 g (96%)

$^1$H NMR (CDCl$_3$, ppm): 0.87 (3H); 1.26 (16H); 1.70 (2H); 1.90-2.10 (3H); 2.35 (2H); 2.49 (1H); 3.48 (1H); 3.56 (1H); 4.60 (1H).

LC/MS (ESI): 298.1 (calculated ([M+H]$^+$): 298.2).

Molecule A3

By means of a similar method to that used for the preparation of molecule A2 applied to molecule 2 (42.49 g, 142.86 mmol) and to L-lysine hydrochloride (13.7 g, 75.0 mmol), a white solid of molecule A3 is obtained after crystallization in acetone.

Yield: 30.17 g (60%)

$^1$H NMR (DMSO-d$_6$, ppm): 0.86 (6H); 1.07-2.05 (50H); 2.08-2.30 (4H); 2.93-3.09 (2H); 3.28-3.57 (4H); 4.08-4.29 (2H); 4.33-4.41 (1H); 7.70 (0.6H); 7.97-8.07 (1H); 8.28 (0.4H); 12.52 (1H).

LC/MS (ESI): 705.6; (calculated ([M+H]$^+$): 705.6).

Example A4: Molecule A4

By means of a similar method to that used for the preparation of molecule A2 applied to molecule A1 (200.0 g, 614.44 mmol) and to L-lysine hydrochloride (56.11 g, 307.22 mmol), a white solid of molecule A4 is obtained after crystallization in ethyl acetate.

Yield: 176.0 g (95%)

$^1$H NMR (DMSO-d$_6$, ppm): 0.85 (6H); 1.08-1.51 (48H); 1.53-2.04 (10H); 2.08-2.30 (4H); 2.93-3.09 (2H); 3.31-3.55 (4H); 4.10-4.40 (3H); 7.68 (0.6H); 7.97 (1H); 8.27 (0.4H); 12.50 (1H).

LC/MS (ESI): 761.8; (calculated ([M+H]$^+$): 761.6).

Example A5: Molecule A5

Molecule 3: Product Obtained by Reacting Fmoc-Lys (Fmoc)-OH and 2-Cl-trityl Chloride Resin.

To a suspension of Fmoc-Lys(Fmoc)-OH (7.32 g, 12.40 mmol) in DCM (60 mL) at ambient temperature is added DIPEA (4.32 mL, 24.80 mmol). After complete solubilization (10 min), the solution obtained is poured onto 2-Cl-trityl chloride resin (100-200 mesh, 1% DVB, 1.24 mmol/g) (4.00 g, 4.96 mmol) previously washed with DCM, in a reaction vessel suitable for solid substrate peptide synthesis. After 2 h of stirring at ambient temperature, HPLC grade methanol (0.8 mL/g resin, 3.2 mL) is added and the medium is stirred at ambient temperature for 15 min. The resin is filtered, washed successively with DCM (3×60 mL), DMF (2×60 mL), DCM (2×60 mL), isopropanol (1×60 mL) and DCM (3×60 mL).

Molecule 4: Product Obtained by Reacting Molecule 3 and an 80:20 DMF/Piperidine Mixture.

Molecule 3, previously washed with DMF, is treated with an 80:20 DMF/piperidine mixture (60 mL). After 30 min of stirring at ambient temperature, the resin is filtered, washed successively with DMF (3×60 mL), isopropanol (1×60 mL) and DCM (3×60 mL).

Molecule 5: Product Obtained by Reacting Molecule 4 and 8-(9-Fluorenylmethyloxycarbonyl-amino)-3,6-dioxaoctanoic acid (Fmoc-O2Oc-OH).

To a suspension of Fmoc-O2Oc-OH (9.56 g, 24.80 mmol) and 1-[bis(dimethylamino)methylene]-1H-1,2,3-triazolo[4,5-b]pyridinium 3-oxide hexafluorophosphate (HATU, 9.43 g, 24.80 mmol) in a 1:1 DMF/DCM mixture (60 mL) is added DIPEA (8.64 mL, 49.60 mmol). After complete solubilization, the solution obtained is poured onto molecule 4. After 2 h of stirring at ambient temperature, the resin is filtered, washed successively with DMF (3×60 mL), isopropanol (1×60 mL) and DCM (3×60 mL).

Molecule 6: Product Obtained by Reacting Molecule 5 and an 80:20 DMF/Piperidine Mixture.

By means of a similar method to that used for molecule 4 applied to molecule 5, molecule 6 is obtained.

Molecule 7: Product Obtained by Reacting Molecule 6 and Lauric Acid.

By means of a similar method to that used for molecule 5 applied to molecule 6 and to lauric acid (4.97 g, 24.80 mmol) in DMF (60 mL), molecule 7 is obtained.

Molecule 8: Product Obtained by Reacting Molecule 7 and an 80:20 Dichloromethane/1,1,1,3,3,3-Hexafluoro-2-Propanol (HFIP) Mixture.

Molecule 7 is treated with an 80:20 dichloromethane/1,1,1,3,3,3-hexafluoro-2-propanol (HFIP) mixture (60 mL). After 20 min of stirring at ambient temperature, the resin is filtered and washed successively with dichloromethane (2×60 mL). The solvents are evaporated at reduced pressure. Two co-evaporations are then carried out on the residue with dichloromethane (60 mL) followed by diisopropylether (60 mL). A white solid of molecule 8 is obtained after recrystallization in acetonitrile.

Yield: 2.63 g (66% in 6 stages)

$^1$H NMR (CDCl$_3$, ppm): 0.87 (6H); 1.09-1.66 (40H); 1.77-1.98 (2H); 2.13-2.29 (4H); 3.24-3.75 (18H); 3.95-4.07 (4H); 4.65-4.70 (1H); 6.23-6.37 (1H); 6.39-6.62 (1H); 6.74-6.91 (11H); 7.38-7.54 (1H).

LC/MS (ESI): 801.6 (calculated ([M+H]$^+$): 801.6).

Molecule 9: Product Obtained by Reacting Molecule 8 and N-Boc Ethylenediamine.

To a solution of molecule 8 (2.63 g, 3.29 mmol) in chloroform (20 mL) at ambient temperature are added successively N-hydroxybenzotriazole (HOBt, 654 mg, 4.27 mmol) and N-Boc ethylenediamine (BocEDA, 580 mg, 3.62 mmol). The mixture is cooled to 0° C. then (3-dimethylaminopropyl)-N'-ethylcarbodiimide hydrochloride (EDC, 819 mg, 4.27 mmol) is added. The reaction medium is stirred for 15 min at 0° C. followed by 18 h at ambient temperature. The organic phase is washed with an aqueous solution saturated with NH$_4$Cl (2×10 mL), an aqueous solution saturated with NaHCO$_3$ (2×10 mL), and an aqueous solution saturated with NaCl (2×10 mL). The organic phase is dried over Na$_2$SO$_4$, filtered and concentrated under reduced pressure. A white solid of molecule 9 is obtained after purification by silica gel chromatography (eluent: dichloromethane, methanol).

Yield: 2.37 g (76%)

$^1$H NMR (CDCl$_3$, ppm): 0.87 (6H); 1.08-1.47 (34H); 1.43 (9H); 1.48-1.70 (7H); 1.78-1.87 (1H); 2.14-2.25 (4H); 3.16-3.71 (22H); 3.92-4.04 (4H); 4.47-4.52 (1H); 5.33 (1H); 6.10 (1H); 6.65-7.01 (1H); 7.11-7.30 (2H); 7.47-7.63 (1H).

Molecule A5

To a solution of molecule 9 (2.37 g, 2.51 mmol) in dichloromethane (50 mL) at ambient temperature is added a 4 M HCl solution in dioxane (6.3 mL) then the medium is stirred for 2 h at ambient temperature. After concentration under reduced pressure, the residue is solubilized in dichloromethane (50 mL) then washed with a 1 N NaOH aqueous solution (2×12.5 mL) and an aqueous solution saturated with NaCl (25 mL). The organic phase is dried over Na$_2$SO$_4$, filtered and concentrated under reduced pressure. A white solid of molecule A5 is obtained after recrystallization in acetonitrile.

Yield: 1.57 g (74%)

$^1$H NMR (CDCl$_3$, ppm): 0.87 (6H); 1.08-1.43 (34H); 1.48-1.71 (7H); 1.74-1.93 (3H); 2.14-2.25 (4H); 2.79-2.86 (2H); 3.17-3.71 (20H); 3.93-4.05 (4H); 4.47-4.54 (1H); 6.08-6.29 (1H); 6.84-7.01 (1H); 7.15-7.32 (2H); 7.50-7.64 (1H).

LC/MS (ESI): 843.6 (calculated ([M+H]$^+$): 843.7).

Example A6: Molecule A6

Molecule 10: Product Obtained by Hydrogenating Retinoic Acid.

A solution of retinoic acid (19.0 g, 63.24 mmol) in methanol (450 mL) in the presence of 10% palladium on carbon (1.9 g) is placed in a hydrogen atmosphere (1 atm) at ambient temperature. After overnight, the reaction medium is filtered on a sintered filter and the filtrate is then concentrated under reduced pressure. A colorless oil of molecule 10 is obtained.

Yield: 19.50 g (99%)

$^1$H NMR (CDCl$_3$, ppm): 0.45-2.01 (35 H); 2.10-2.17 (1H); 2.33-2.38 (1H); 11.14 (1H).

LC/MS (ESI): 309.3; (calculated ([M−H]$^-$): 309.3).

Molecule 11: Product Obtained by Coupling Boc-1-amino-4,7,10-trioxa-13-tridecane Amine (BocTOTA) and Molecule 10.

By means of a similar method to that used for the preparation of molecule 9 applied to molecule 10 (19.3 g, 62.15 mmol) and to BocTOTA (23.9 g, 74.58 mmol), an orange oil of molecule 11 is obtained.

Yield: 37.05 g (97%)

$^1$H NMR (CDCl$_3$, ppm): 0.43-1.71 (49 H); 2.13-2.17 (1H); 3.17-3.24 (2H); 3.32-3.39 (2H); 3.51-3.66 (12H); 4.77 (0.1H); 4.94 (0.9H); 6.13 (0.9H); 6.29 (0.1H).

LC/MS (ESI): 613.5; (calculated ([M+H]$^+$): 613.5).

Molecule A6

By means of a similar method to that used for the preparation of molecule A5 applied to molecule 11 (34.9 g, 56.94 mmol), an orange oil of molecule A6 is obtained.

Yield: 28.5 g (97%)

$^1$H NMR (CDC$_3$, ppm): 0.41-1.96 (42 H); 2.13 (1H); 2.78 (2H); 3.31-3.36 (2H); 3.53 (4H); 3.55-3.58 (4H); 3.60-3.63 (4H); 6.43 (1H).

LC/MS (ESI): 513.5; (calculated ([M+H]$^+$): 513.5).

Example A7: Molecule A7

Molecule 12: Product Obtained by Reacting Molecule 4 and Fmoc-Glu(OtBu)-OH.

To a suspension of Fmoc-Glu(OtBu)-OH (10.55 g, 24.80 mmol) and HATU (9.43 g, 24.80 mmol) in a 1:1 DMF/dichloromethane mixture (60 mL) is added DIPEA (8.64 mL, 49.60 mmol). After complete solubilization, the solution obtained is poured onto molecule 4. After 2 h of stirring at ambient temperature, the resin is filtered, washed successively with DMF (3×60 mL), isopropanol (1×60 mL) and dichloromethane (3×60 mL).

Molecule 13: Product Obtained by Reacting Molecule 12 and a 50:50 DMF/Morpholine Mixture.

Molecule 12, previously washed with DMF, is treated with a 50:50 DMF/morpholine mixture (60 mL). After 1 h 15 of stirring at ambient temperature, the resin is filtered, washed successively with DMF (3×60 mL), isopropanol (1×60 mL) and dichloromethane (3×60 mL).

Molecule 14: Product Obtained by Reacting Molecule A1 and Molecule 13.

By means of a similar method to that used for molecule 12 applied to molecule 13 and to molecule A1 (8.07 g, 24.80 mmol) in DMF (60 mL), molecule 14 is obtained.

Molecule A7

By means of a similar method to that used for the preparation of molecule 8 and applied to molecule 14, a white solid of molecule A7 is obtained after purification by silica gel chromatography (eluent: DCM, methanol).

Yield: 2.92 g (52% in 6 stages)

$^1$H NMR (DMSO-d6, ppm): 0.85 (6H); 1.07-2.32 (88H); 2.95-3.09 (2H); 3.28-3.60 (4H); 4.06-4.19 (1.7H); 4.21-4.38 (2.6H); 4.40-4.46 (0.7H); 7.56-7.63 (0.7H); 7.78-8.09 (2.6H); 8.22-8.31 (0.7H); 12.64 (1H).

LC/MS (ESI): 1131.8 (calculated ([M+H]$^+$): 1131.8).

Example A8: Molecule A8

Molecule 15: Product Obtained by Reacting Decanoic Acid and L-Leucine.

By means of a similar method to that used for the preparation of molecule A2 applied to decanoic acid (8.77 g, 50.94 mmol) and to L-leucine (7.00 g, 53.36 mmol), a white solid of molecule 15 is obtained.

Yield: 9.17 g (66%)

$^1$H NMR (DMSO-d6, ppm): 0.82-0.89 (9H); 1.18-1.65 (17H); 2.04-2.14 (2H); 4.19-4.23 (1H); 7.98 (1H); 12.40 (1H).

LC/MS (ESI): 286.2 (calculated ([M+H]$^+$): 286.2).

Molecule 16: Product Obtained by Reacting Molecule 15 and L-Lysine Methyl Ester.

To a solution of molecule 15 (9.16 g, 32.11 mmol) in THF (160 mL) are added successively triethylamine (8.12 g, 80.27 mmol) and 2-(1H-benzotriazol-1-yl)-1,1,3,3-tetramethyluronium tetrafluoroborate (TBTU) and the medium is stirred for 30 min at ambient temperature. L-lysine methyl ester dihydrochloride (3.93 g, 16.86 mmol) is added and the reaction medium is stirred for 3 h then concentrated under reduced pressure. The residue is diluted with AcOEt (200 mL), the organic phase is filtered and washed with a 1 N HCl aqueous solution then with water, dried over Na$_2$SO$_4$, filtered and concentrated under reduced pressure. A white solid of molecule 16 is obtained after triturating the residue in acetonitrile.

Yield: 7.33 g (66%)

$^1$H NMR (DMSO-d6, ppm): 0.80-0.91 (18H); 1.06-1.72 (38H); 2.03-2.16 (4H); 2.91-3.07 (2H); 3.60 (1.15H); 3.61 (1.85H); 4.13-4.28 (2H); 4.33-4.44 (1H); 7.79-7.92 (3H); 8.13-8.26 (1H).

LC/MS (ESI) 695.7 (calculated ([M+H]$^+$): 695.6).

Molecule 17: Product Obtained by Saponifying Molecule 16.

To a solution of molecule 16 (7.33 g, 10.55 mmol) in a THF/methanol/water mixture (105 mL) is added LiGH (505.13 mg, 21.09 mmol) at 0° C. then the medium is stirred for 20 h at ambient temperature and concentrated under reduced pressure. The aqueous phase is acidified with a 1 N HCl solution to pH 1 and the solid formed is filtered, washed with water and dried under reduced pressure to arrive at a white solid of molecule 17.

Yield: 7.09 g (99%)

$^1$H NMR (DMSO-d6, ppm): 0.80-0.89 (18H); 1.18-1.73 (40H); 2.03-2.16 (4H); 2.91-3.05 (2H); 4.03-4.13 (1H); 4.21-4.27 (1H); 4.31-4.40 (1H); 7.79-8.02 (4H).

LC/MS (ESI): 681.7 (calculated ([M+H]$^+$): 681.6).

Molecule 18: Product Obtained by Reacting Molecule 17 and N-Boc Ethylenediamine.

By means of a similar method to that used for the preparation of molecule 16 applied to molecule 17 (7.09 g, 10.41 mmol) and to N-Boc ethylenediamine (1.83 g, 11.45 mmol), a white solid of molecule 18 is obtained after trituration in acetonitrile.

Yield: 6.64 g (77%)

$^1$H NMR (DMSO-d6, ppm): 0.80-0.91 (18H); 1.15-1.73 (49H); 2.03-2.18 (4H); 2.92-3.13 (6H); 4.05-4.30 (3H); 6.71-6.83 (1H); 7.69-8.23 (5H).

LC/MS (ESI): 824.0 (calculated ([M+H]$^+$): 823.7).

Molecule A8

By means of a similar method to that used for molecule A5 applied to molecule 18 (3.00 g, 3.64 mmol) without basic washing, a beige solid of molecule A8 in hydrochloride salt form is obtained after co-evaporating the residue 4 times in methanol.

Yield: 2.66 g (96%)

$^1$H NMR (DMSO-d6, ppm): 0.80-0.91 (18H); 1.15-1.76 (40H); 2.03-2.19 (4H); 1.78-2.89 (2H); 2.91-3.07 (2H); 3.22-3.37 (2H); 4.08-4.14 (1H); 4.17-4.28 (2H); 7.81-8.36 (8H).

LC/MS (ESI): 723.7 (calculated ([M+H]$^+$): 723.6).

Example A9: Molecule A9

Molecule 19: 13-Methyltetradecanoic Acid.

In a three-neck round-bottom flask under argon, magnesium (5.50 g, 226.3 mmol) chips are introduced. The magnesium is covered with anhydrous THF (25 mL) and a few drops of 1-bromo-2-methylpropane are added at ambient temperature to initiate the reaction. After observing an exotherm and slight turbidity of the medium, the remaining 1-bromo-2-methylpropane (28.42 g, 207 mmol) diluted in THF (60 mL) is added dropwise in 1 h whereas the temperature of the medium remains stable from 65 to 70° C. The reaction medium is then heated under reflux for 2 h.

In a threeneck round-bottom flask under argon, to a solution of CuCl (280 mg, 2.83 mmol) dissolved in N-methylpyrrolidone (NMP) previously distilled at 0° C. is added dropwise a solution of 11-bromoundecanoic acid (25 g, 94.27 mmol) dissolved in THF (60 mL). To this solution is then added dropwise the slightly warm organomagnesium solution diluted in THF (50 mL) so as to maintain the temperature of the medium below 25° C. The mixture is then stirred at ambient temperature for 16 h. The medium is cooled to 0° C. and the reaction is stopped by slowly adding a 1 N HCl aqueous solution to pH 1 (300 mL) and the medium is extracted with hexane (100 mL) and with ethyl acetate (2×75 mL). After washing the organic phase with a 1 N HCl aqueous solution (100 mL), water (100 mL) and drying over Na$_2$SO$_4$, the solution is filtered and concentrated under vacuum to produce a brown solid. After purification by flash chromatography (cyclohexane, ethyl acetate), a white solid is obtained.

Yield: 18.1 g (79%)

$^1$H NMR (CDCl$_3$, ppm): 0.87 (6H); 1.11-1.18 (2H); 1.20-1.38 (16H); 1.51 (1H); 1.63 (2H); 2.35 (2H).

Molecule 20: Product Obtained by Reacting Molecule 19 and L-Leucine.

To a solution of molecule 19 (18.05 g, 74.46 mmol) in THF (745 mL) at ambient temperature are added successively DCC (14.63 g, 70.92 mmol) and NHS (8.16 g, 70.92 mmol). After 40 h of stirring at ambient temperature, the medium is cooled to 0° C. for 20 min, filtered on a sintered filter. L-leucine (9.77 g, 74.46 mmol), DIPEA (86 mL) and water (150 mL) are added to the filtrate. After 20 h of stirring at ambient temperature, the medium is diluted with a saturated aqueous solution of NaHCO$_3$ (200 mL). The aqueous phase is washed with ethyl acetate (2×200 mL) and acidified with a 2 N HCl solution to pH 1. The precipitate is filtered, rinsed with plenty of water and dried under vacuum at 50° C. Three times, the solid is triturated in pentane, sonicated then filtered to produce a white solid.

Yield: 18.8 g (75%)

$^1$H NMR (CDCl$_3$, ppm): 0.86 (6H); 0.96 (6H); 1.12-1.18 (2H); 1.20-1.78 (22H); 2.24 (2H); 4.58-4.63 (1H); 5.89 (1H).

LC/MS (ESI): 356.2; (calculated ([M+H]$^+$): 356.6).

Molecule 21: Product Obtained by Reacting Molecule 20 and Boc-tri(ethyleneglycol)diamine.

To a solution of molecule 20 (16.7 g, 46.97 mmol) in THF (235 mL) are added successively DIPEA (20.3 mL) and TBTU at ambient temperature. After 20 min of stirring, Boc-tri(ethyleneglycol)diamine (14 g, 56.36 mmol) is added. After stirring at ambient temperature for 5 h, the mixture is concentrated under vacuum. The residue is taken up with ethyl acetate (500 mL), washed with a saturated aqueous solution of NaHCO$_3$ (3×200 mL), a 1 N HCl aqueous solution (3×200 mL) and an aqueous solution saturated with NaCl (3×200 mL). After drying over Na$_2$SO$_4$, filtration and concentration under vacuum, the residue is purified by flash chromatography (cyclohexane, ethyl acetate, methanol) to produce a colorless oil.

Yield: 23.5 g (85%)

$^1$H NMR (CDCl$_3$, ppm): 0.86 (6H); 0.93 (6H); 1.10-1.17 (2H); 1.19-1.08 (31H); 2.18 (2H); 3.23-3.65 (12H); 4.41-4.56 (1H); 5.12-5.47 (1H); 5.99-6.11 (0.75H); 6.48-6.65 (1H); 7.30-7.40 (0.25H).

Molecule A9

By means of a similar method to that used for the preparation of molecule A5 applied to molecule 21 (23.46 g, 40.04 mmol) without basic washing, the residue obtained after concentration under vacuum is triturated in an acetonitrile/acetone mixture. The supernatant is removed and the pasty residue is dried under vacuum. The residue is triturated in acetone (150 mL) and the white solid of molecule A9 in hydrochloride salt form is filtered, rinsed with acetone then dried under vacuum.

Yield: 13.0 g (64%)

$^1$H NMR (DMSO-d6, ppm): 0.79-0.90 (12H); 1.09-1.61 (24H); 2.03-2.17 (2H); 2.92-2.98 (2H); 3.15-3.23 (2H); 3.40 (2H); 3.50-3.58 (4H); 3.61 (2H); 4.30-4.23 (1H); 7.88-8.14 (5H).

LC/MS (ESI): 486.4; (calculated ([M-Cl]$^+$): 486.8).

Example A10: Molecule A10

Molecule 22: Product Obtained by Reacting Octanoyl Chloride and L-Proline.

By means of a similar method to that used for the preparation of molecule A1 and applied to octanoyl chloride (150.0 g, 0.922 mol) and to L-proline (212.3 g, 1.844 mol), a colorless oil of molecule 22 is obtained after washing the organic phase with a 10% HCl aqueous solution (3×300 mL), an aqueous solution saturated with NaCl (300 mL), drying over Na$_2$SO$_4$, filtration on cotton, concentration under reduced pressure, then the residue is purified by flash chromatography (eluent: DCM, MeOH)

Yield: 134 g (60%)

$^1$H NMR (CDCl$_3$, ppm): 0.87 (3H); 1.10-1.52 (8H); 1.57-1.74 (2H); 1.79-2.52 (6H); 3.37-3.67 (2H); 4.37-4.42 (0.07H); 4.53-5.63 (0.93H); 9.83 (1H).

LC/MS (ESI): 242.1; (calculated ([M+H]$^+$): 242.2).

Molecule 23: Product Obtained by Coupling Molecule 22 and L-Leucine.

To a solution of molecule 22 (132 g, 0.547 mol) in THF (924 mL) cooled to a temperature below 5° C. are added successively NHS (66.1 g, 0.574 mol) and DCC (118.5 g, 0.574 mol). After 21 h of stirring, the precipitate is removed by precipitation and the filtrate is added in 30 min to a solution of L-lysine (41.98 g, 0.287 mol) in a mixture of deionized water (82 mL) and DIPEA (476 mL, 2.735 mol) at 15° C. After 23 h of stirring at ambient temperature, the reaction medium is concentrated under reduced pressure to produce an oily residue which is diluted in water (1.3 L). The aqueous phase is washed twice with AcOEt (2×0.5 L), cooled to a temperature below 10° C., acidified by adding a 6 N HCl solution (120 mL) to attain a pH of 1 then extracted three times with DCM (3×0.6 L). The organic phases are combined, washed with a saturated NaCl solution (0.6 L), dried over Na$_2$SO$_4$ then concentrated under reduced pressure. The foam obtained is taken up with acetone (240 mL) under reflux for 2 h. After leaving overnight at 10° C., pentane (240 mL) is added dropwise. After 1 h of stirring, the precipitate is retrieved by filtration under vacuum, washed with a 1:1 mixture of pentane and acetone (150 mL) then dried under vacuum.

Yield: 83.9 g (52%)

$^1$H NMR (CDCl$_3$, ppm): 0.87 (6H); 1.06-1.78 (25H); 1.80-2.41 (13H); 2.80-3.72 (6H); 4.30-4.39 (0.15H); 4.46-4.70 (2.85H); 7.84 (1H); 7.93 (1H).

LC/MS (ESI): 593.5; (calculated ([M+H]$^+$): 593.4).

Molecule 24: Product Obtained by Coupling Molecule 23 and L-Lysine Methyl Ester (LysOMe).

To molecule 23 (76.26 g, 0.129 mol) are successively added HOPO (3.57 g, 32.1 mmol), LysOMe dihydrochloride (15.0 g, 64.3 mmol) and EDC (34.53 g, 0.18 mol). Then DMF (600 mL) previously cooled to 5° C. is added. After dissolution, triethylamine (43.9 mL, 0.315 mol) is added dropwise while maintaining the temperature below 5° C. for 2 h after addition. After leaving overnight at ambient temperature, the reaction medium is poured onto a mixture of water/ice (2 kg) and DCM (0.5 L). After 15 min of stirring, the phases are separated. The aqueous phase is extracted twice with DCM (2×0.4 L). The organic phases are combined, washed with a 1 N HCl solution (0.5 L) then with a saturated NaCl solution (0.5 L), dried over Na$_2$SO$_4$, concentrated under reduced pressure, then the residue is purified by flash chromatography (eluent: DCM, MeOH).

Yield: 56.7 g (67%)

$^1$H NMR (CDCl$_3$, ppm): 0.87 (12H); 1.10-2.40 (82H); 2.86-3.72 (17H); 4.16-4.60 (7H); 6.83-8.01 (6H).

Molecule A10

A solution of molecule 24 (4.0 g, 3.05 mmol) in ethylenediamine (30 mL) is heated at 50° C. overnight. The reaction medium is then diluted with methyl-tetrahydrofuran then the organic phase is washed 4 times with a saturated NaCl solution (4×30 mL) then 2 times with water (2×50 mL) before being dried over Na$_2$SO$_4$ and concentrated under reduced pressure. The residue is solubilized in acetonitrile under reflux for 30 min then the solution is cooled to ambient temperature under stirring overnight. The white precipitate is then retrieved by filtering under vacuum, washed with cold acetonitrile (2×20 mL) then dried under vacuum.

Yield: 3.0 g (74%)

$^1$H NMR (CDCl$_3$, ppm): 0.87 (12H); 1.09-2.37 (84H); 2.74-4.56 (25H); 6.85-8.00 (7H).

LC/MS (ESI): 1338.0 (calculated ([M+H]$^+$): 1338.0).

Example A11: Molecule A11

Molecule 25: Product Obtained by Reacting Molecule 13 and Lauric Acid.

By means of a similar method to that used for molecule 5 applied to molecule 13 (28 mmol) and lauric acid (28.04 g, 140 mmol) in DMF (330 mL), molecule 25 is obtained.

Molecule A11

By means of a similar method to that used for molecule 8 applied to molecule 25, a white solid of molecule A11 is obtained after recrystallization in acetonitrile.

Yield: 13.9 g (56% in 6 stages)

$^1$H NMR (DMSO-d6, ppm): 0.85 (6H); 1.05-1.61 (60H); 1.62-1.75 (2H); 1.78-1.91 (2H); 2.04-2.27 (8H); 2.96-3.06 (2H); 4.08-4.13 (1H); 4.17-4.22 (1H); 4.27-4.34 (1H); 7.82 (1H); 7.86 (1H); 7.90 (1H); 8.03 (1H); 12.54 (1H).

LC/MS (ESI+): 881.7 (calculated ([M+H]$^+$): 881.7).

Example A12: Molecule A12

Molecule 26: Product Obtained by Reacting Molecule 13 and Fmoc-Glu(OtBu)-OH.

By means of a similar method to that used for molecule 5 applied to molecule 13 (9.92 mmol) and to Fmoc-Glu (OtBu)-OH (21.10 g, 49.60 mmol) in N-methyl-2-pyrrolidone (NMP, 120 mL), molecule 26 is obtained.

Molecule 27: Product Obtained by Reacting Molecule 26 and an 80:20 NMP/Piperidine Mixture.

By means of a similar method to that used for molecule 4 applied to molecule 26, using NMP instead of DMF, molecule 27 is obtained.

Molecule 28: Product Obtained by Reacting Molecule 27 and Fmoc-Glu(OtBu)-OH.

By means of a similar method to that used for molecule 26 applied to molecule 27 and to Fmoc-Glu(OtBu)-OH (21.10 g, 49.60 mmol), molecule 28 is obtained.

Molecule 29: Product Obtained by Reacting Molecule 28 and an 80:20 NMP/Piperidine Mixture.

By means of a similar method to that used for molecule 27 applied to molecule 28, molecule 29 is obtained.

Molecule 30: Product Obtained by Reacting Molecule 29 and Molecule A1.

By means of a similar method to that used for molecule 26 applied to molecule 29 (4.96 mmol) and to molecule A1 (8.07 g, 24.80 mmol), molecule 30 is obtained.

Molecule A12

By means of a similar method to that used for molecule 8 applied to molecule 30, a white solid of molecule A12 is obtained after purification by flash chromatography (DCM, MeOH).

Yield: 4.6 g (50% in 10 stages)

$^1$H NMR (CD$_3$OD, ppm): 0.90 (6H); 1.22-2.53 (140H); 3.12-3.25 (2H); 3.43-3.80 (4H); 4.17-4.54 (9H).

LC/MS (ESI+): 1894.5 (calculated ([M+Na]$^+$): 1894.2).

Example A14: Molecule A14

Molecule 33: Product Obtained by Reacting N-☐-Boc-L-Lysine and Palmitoyl Chloride By means of a similar method to that used for the preparation of molecule A1 applied to N-☐-Boc-L-Lysine (53.76 g, 218.28 mmol) and to palmitoyl chloride (50.00 g, 181.90 mmol), a white solid of molecule 33 is obtained after recrystallizing 2 times in acetonitrile and purification by flash chromatography (eluent: dichloromethane, methanol).

Yield: 49.10 g (70%)

$^1$H NMR (DMSO-d$_6$, ppm): 0.85 (3H); 1.09-1.66 (32H); 1.37 (9H); 2.01 (2H); 2.93-3.06 (2H); 3.78-3.85 (1H); 6.61-6.68 (0.2H); 6.96-6.98 (0.8H); 7.66-7.75 (1H); 12.38 (1H).

LC/MS (ESI): 385.1 (calculated ([M-Boc+H]$^+$): 385.3).

Molecule 34: Product Obtained by Reacting Molecule 33 and Methyl Iodide.

To a solution of molecule 33 (23.40 g, 48.28 mmol) in DMF (200 mL) at ambient temperature are added K$_2$CO$_3$ (10.01 g, 72.41 mmol) followed by methyl iodide (5.96 mL, 98.55 mmol). The medium is stirred for 48 h. Water (350 mL) is added and the suspension is stirred for 15 min. The latter is then filtered on a sintered filter and the solid obtained is rinsed with water (2×250 mL) and dried under vacuum. The solid is then solubilized in DCM (300 mL). The solution is washed with water (200 mL) then with an aqueous solution saturated with NaCl (200 mL), dried over Na$_2$SO$_4$, filtered and concentrated under reduced pressure. A white solid of molecule 34 is obtained after recrystallization in acetonitrile.

Yield: 19.22 g (80%)

$^1$H NMR (CDCl$_3$, ppm): 0.87 (3H); 1.06-2.23 (34H); 1.43 (9H); 3.09-3.33 (2H); 3.72 (3H); 3.94-4.35 (1H); 4.69-5.23 (1H); 5.33-5.75 (1H).

LC/MS (ESI): 543.3 (calculated ([M−H+HCOOH]$^-$): 543.4).

Molecule 35: Product Obtained by Hydrolyzing Molecule 34 with Hydrochloric Acid

By means of a similar method to that used for the preparation of molecule A5 applied to molecule 34 in solution in a 1:1 DCM/methanol mixture (385 mL), a white solid of molecule 35 is obtained after concentration under reduced pressure and co-evaporation with DCM followed by methanol.

Yield: 16.73 g (99%)

$^1$H NMR (DMSO-d$_6$, ppm): 0.85 (3H); 1.08-1.50 (30H); 1.67-1.84 (2H); 2.03 (2H); 2.94-3.13 (2H); 3.74 (3H); 3.92-4.01 (1H); 7.77-7.87 (1H); 8.25-8.73 (3H).

LC/MS (ESI): 399.2 (calculated ([M+H]$^+$): 399.4).

Molecule A14

To a suspension of molecule 35 (14.70 g, 33.79 mmol) in a mixture of methyl-THF (338 mL) and DMF (30 mL) are added successively DIPEA (17.70 mL, 101.40 mmol) followed by a solution of succinic anhydride (5.07 g, 50.68 mmol) in THF (60 mL). The medium is stirred for 4 h at ambient temperature. Methyl-THF (100 mL) is added and the organic phase is washed with a 5% HCl aqueous solution (300 mL). The aqueous phase is extracted with methyl-DCM (2×150 mL). The combined organic phases are washed with water (2×150 mL) then with an aqueous solution saturated with NaCl (150 mL), dried over Na$_2$SO$_4$, filtered and concentrated under reduced pressure. The crude product is purified by flash chromatography (eluent: DCM, methanol) then solubilized in methyl-THF. The purified product is then suspended in water. The suspension is stirred by sonication for 20 min followed by magnetic stirring for 30 min. A white solid of molecule A14 is obtained after filtration and drying under reduced pressure.

Yield: 12.99 g (77%)

$^1$H NMR (DMSO-d$_6$, ppm): 0.85 (3H); 1.08-1.71 (32H); 2.02 (2H); 2.29-2.45 (4H); 2.94-3.04 (2H); 3.61 (3H); 4.14-4.22 (1H); 7.70 (1H); 8.20 (1H); 12.04 (1H).

LC/MS (ESI): 499.3 (calculated ([M+H]$^+$): 499.4).

Example A15: Molecule A15

Molecule 36: Product Obtained by Coupling L-Proline and Palmitoyl Chloride

By means of a similar method to that used for the preparation of molecule A1 applied to L-proline (38.05 g, 906.00 mmol) and to palmitoyl chloride (14.01 g, 350.16 mmol), a white solid of molecule 36 is obtained.

Yield: 47.39 g (96%)

$^1$H NMR (CDCl$_3$, ppm): 0.88 (3H); 1.19-1.45 (24H); 1.58-1.74 (2H); 1.88-2.14 (3H); 2.15-2.54 (3H); 3.47 (1H); 3.58 (1H); 4.41 (0.1H); 4.61 (0.9H) 6.60-8.60 (1H).

LC/MS (ESI): 354.5 (calculated ([M+H]$^+$): 354.3).

Molecule 37: Product Obtained by Reacting Molecule 36 and N-Bocethylenediamine.

By means of a similar method to that used for molecule 9 applied to molecule 36 (75.1 g, 212.4 mmol), a white solid of molecule 37 is obtained after trituration in diisopropyl-ether (3×400 mL) and drying under vacuum at 40° C.

Yield: 90.4 g (86%).

$^1$H NMR (CDCl$_3$, ppm): 0.88 (3H); 1.20-1.37 (24H); 1.44 (9H); 1.54-1.70 (2H); 1.79-1.92 (1H); 1.92-2.04 (1H); 2.03-2.17 (1H); 2.17-2.44 (3H); 3.14-3.36 (4H); 3.43 (1H); 3.56 (1H); 4.29 (0.1 H); 4.51 (0.9 H); 4.82 (0.1H); 5.02 (0.9H); 6.84 (0.1H); 7.22 (0.9H).

Molecule 38: Product Obtained by Hydrolyzing Molecule 37 with Hydrochloric Acid

By means of a similar method to that used for the preparation of molecule A5 applied to molecule 37 (38.17 g, 76.99 mmol), a white solid of molecule 38 is obtained.

$^1$H NMR (CDCl$_3$, ppm): 0.88 (3H); 1.07-1.40 (24H); 1.49-1.63 (2H); 1.77-2.18 (4H); 2.18-2.45 (2H); 3.14-3.32 (2H); 3.42-3.63 (2H); 3.63-3.84 (2H); 4.37 (0.1H); 4.48 (0.9H); 6.81-8.81 (4H).

LC/MS (ESI): 396.5; (calculated ([M+H]$^+$): 396.4).

Molecule A15

By means of a similar method to that used for the preparation of molecule A14 applied to molecule 38 (10.00 g, 253.00 mmol), a white solid of molecule A15 is obtained.

Yield: 10.00 g (80%)

$^1$H NMR (DMSO, ppm): 0.85 (3H); 1.07-1.51 (26H); 1.69-2.02 (4H); 2.08-2.53 (6H); 3.01-3.18 (4H); 3.39-3.58

(2H); 4.13-4.18 (0.7H); 4.23-4.27 (0.3H); 7.70-7.78 (1.4H); 7.81-7.86 (0.3H); 8.00-8.04 (0.3H); 12.08 (1H).
LC/MS (ESI): 496.3 (calculated ([M+H]$^+$): 496.4).

Example A16: Molecule A16

Molecule 39: Product Obtained by Reacting Molecule 36 and Boc-1-amino-4,7,10-trioxa-13-tridecane Amine.

By means of a similar method to that used for the preparation of molecule 9 applied to molecule 36 (17.00 g, 48.08 mmol) and to Boc-1-amino-4,7,10-trioxa-13-tridecane amine (18.49 g, 57.70 mmol), a pale yellow oil of molecule 39 is obtained.

Yield: 31.11 g (98%)
$^1$H NMR (DMSO-d$_6$, ppm): 0.85 (3H); 1.17-1.31 (24H); 1.37 (9H); 1.41-1.51 (2H); 1.54-1.67 (4H); 1.69-2.02 (4H); 2.08-2.29 (2H); 2.91-3.00 (2H); 3.01-3.17 (2H); 3.31-3.58 (14H); 4.20 (0.65H); 4.26 (0.35H); 6.29-6.82 (1H); 7.68 (0.65H); 8.02 (0.35H).
LC/MS (ESI): 656.4 (calculated ([M+H]$^+$): 656.5).

Molecule 40: Product Obtained by Hydrolyzing Molecule 39 with Hydrochloric Acid

By means of a similar method to that used for the preparation of molecule A5 applied to molecule 39 (31.11 g, 47.43 mmol), a yellow wax of molecule 40 is obtained.

Yield: 27 g (97%)
$^1$H NMR (DMSO-d$_6$, ppm): 0.85 (3H); 1.18-1.31 (24H); 1.40-1.51 (2H); 1.55-1.67 (2H); 1.70-2.04 (6H); 2.09-2.30 (2H); 2.78-2.89 (2H); 2.99-3.18 (2H); 3.33-3.58 (14H); 4.19 (0.65H); 4.27 (0.35H); 7.55-8.14 (4H).
LC/MS (ESI): 556.3 (calculated ([M+H]$^+$): 556.5).

Molecule A16

Molecule 40 (26.40 g, 44.50 mmol) in hydrochloride form is solubilized in a mixture of DCM (350 mL) and an aqueous solution of NaHCO$_3$ (350 mL). The organic phase is separated and the aqueous phase is extracted with DCM (2×150 mL). The organic phases are combined dried over Na$_2$SO$_4$, filtered and concentrated under reduced pressure to produce a colorless oil. By means of a similar method to that used for the preparation of molecule A14, a yellow resin of molecule A16 is obtained after purification by flash chromatography (eluent: DCM, methanol).

Yield: 19.93 g (68%)
$^1$H NMR (DMSO-d$_6$, ppm): 0.85 (3H); 1.18-1.30 (24H); 1.40-1.51 (2H); 1.55-1.67 (4H); 1.70-2.02 (4H); 2.07-2.45 (6H); 2.99-3.18 (4H); 3.33-3.57 (14H); 4.19 (0.65H); 4.26 (0.35H); 7.68 (0.65H); 7.78 (1H); 8.02 (0.35H); 12.03 (1H).
LC/MS (ESI): 656.3 (calculated ([M+H]$^+$): 656.5).

Example A17: Molecule A17

Molecule 41: Product Obtained by Solid Phase Peptide Synthesis (SPPS)

Molecule 41 is obtained by means of the conventional solid phase peptide synthesis (SPPS) method on 2-chlorotrityl resin To a solution of 4,7,10-trioxa-1,13-tridecanediamine (TOTA, 76.73 mL, 350 mmol) in DCM (350 mL) is added DIPEA (60.96 mL, 350 mmol). This solution is then poured onto the 2-chlorotrityl resin (47.30 g, 0.74 mmol/g) previously washed with DCM in a reaction vessel suitable for SPPS. After 1.5 h of stirring at ambient temperature, methanol (26 mL) is added and the medium is stirred for 15 min. The resin is filtered, washed successively with DCM (3×350 mL), DMF (2×350 mL), DCM (2×350 mL), isopropanol (1×350 mL) and DCM (3×350 mL). The Q-methyl ester of N-Fmoc-L-glutamic acid (1.5 eq) followed by molecule 36 (1.5 eq) are coupled using the coupling agent 1-[bis(dimethylamino)methylene]-1H-1,2,3-triazolo[4,5-b]pyridinium 3-oxide hexafluorophosphate (HATU, 1.5 equivalents) and DIPEA (3 equivalents) in a 1:1 DCM/DMF mixture. A 1:1 DMF/morpholine mixture is used for the cleavage step of the Fmoc protecting group. The resin is washed with DCM, DMF and methanol after each coupling and deprotection step. The cleavage of the product from the resin is carried out using a 1:1 TFA/DCM mixture. The solvents are then evaporated under vacuum; the residue is solubilized in DCM (500 mL) and the organic phase is washed with a 5% Na$_2$CO$_3$ aqueous solution (500 mL). After drying over Na$_2$SO$_4$, the organic phase is filtered, concentrated under vacuum and a yellow oil of molecule 41 is obtained after drying under reduced pressure.

Yield: 15.95 g (65%)
1H NMR (DMSO-d6, ppm): 0.85 (3H); 1.16-1.31 (24H); 1.38-1.68 (6H); 1.68-2.37 (12H); 2.58 (2H); 3.01-3.17 (2H); 3.31-3.55 (14H); 3.58 (3H); 4.09-4.18 (0.7H); 4.18-4.29 (1H); 4.36-4.43 (0.3H); 7.62 (0.7H); 7.86 (0.7H); 7.98 (0.3H); 8.23 (0.3H).
LC/MS (ESI): 699.4 (calculated ([M+H]$^+$): 699.5).

Molecule A17

By means of a similar method to that used for the preparation of molecule A14 applied to molecule 41 (14.05 g, 20.10 mmol), a yellow resin of molecule A17 is obtained after purification by flash chromatography (eluent: DCM, methanol).

Yield: 7.70 g (48%)
1H NMR (DMSO-d6, ppm): 0.85 (3H); 1.17-1.31 (24H); 1.38-1.54 (2H); 1.54-1.68 (4H); 1.68-2.21 (7H); 2.21-2.36 (5H); 2.36-2.44 (2H); 3.01-3.16 (4H); 3.34-3.55 (14H); 3.57 (3H); 4.10-4.18 (0.7H); 4.18-4.30 (1H); 4.40 (0.3H); 7.60 (0.7H); 7.78 (1H); 7.85 (0.7H); 7.95 (0.3H); 8.22 (0.3H); 12.06 (1H).
LC/MS (ESI): 799.5 (calculated ([M+H]+): 799.5).

Example A18: Molecule A18

Molecule 42: Product Obtained by Reacting Molecule A1 and Boc-1-amino-4,7,10-trioxa-13-tridecane Amine.

By means of a similar method to that used for the preparation of molecule 18 applied to molecule A1 (44.80 g, 137.64 mmol) and to Boc-1-amino-4,7,10-trioxa-13-tridecane amine (52.92 g, 165.16 mmol), an orange oil of molecule 42 is obtained.

Yield: 85.63 g (99%)
1H NMR (CDCl$_3$, ppm): 0.87 (3H); 1.08-1.56 (20H); 1.43 (9H); 1.58-1.67 (2H); 1.70-2.00 (6H); 2.04-2.41 (4H); 3.16-3.77 (18H); 4.26-4.29 (0.2H); 4.50-4.54 (0.8H); 4.68-5.10 (1H); 6.74 (0.2H); 7.19 (0.8H).
LC/MS (ESI): 628.4; (calculated ([M+H]$^+$): 628.5).

Molecule 43: Product Obtained by Hydrolyzing Molecule 42 with Hydrochloric Acid

By means of a similar method to that used for the preparation of molecule A5 applied to molecule 42 (43.40 g, 69.12 mmol), a white solid of molecule 43 in hydrochloride salt form is obtained after trituration in diethylether, solubilizing the residue in water and freeze-drying.

Yield: 38.70 g (98%)
1H NMR (DMSO, ppm): 0.85 (3H); 1.07-1.38 (20H); 1.41-1.52 (2H); 1.55-1.66 (2H); 1.70-2.02 (6H); 2.08-2.30 (2H); 2.78-2.87 (2H); 3.00-3.16 (2H); 3.29-3.66 (14H); 4.16-4.22 (0.65 H); 4.25-4.30 (0.35H); 7.74 (0.65H); 7.86 (3H); 8.10 (0.35H).
LC/MS (ESI): 528.4; (calculated ([M+H]$^+$): 528.4).

Molecule A18

By means of a similar method to that used for the preparation of molecule A14 applied to molecule 43 (13.09 g, 24.8 mmol), a yellow resin of molecule A18 is obtained after purification by flash chromatography (eluent: DCM, methanol).

Yield: 8.53 g (55%)

1H NMR (DMSO-d6, ppm): 0.86 (3H); 1.10-1.39 (20H); 1.42-1.51 (2H); 1.57-1.67 (4H); 1.71-2.03 (4H); 2.09-2.32 (4H); 2.42 (2H); 3.01-3.17 (4H); 3.36-3.57 (14H); 4.18-4.21 (0.65H); 4.24-4.28 (0.35H); 7.69 (0.65H); 7.80 (1H); 8.03 (0.35H); 12.04 (1H).

LC/MS (ESI): 628.5 (calculated ([M+H]$^+$): 628.5).

Example A19: Molecule A19

Molecule 44: Product Obtained by SPPS

By means of a similar SPPS method to that used for the preparation of molecule 41 and applied to TOTA, to N-Fmoc-L-Leucine, N-Fmoc-L-proline and to myristic acid, an orange oil of molecule 44 is obtained.

Yield: 19.87 g (69%)

$^1$H NMR (CDCl$_3$, ppm): 0.72-1.06 (9H); 1.09-1.42 (20H); 1.42-2.40 (17H); 2.80 (2H); 3.22-3.81 (16H); 4.25-4.61 (2H); 6.56-7.23 (2H).

LC/MS (ESI): 641.5; (calculated ([M+H]$^+$): 641.5).

Molecule A19

After a similar method to that used for the preparation of molecule A14 applied to molecule 44 (13.09 g, 204.42 mmol), 4.81 g of the product obtained by purification by flash chromatography (eluent: DCM, methanol) is solubilized in a mixture of DCM (50 mL) and THF (5.5 mL) then washed with an aqueous solution saturated with NaCl (50 mL), a 0.1 N HCl aqueous solution (50 mL) and an aqueous solution saturated with NaCl (50 mL). The organic phase is dried over Na$_2$SO$_4$, filtered and concentrated under reduced pressure. A yellow oil of molecule A19 is obtained.

Yield: 4.20 g $^1$H NMR (DMSO-d$_6$, ppm): 0.72-1.02 (9H); 1.08-1.34 (20H); 1.34-2.23 (14H); 2.23-2.35 (3H); 2.42 (2H); 3.01-3.17 (4H); 3.17-3.66 (14H); 4.15-4.44 (2H); 7.53-8.23 (3H); 12.06 (1H).

LC/MS (ESI): 741.5; (calculated ([M+H]$^+$): 741.5).

Example A21: Molecule A21

Molecule 46: Product Obtained by SPPS

By means of a similar SPPS method to that used for the preparation of molecule 41 and applied to TOTA, to N-Fmoc-L-phenylalanine and to molecule A1, an orange oil of molecule 46 is obtained and used without purification.

Yield: 15.07 g (72%)

$^1$H NMR (CDCl$_3$, ppm): 0.87 (3H); 1.08-1.42 (20H); 1.42-1.62 (2H); 1.62-1.99 (7H); 1.99-2.26 (3H); 2.72 (2H); 2.86 (2H); 2.94-3.72 (18H); 4.20-4.72 (2H); 6.63-7.37 (7H).

LC/MS (ESI): 675.65; (calculated ([M+H]$^+$): 675.5).

Molecule A21

By means of a similar method to that used for the preparation of molecule A19 applied to molecule 46 (13.79 g, 20.43 mmol), a white solid of molecule A21 is obtained.

Yield: 7.56 g (48%)

$^1$H NMR (DMSO-d$_6$, ppm): 0.86 (3H); 1.02-1.42 (21H); 1.42-2.20 (10H); 2.23-2.38 (3H); 2.42 (2H); 2.78-3.18 (6H); 3.23-3.59 (14H); 4.12-4.58 (2H); 7.10-7.30 (5H); 7.53-8.33 (3H); 12.08 (1H).

LC/MS (ESI): 775.5; (calculated ([M+H]$^+$): 775.5).

Example A22: Molecule A22

By means of a similar method to that used for the preparation of molecule A14 applied to molecule A6 (22.15 g, 43.19 mmol), a yellow oil of molecule A22 is obtained.

Yield: 25.19 g (95%)

$^1$H NMR (DMSO-d$_6$, ppm): 0.42-1.51 (33H); 1.51-2.05 (8H); 2.29 (2H); 2.41 (2H); 3.07 (4H); 3.38 (4H); 3.43-3.54 (8H); 7.72 (1H); 7.79 (1H); 12.03 (1H).

LC/MS (ESI): 613.5 (calculated ([M+H]$^+$): 613.5).

Example A23: Molecule A23

Molecule 47: Product Obtained by Hydrogenating Phytol.

To a solution of phytol (30.00 g, 101.20 mmol) in THF (450 mL) under argon is added platinum dioxide (PtO$_2$, 1.15 g, 6.61 mmol). The medium is placed under 1 bar of dihydrogen then stirred for 4 h at ambient temperature. After filtering on celite by rinsing with THF, a black oil of molecule 47 is obtained after concentration under reduced pressure.

Yield: 29.00 g (96%)

$^1$H NMR (CDCl$_3$, ppm): 0.84 (6H); 0.86 (6H); 0.89 (3H); 1.00-1.46 (22H); 1.46-1.68 (3H); 3.61-3.73 (2H).

Molecule 48: Product Obtained by Oxidizing Molecule 47

To a solution of molecule 47 (29.0 g, 97.13 mmol) in a dichloroethane/water mixture (485 mL/388 mL) are added successively tetrabutylammonium bromide (16.90 g, 52.45 mmol), acetic acid (150 mL, 2.62 mol) followed by KMnO$_4$ (46.05 g, 291.40 mmol) in small fractions while maintaining the temperature from 16 to 19° C. The reaction medium is then stirred for 4.5 h under reflux, cooled to 10° C. then acidified to pH 1 with a 6 N HCl solution (20 mL). Na$_2$SO$_3$ (53.90 g) is added progressively while maintaining the temperature at 10° C. and the medium is stirred until completely discolored. Water (200 mL) is added, the phases are separated and the aqueous phase is extracted with DCM (2×400 mL). The combined organic phases are washed with a 10% HCl aqueous solution (20 mL), water (2×200 mL), an aqueous solution saturated with NaCl (200 mL), dried over Na$_2$SO$_4$, filtered and concentrated under reduced pressure. A yellow oil of molecule 48 is obtained after purification by flash chromatography (eluent: cyclohexane, AcOEt).

Yield: 28.70 g (94%)

$^1$H NMR (CDCl$_3$, ppm): 0.84 (6H); 0.86 (6H); 0.97 (3H); 1.00-1.41 (20H); 1.52 (1H); 1.96 (1H); 2.14 (1H); 2.35 (1H); 11.31 (1H).

LC/MS (ESI): 311.1 (calculated ([M−H]$^-$): 311.3).

Molecule 49: Product Obtained by Coupling Molecule 48 and Methyl L-Prolinate.

By means of a similar method to that used for the preparation of molecule 9 applied to molecule 48 (18.00 g, 57.59 mmol) and to methyl L-prolinate hydrochloride (14.31 g, 86.39 mmol) in DCM (380 mL), a yellow oil of molecule 49 is obtained after washing the organic phase with an aqueous solution saturated with NaHCO$_3$ (2×150 mL), a 10% HCl aqueous solution (2×150 mL), an aqueous solution saturated with NaCl (2×150 mL), followed by drying over Na$_2$SO$_4$, filtration and concentration under reduced pressure.

Yield: 23.20 g (95%)

$^1$H NMR (DMSO-d$_6$, ppm): 0.78-0.89 (15H); 0.97-1.43 (20H); 1.43-1.56 (1H); 1.70-1.96 (4H); 1.96-2.32 (3H); 3.33-3.56 (2H); 3.59 (0.6H); 3.67 (2.4H); 4.27 (0.8H); 4.57 (0.2H).

LC/MS (ESI): 424.4 (calculated ([M+H]$^+$): 424.4).

Molecule 50: Product Obtained by the Saponification of Molecule 49.

By means of a similar method to that used for the preparation of molecule 17 applied to molecule 49 (21.05 g, 49.68 mmol), a yellow oil of molecule 50 is obtained.

Yield: 20.40 g (99%)

$^1$H NMR (DMSO-$d_6$, ppm): 0.77-0.91 (15H); 0.97-1.43 (20H); 1.43-1.56 (1H); 1.67-1.96 (4H); 1.96-2.29 (3H); 3.26-3.56 (2H); 4.20 (0.8H); 4.41 (0.2H).

LC/MS (ESI): 410.3 (calculated ([M+H]$^+$): 410.4).

Molecule 51: Product Obtained by Coupling Molecule 50 and Boc-1-amino-4,7,10-trioxa-13-tridecane Amine.

By means of a similar method to that used for the preparation of molecule 9 applied to molecule 50 (8.95 g, 21.85 mmol) and to TOTA (8.40 g, 26.21 mmol), a colorless oil of molecule 51 is obtained after purification by flash chromatography (eluent: DCM, AcOEt, methanol).

Yield: 10.08 g (65%)

$^1$H NMR (DMSO-$d_6$, ppm): 0.78-0.89 (15H); 0.97-1.43 (29H); 1.43-1.55 (1H); 1.55-1.66 (4H); 1.71-2.30 (7H); 2.95 (2H); 3.00-3.19 (2H); 3.34-3.58 (14H); 4.17-4.29 (1H); 6.30-6.79 (1H); 7.67 (0.65H); 8.00 (0.35H).

LC/MS (ESI): 712.6 (calculated ([M+H]$^+$): 712.6).

Molecule 52: Product Obtained by Hydrolyzing Molecule 42 with Hydrochloric Acid

By means of a similar method to that used for the preparation of molecule A5 applied to molecule 51 (10.08 g, 14.16 mmol), the residue obtained after concentration under reduced pressure is solubilized in DCM (200 mL). The organic phase is washed with a 2 N NaOH aqueous solution (2×100 mL), dried over Na$_2$SO$_4$, filtered and concentrated under reduced pressure. A colorless oil of molecule 52 in neutral amine form is obtained.

Yield: 8.23 g (95%)

$^1$H NMR (DMSO-$d_6$, ppm): 0.78-0.89 (15H); 0.97-1.43 (20H); 1.43-1.69 (6H); 1.69-2.30 (8H); 2.56 (2H); 2.99-3.19 (2H); 3.31-3.58 (14H); 4.15-4.29 (1H); 7.70 (0.65H); 8.04 (0.35H).

LC/MS (ESI): 612.5 (calculated ([M+H]+): 612.5).

Molecule A23

By means of a similar method to that used for the preparation of molecule A14 applied to molecule 52 (15.40 g, 25.17 mmol), a yellow oil of molecule A23 is obtained.

Yield: 15.19 g (85%)

$^1$H NMR (DMSO-$d_6$, ppm): 0.76-0.91 (15H); 0.98-2.26 (32H); 2.29 (2H); 2.41 (2H); 2.98-3.18 (4H); 3.32-3.63 (14H); 4.15-4.29 (1H); 7.68 (0.7H); 7.78 (1H); 8.01 (0.3H); 12.02 (1H).

LC/MS (ESI): 712.5 (calculated ([M+H]$^+$): 712.5).

Example A26: Molecule A26

Molecule 55: Product Obtained by SPPS

Molecule 55 is obtained by means of the conventional solid phase peptide synthesis (SPPS) method on 2-chlorotrityl chloride (CTC) resin (47.56 g, 0.74 mmol/g). The grafting of the first amino acid Fmoc-Glu(OtBu)-OH (2.5 equivalents) is performed in DCM (10 V), in the presence of DIPEA (5.0 equivalents). The unreacted sites are capped with methanol (0.8 mL/g resin) at the end of the reaction.

The protected amino acids Fmoc-Glu(OtBu)-OH (1.5 equivalents (x2)) and molecule A1 (1.5 equivalents) are coupled in DMF (10 V), in the presence of HATU (1.0 equivalent with respect to the acid) and DIPEA (2.0 equivalents with respect to the acid).

The protecting groups Fmoc are removed using an 80:20 DMF/piperidine solution (10 V).

The product is cleaved from the resin using an 80:20 DCM/HFIP solution (10 V).

After concentration under reduced pressure, two co-evaporations are performed on the residue with dichloromethane followed by diisopropylether. The product is purified by silica gel chromatography (dichloromethane, methanol). A colorless gum of molecule 55 is obtained.

Yield: 21.4 g (69% in 8 stages)

$^1$H NMR (DMSO-d6, ppm): 0.85 (3H); 1.16-1.30 (20H); 1.34-1.41 (27H); 1.41-1.53 (2H); 1.67-2.33 (18H); 3.26-3.60 (2H); 4.09-4.44 (4H); 7.73 (0.65H); 7.85 (0.65H); 7.93-8.04 (1H); 8.17 (0.35H); 8.27 (0.35H); 12.64 (1H).

LC/MS (ESI+): 881.7 (calculated ([M+H]$^+$): 881.6).

Molecule 56: Product Obtained by Reacting Molecule 55 and 2-Phthalimido Ethylamine.

By means of a similar method to that used for the preparation of molecule 9 applied to molecule 55 (21.38 g, 24.26 mmol) and to 2-phthalimido ethylamine hydrochloride (HCl.PhthalEDA, 6.60 g, 29.12 mmol) in DCM and in the presence of DIPEA (5.07 mL, 29.12 mmol), a beige foam of molecule 56 is obtained without purification.

Yield: 25.56 g (100%)

$^1$H NMR (DMSO-d6, ppm): 0.85 (3H); 1.17-1.30 (20H); 1.34-1.41 (27H); 1.41-1.52 (2H); 1.56-2.32 (18H); 3.18-3.69 (6H); 4.01-4.43 (4H); 7.64-8.30 (8H).

LC/MS (ESI): 1053.8; (calculated ([M+H]$^+$): 1053.6).

Molecule A26

Molecule 56 (25.56 g, 24.26 mmol) is solubilized in a solution of 40% methylamine in MeOH (242.5 mL, 2.38 mol) at 4° C. then the mixture is stirred at ambient temperature for 5 h. Silica is added to the reaction medium then the latter is concentrated under reduced pressure. The residue is purified by silica gel chromatography (solid deposition, dichloromethane, methanol, NH$_3$) to produce molecule A26 in the form a pale yellow gum. This product is solubilized in DCM (250 mL) then the solution is washed with a 10% HCl aqueous solution. The aqueous phase is extracted with DCM (100 mL). The combined organic phases are dried over Na$_2$SO$_4$, filtered then concentrated under reduced pressure to produce the hydrochloride of molecule A26 in the form of a white solid.

Yield: 13.5 g (58%)

$^1$H NMR (DMSO-d6, ppm): 0.85 (3H); 1.18-1.30 (20H); 1.34-1.42 (27H); 1.42-1.53 (2H); 1.66-2.02 (9H); 2.02-2.39 (9H); 2.79-2.91 (2H); 3.25-3.64 (4H); 4.08-4.46 (4H); 7.68-8.37 (7H).

LC/MS (ESI): 923.8; (calculated ([M+H]$^+$): 923.6).

Example A27: Molecule A27

Molecule A27 is Obtained by Means of the Conventional Solid Phase Peptide Synthesis (SPPS) Method on 2-chlorotrityl Chloride (CTC) Resin (24.00 g, 1.37 mmol/g).

The grafting of the first amino acid Fmoc-6-aminohexanoic acid (1.5 equivalents) is performed in DCM (10 V), in the presence of DIPEA (2.5 equivalents). The unreacted sites are capped with methanol (0.8 mL/g resin) at the end of the reaction.

The protected amino acid Fmoc-Glu-OMe (1.5 equivalents) and palmitic acid (1.5 equivalents) are coupled in DMF (10 V), in the presence of HATU (1.0 equivalent with respect to the acid) and DIPEA (1.5 equivalents with respect to the acid).

The protecting groups Fmoc are removed using an 80:20 DMF/piperidine solution (10 V).

The product is cleaved from the resin using an 80:20 DCM/HFIP solution (10 V).

After concentration under reduced pressure, two co-evaporations are performed on the residue with dichloromethane followed by toluene. The product is purified by recrystallization in ethyl acetate. A white solid of molecule A27 is obtained.

Yield: 11.54 g (68% in 6 stages)

$^1$H NMR (CDCl$_3$, ppm): 0.88 (3H); 1.19-1.35 (24H); 1.35-1.44 (2H); 1.50-1.70 (6H); 1.91-2.01 (1H); 2.14-2.40 (7H); 3.14-3.34 (2H); 3.75 (3H); 4.51-4.59 (1H); 6.53 (1H); 6.70 (1H).

LC/MS (ESI+): 513.4 (calculated ([M+H]$^+$): 513.4).

Part B—Hydrophobic Co-Polyamino Acid Synthesis

| No | CO-POLYAMINO ACIDS BEARING CARBOXYLATE CHARGES AND HYDROPHOBIC RADICALS |
|---|---|
| B1 | 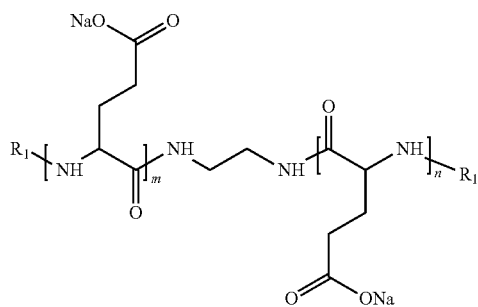<br>i = 0.050, DP (m + n) = 40<br>R$_1$ = H, pyroglutamate or<br>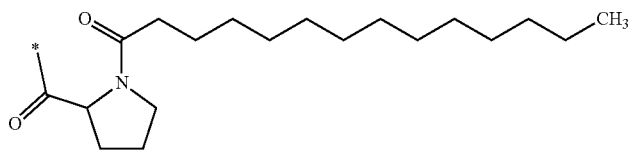 [SMILES: CCCCCCCCCCCCCC(=O)N1CCCC1C(C)=O] |
| B2 | 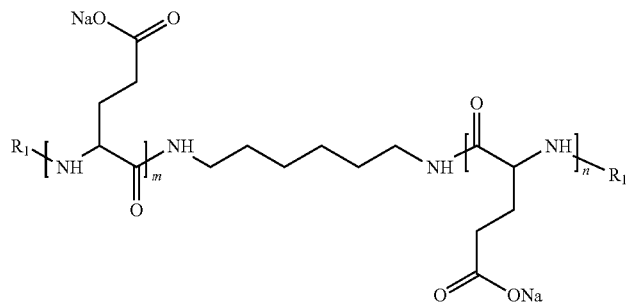<br>i = 0.0657, DP (m + n) = 30<br>R$_1$ = H, pyroglutamate or<br>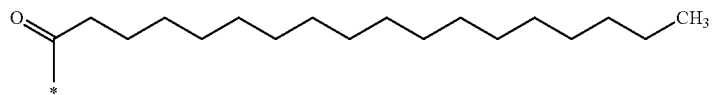 [SMILES: CCCCCCCCCCCCCCCCCC(C)=O] |
| B3 | 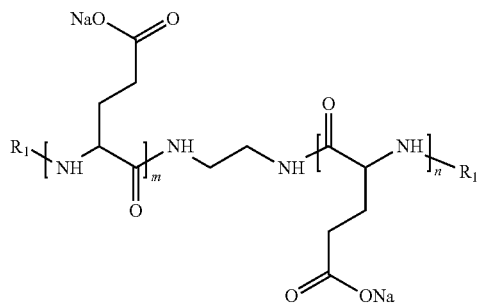<br>i = 0.0808, DP (m + n) = 24<br>R$_1$ = H, pyroglutamate or |

-continued
| No | CO-POLYAMINO ACIDS BEARING CARBOXYLATE CHARGES AND HYDROPHOBIC RADICALS |
|---|---|
|  | 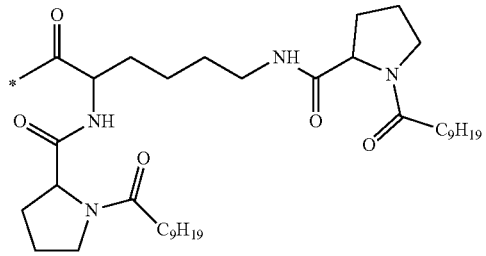 |
| B4 | 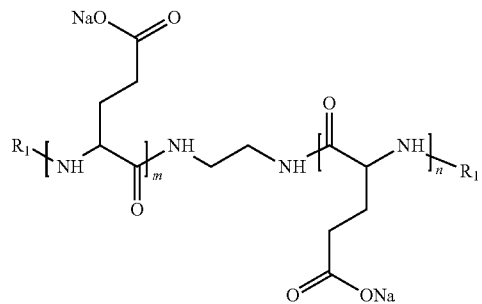<br>i = 0.134, DP (m + n) = 14<br>$R_1$ = H, pyroglutamate or<br>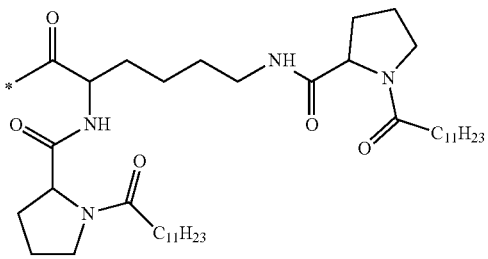 |
| B5 | 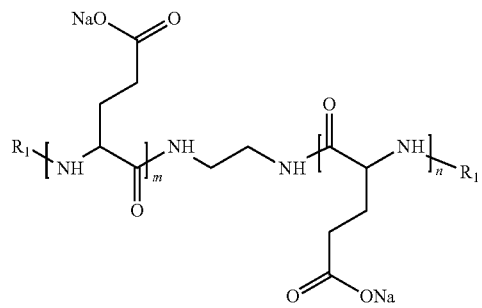<br>i = 0.077, DP (m + n) = 24<br>$R_1$ = H, pyroglutamate or<br>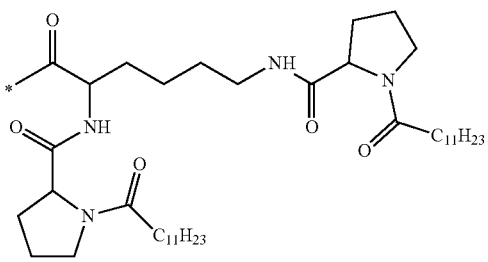 |

| No | CO-POLYAMINO ACIDS BEARING CARBOXYLATE CHARGES AND HYDROPHOBIC RADICALS |
|---|---|
| B6 | 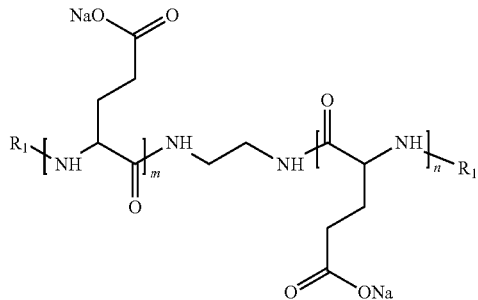<br>i = 0.0812, DP (m + n) = 24<br>R$_1$ = H, pyroglutamate or<br>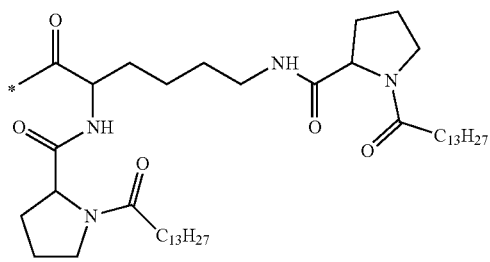 |
| B9 | 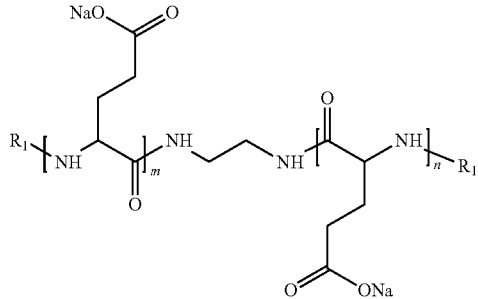<br>i = 0.0833, DP (m + n) = 24<br>R$_1$ = H, pyroglutamate or<br>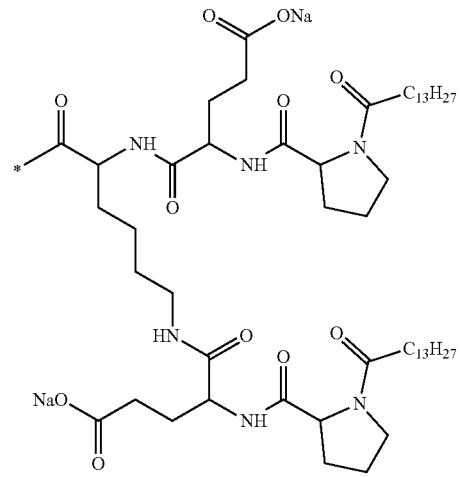 |

| No | CO-POLYAMINO ACIDS BEARING CARBOXYLATE CHARGES AND HYDROPHOBIC RADICALS |
|---|---|
| B13 | 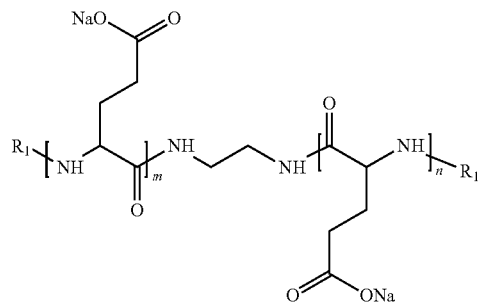 i = 0.079, DP (m + n) = 24<br>$R_1$ = H, pyroglutamate or<br>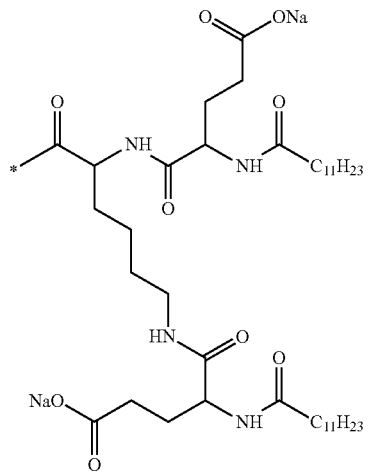 |
| B14 | 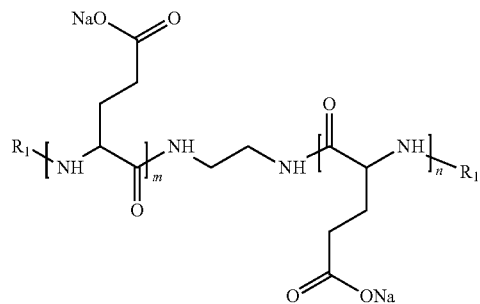 i = 0.072, DP (m + n) = 24<br>$R_1$ = H, pyroglutamate or |

-continued
| No | CO-POLYAMINO ACIDS BEARING CARBOXYLATE CHARGES AND HYDROPHOBIC RADICALS |
|---|---|
| | 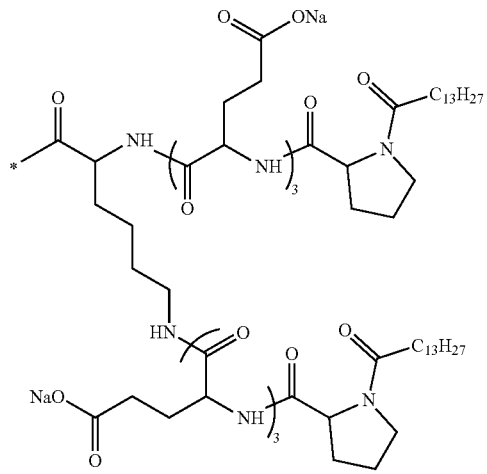 |
| B15 | 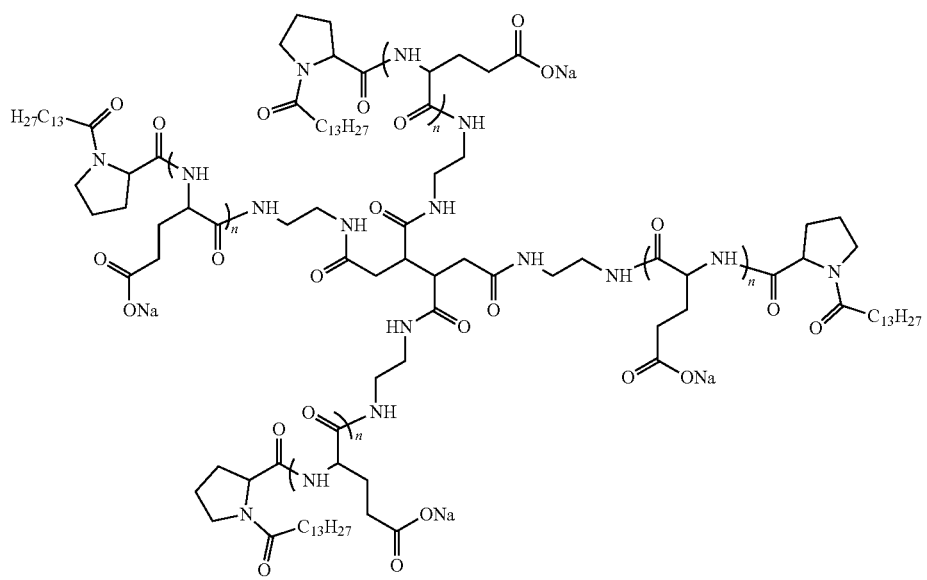
DP (n) = 5.5
i = 3.4 |
| B16 | 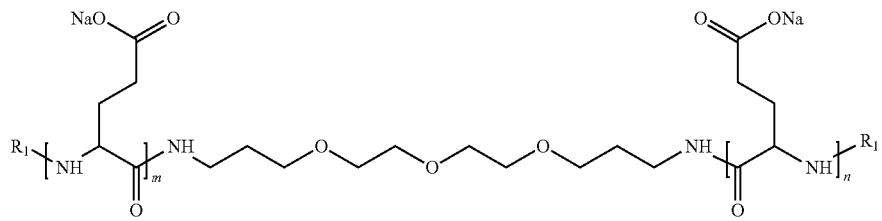
i = 0.078, DP (m + n) = 25
$R_1$ = H, pyroglutamate or |

| No | CO-POLYAMINO ACIDS BEARING CARBOXYLATE CHARGES AND HYDROPHOBIC RADICALS |
|---|---|
| | 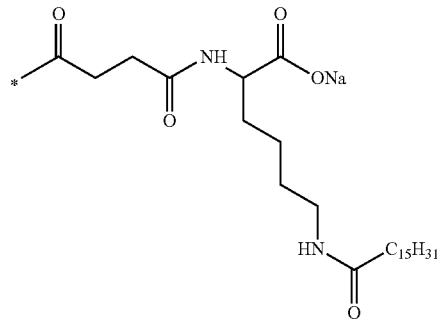 |
| B17 | 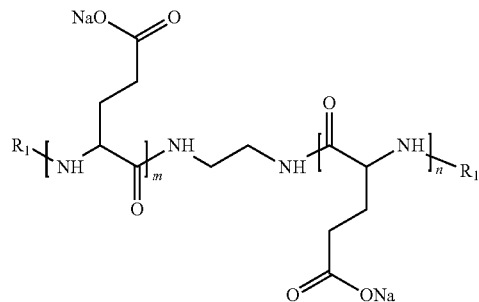
i = 0.048, DP (m + n) = 24
R₁ = H, pyroglutamate or
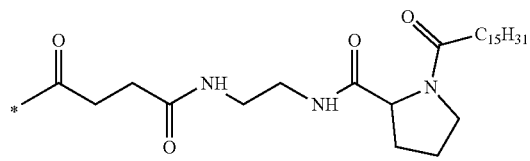 |
| B18 | 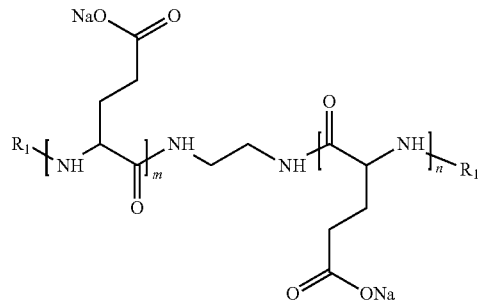
i = 0.075, DP (m + n) = 24
R₁ = H, pyroglutamate or
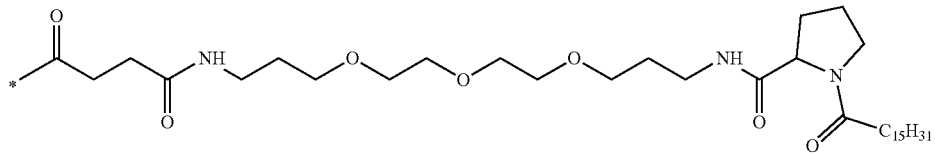 |

| No | CO-POLYAMINO ACIDS BEARING CARBOXYLATE CHARGES AND HYDROPHOBIC RADICALS |
|---|---|
| B19 | 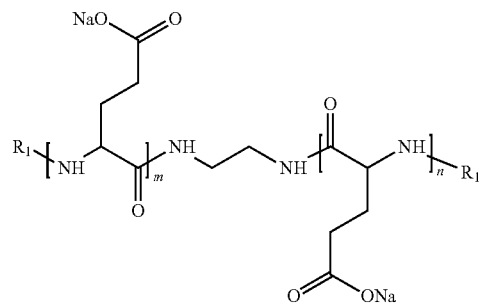 i = 0.066, DP (m + n) = 24<br>$R_1$ = H, pyroglutamate or<br>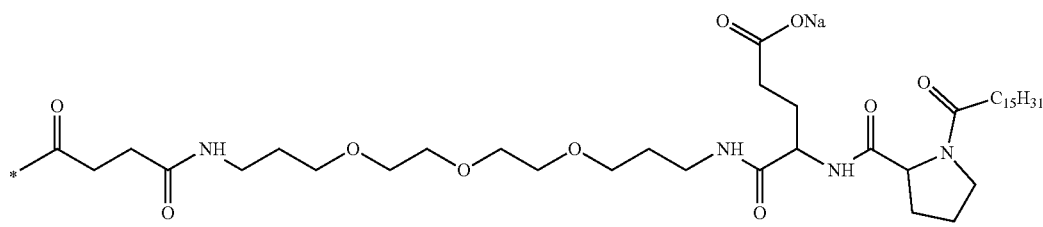 |
| B20 | 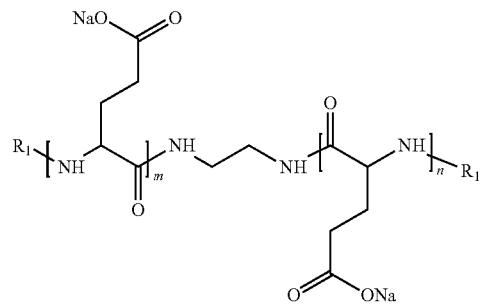 i = 0.075, DP (m + n) = 24<br>$R_1$ = H, pyroglutamate or<br>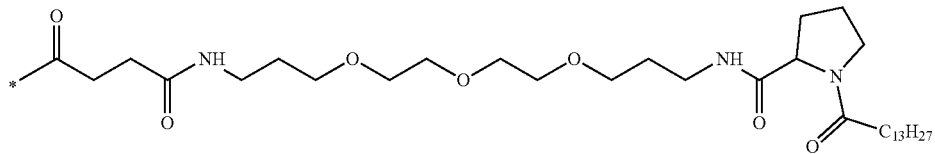 |
| B21 | 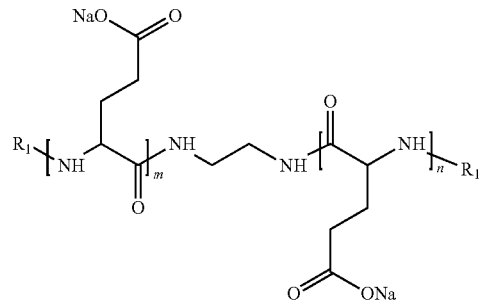 i = 0.077, DP (m + n) = 24<br>$R_1$ = H, pyroglutamate or |

| No | CO-POLYAMINO ACIDS BEARING CARBOXYLATE CHARGES AND HYDROPHOBIC RADICALS |
|---|---|
|  | 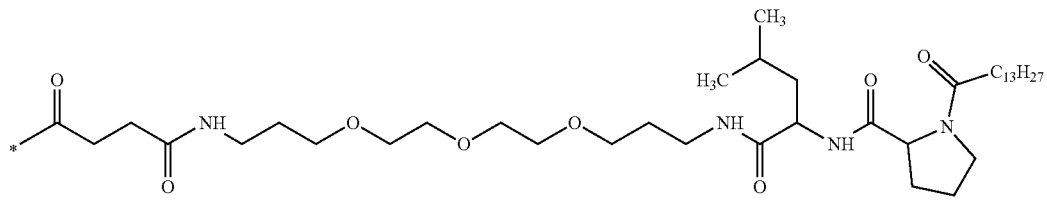 |
| B23 | 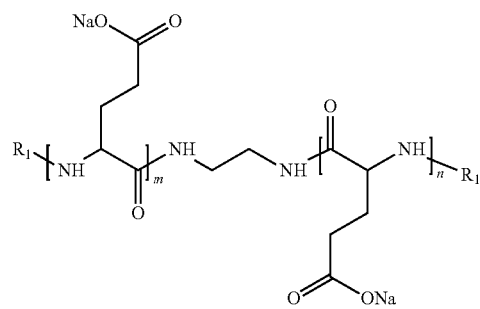
i = 0.080, DP (m + n) = 24
$R_1$ = H, pyroglutamate or
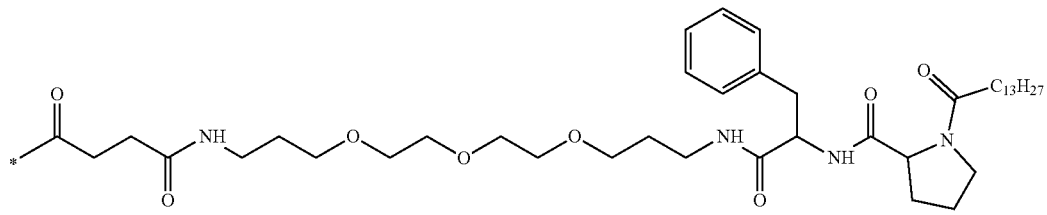 |
| B24 | 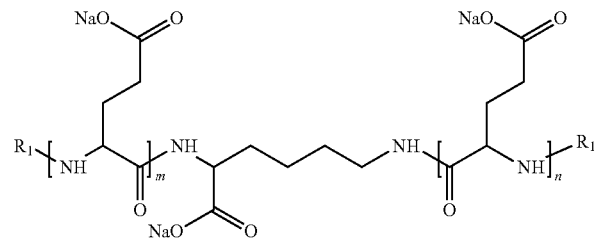
i = 0.143, DP (m + n) = 14
$R_1$ = H, pyroglutamate or
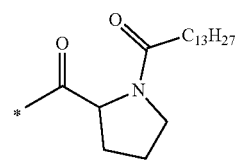 |

| No | CO-POLYAMINO ACIDS BEARING CARBOXYLATE CHARGES AND HYDROPHOBIC RADICALS |
|---|---|
| B25 | 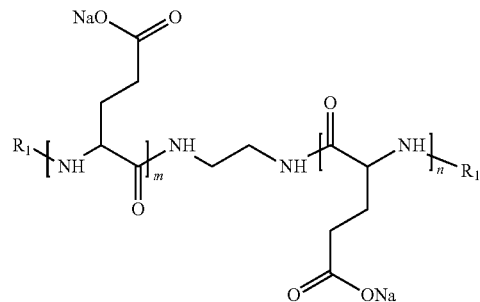<br>i = 0.079, DP (m + n) = 24<br>$R_1$ = H, pyroglutamate or<br>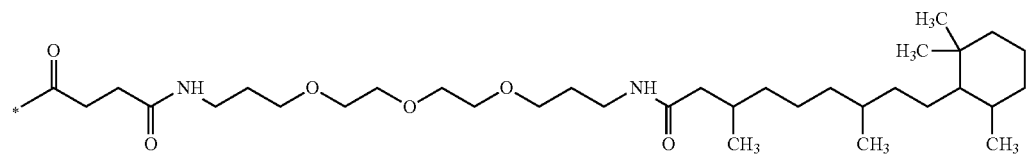 [SMILES: CC(=O)CCC(=O)NCCCOCCOCCOCCCNC(=O)CC(C)CCCC(C)CCC1C(C)CCCC1(C)C] |
| B26 | 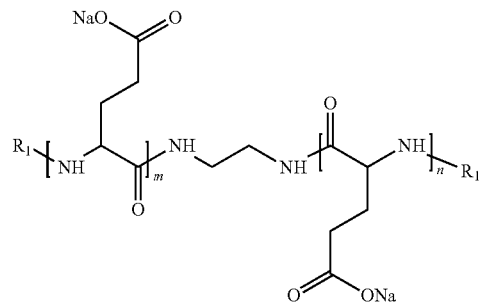<br>i = 0.073, DP (m + n) = 24<br>$R_1$ = H, pyroglutamate or<br>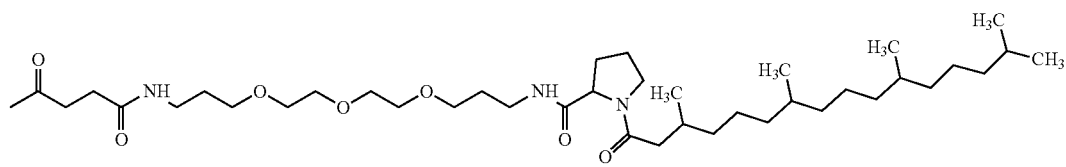 [SMILES: CC(=O)CCC(=O)NCCCOCCOCCOCCCNC(=O)C1CCCN1C(=O)CC(C)CCCC(C)CCCC(C)CCCC(C)C] |

-continued
| No | CO-POLYAMINO ACIDS BEARING CARBOXYLATE CHARGES AND HYDROPHOBIC RADICALS |
|---|---|
| B27 | 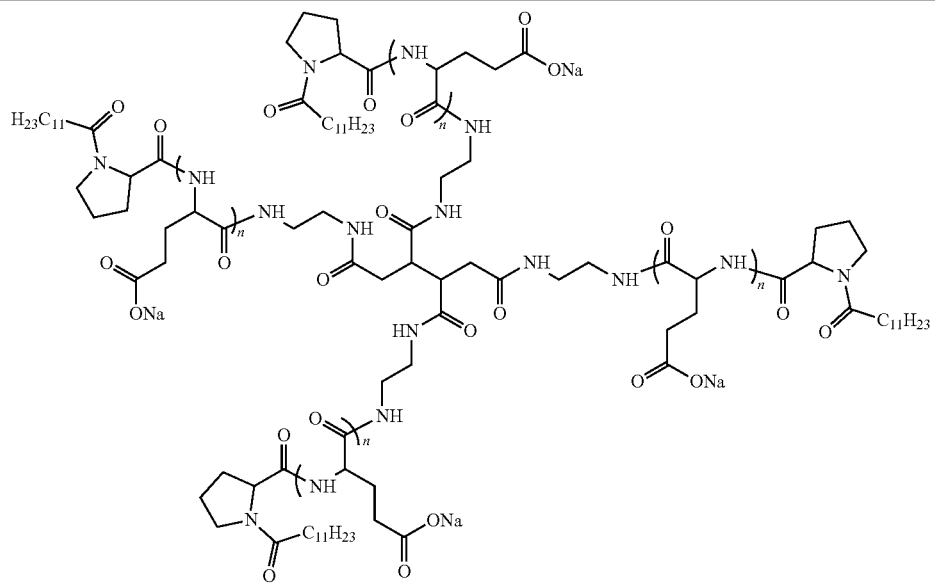DP (n) = 4.75<br>i = 3.7 |
| B28 | 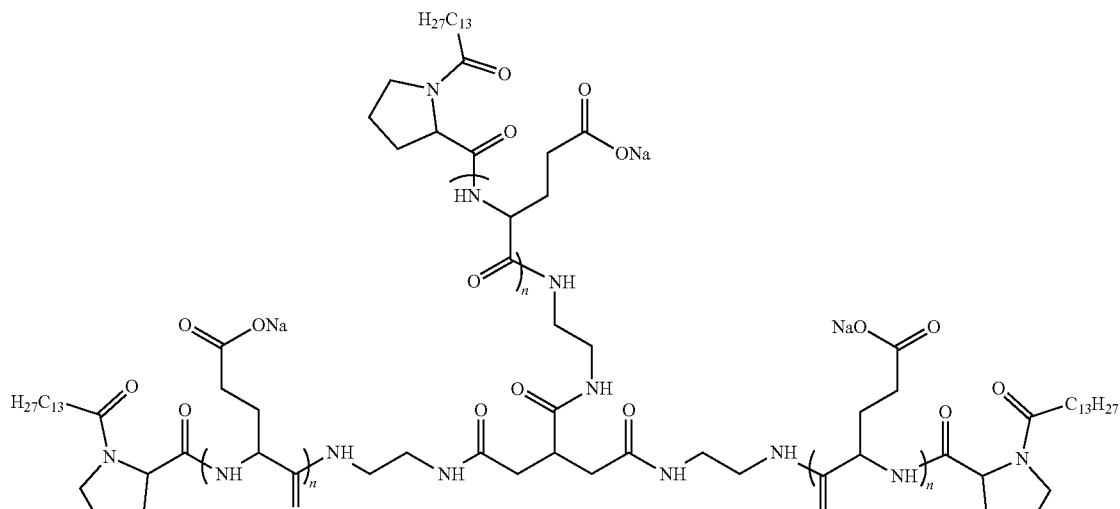DP (n) = 5.15<br>i = 3.0 |
| B29 | 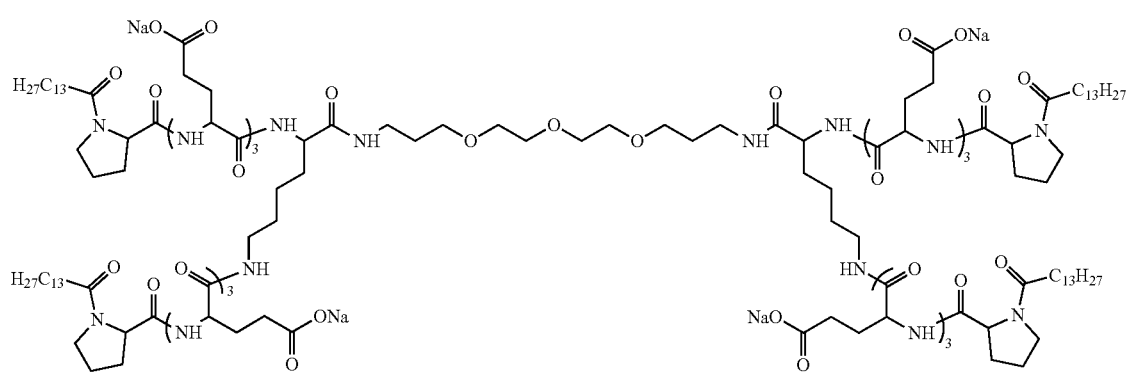 |

| No | CO-POLYAMINO ACIDS BEARING CARBOXYLATE CHARGES AND HYDROPHOBIC RADICALS |
|---|---|
| B30 | 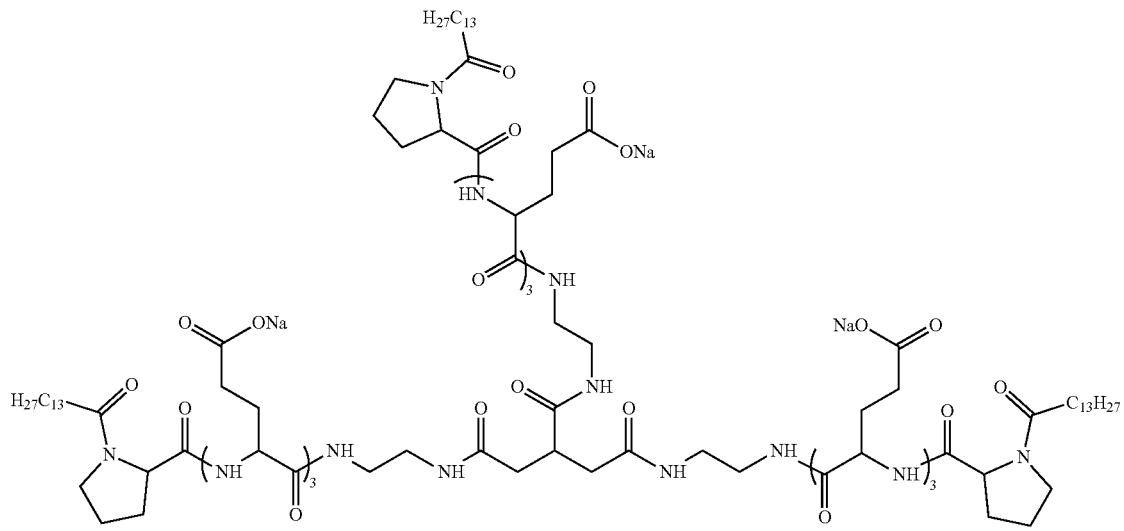 |
| B31 | 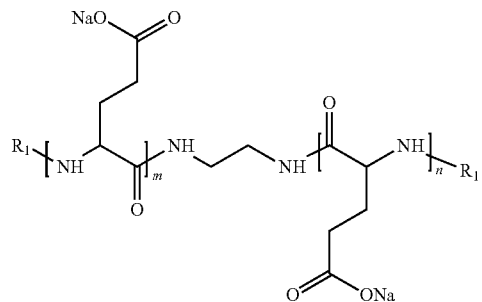<br>i = 0.075, DP (m + n) = 24<br>$R_1$ = H, pyroglutamate or<br>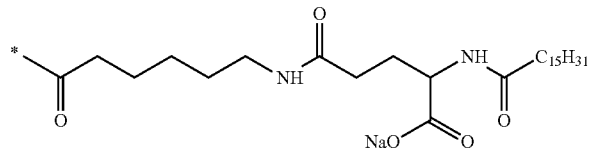 |

Example B1: Co-Polyamino Acid B1—Sodium poly-L-glutamate Modified at the Extremities Thereof by Molecule A1 and Having a Number Average Molar Mass (Mn) of 3600 g/mol Co-Polyamino Acid B1-1: poly-L-benzylglutamate Obtained from the Polymerization of γ-benzyl-L-glutamate N-carboxyanhydride Initiated by Ethylenediamine and Modified at the Extremities Thereof by Molecule A1.

In a previously oven-dried flask, γ-benzyl-L-glutamate N-carboxyanhydride (34.74 g, 132 mmol) is solubilized in anhydrous DMF (78 mL). The mixture is then stirred until complete dissolution, cooled to 0° C., then ethylene diamine (0.205 g, 3.41 mmol) is introduced rapidly and the medium is stirred at 0° C.

In parallel, molecule A1 (2.26 g, 6.94 mmol) is solubilized in DMF (44 mL), then NHS (0.82 g, 7.12 mmol) and DCC (1.47 g, 7.12 mmol) are added successively. After stirring overnight at ambient temperature, the heterogeneous mixture is filtered on a sintered filter. The filtrate is then added to the polymer solution kept at 0° C. After 24 h, the solution is placed at ambient temperature. After 6 h of stirring, the reaction medium is poured onto diisopropylether (IPE, 1.8 L). The precipitate is filtered on a sintered filter, washed with IPE (3×30 mL) and dried at 30° C. at reduced pressure.

Co-Polyamino Acid B1

Co-polyamino acid B1-1 is diluted in trifluoroacetic acid (TFA, 132 mL), then the solution is cooled to 4° C. A 33% HBr solution in acetic acid (92.5 mL, 0.528 mol) is then added dropwise. The mixture is stirred at ambient temperature for 2 h, then poured dropwise onto a 1:1 (v/v) mixture of diisopropylether and water under stirring (0.8 L). After 2 h of stirring, the heterogeneous mixture is left to stand overnight. The white precipitate is retrieved by filtration, washed with IPE (2×66 mL) then with water (2×66 mL). The solid obtained is then solubilized in water (690 mL) by adjusting the pH to 7 by adding an aqueous solution of 1 N sodium hydroxide. After solubilization, the theoretical concentration is adjusted to 20 g/L theoretical by adding water (310 mL), the solution is filtered on a 0.45 µm filter then purified by ultrafiltration against a 0.9% NaCl solution, followed by water until the conductimetry of the permeate is less than 50 µS/cm. The solution obtained is filtered on a 0.2 µm filter and stored at 2-8° C.

Dry extract: 24.3 mg/g
DP (estimated as per $^1$H NMR): 40
As per $^1$H NMR: i=0.050
The calculated average molar mass of co-polyamino acid B1 is 6719 g/mol.
HPLC-Organic SEC (PEG calibrator): Mn=3600 g/mol.

Example B2: Co-Polyamino Acid B2—Sodium poly-L-glutamate Modified at the Extremities Thereof by Stearic Acid and Having a Number Average Molar Mass (Mn) of 3400 g/mol Co-Polyamino Acid B2-1: poly-L-benzylglutamate Obtained from the Polymerization of γ-benzyl-L-glutamate N-carboxyanhydride Initiated by Hexamethylenediamine.

In a previously oven-dried flask, γ-benzyl-L-glutamate N-carboxyanhydride (30.0 g, 114 mmol) is solubilized in anhydrous DMF (67 mL). The mixture is then stirred until complete dissolution, cooled to 0° C., then hexamethylenediamine (0.442 g, 3.8 mmol) is introduced rapidly. After 23 h of stirring at 0° C., a 4 M HCl solution in dioxane (4.7 mL, 18.8 mmol) is added then the reaction medium is poured in 5 min onto a mixture of methanol (94 mL) and IPE (375 mL). The precipitate is filtered on a sintered filter, washed with IPE (2×70 mL) and dried at 30° C. at reduced pressure.

Co-Polyamino Acid B2-2: poly-L-benzylglutamate Modified at the Extremities Thereof by Stearic Acid.

To a solution of stearic acid (0.851 g, 2.99 mmol) in DMF (20 mL) at 0° C. are added successively HATU (1.484 g, 3.89 mmol) and DIPEA (1.166 g, 9.02 mmol). The solution is then introduced onto a solution of co-polyamino acid B2-1 (10.0 g) and triethylamine (TEA, 0.309 g, 3.04 mmol) in DMF (110 mL) at 0° C., and the medium is stirred for 18 h from 0° C. to ambient temperature. Dichloromethane (390 mL) is added, the organic phase is washed with 0.1 N HCl aqueous solution (3×190 mL), an aqueous solution saturated with NaHCO$_3$ (2×190 mL), an aqueous solution saturated with NaCl (2×190 mL) followed by water (190 mL). The medium is then poured onto IPE (1.4 L). The precipitate is filtered on a sintered filter, washed with IPE (2×100 mL) and dried at 30° C. at reduced pressure.

Co-Polyamino Acid B2

By means of a similar method to that used for the preparation of co-polyamino acid B1 applied to co-polyamino acid B2-2 (8.80 g, 36.5 mmol), a sodium poly-L-glutamate modified at the extremities thereof with stearic acid is obtained.

Dry extract: 17.9 mg/g
DP (estimated as per $^1$H NMR): 30
As per $^1$H NMR: i=0.0657
The calculated average molar mass of co-polyamino acid B2 is 5174 g/mol.
HPLC-Organic SEC (PEG calibrator): Mn=3400 g/mol.

Example B3: Co-Polyamino Acid B3—Sodium poly-L-glutamate Modified at the Extremities Thereof by Molecule A2 and Having a Number Average Molar Mass (Mn) of 3000 g/mol Co-Polyamino Acid B3-1: poly-L-benzylglutamate Obtained from the Polymerization of γ-benzyl-L-glutamate N-carboxyanhydride Initiated by Ethylenediamine.

By means of a similar method to that used for the preparation of co-polyamino acid B2-1 applied to ethylene diamine (0.765 g, 12.73 mmol) and to γ-benzyl-L-glutamate N-carboxyanhydride (80.0 g, 304 mmol), co-polyamino acid B3-1 is obtained.

Co-Polyamino Acid B3-2: poly-L-benzylglutamate Modified at the Extremities Thereof by Molecule A2.

By means of a similar method to that used for the preparation of co-polyamino acid B2-2 applied to co-polyamino acid B3-1 (30.0 g, 5.56 mmol) and to molecule A2 (7.94 g, 12.24 mmol), a poly-L-benzylglutamate modified at the extremities thereof with molecule A2 is obtained.

Co-Polyamino Acid B3

To a solution of co-polyamino acid B3-2 (36.6 g, 133.5 mmol) in N,N-dimethylacetamide (DMAc, 146 mL) is added 5% palladium on alumina (7.3 g), then the solution is placed at 60° C. at 10 bar hydrogen. After overnight, the reaction medium is filtered on a sintered filter then on a 0.2 µm PTFE filter. The filtrate is then placed under stirring before adding water (1.4 L) previously acidified to pH 2 with a 1 N HCl solution (14 mL) dropwise. After overnight, the precipitate is filtered on a sintered filter, washed with water (4×110 mL) and dried at 30° C. at reduced pressure.

The solid obtained is then solubilized in water (1.09 L) by adjusting the pH to 7 by adding an aqueous solution of 1 N sodium hydroxide (121 mL). After solubilization, the solution is basified by adding 1 N sodium hydroxide (26 mL) up to a pH of 12. After 2 h, the solution is neutralized by adding 1 N HCl solution (28 mL). The theoretical concentration is adjusted to 12 g/L theoretical by adding water (650 mL) and ethanol (1040 mL) then the solution is filtered on an R53SLP carbon filter (3M) at a rate of 12 mL/min, then on a 0.2 µm PES filter. The solution is then purified by ultrafiltration against a 0.9% NaCl solution, followed by water until the conductimetry of the permeate is less than 50 µS/cm. The solution obtained is filtered on a 0.2 µm filter and stored at 2-8° C.

Dry extract: 21.6 mg/g
DP (estimated as per $^1$H NMR): 24
As per $^1$H NMR: i=0.0808
The calculated average molar mass of co-polyamino acid B3 is 4948 g/mol.
HPLC-Organic SEC (PEG calibrator): Mn=3000 g/mol.

Example B4: Co-Polyamino Acid B4—Sodium poly-L-glutamate Modified at the Extremities Thereof by Molecule A3 and Having a Number Average Molar Mass (Mn) of 2500 g/mol Co-Polyamino Acid B4-1: poly-L-benzylglutamate Obtained from the Polymerization of γ-benzyl-L-glutamate N-carboxyanhydride Initiated by Ethylenediamine.

By means of a similar method to that used for the preparation of co-polyamino acid B2-1 applied to ethylene diamine (1.644 g, 27.35 mmol) and to γ-benzyl-L-glutamate N-carboxyanhydride (100.0 g, 380 mmol), co-polyamino acid B4-1 is obtained.

Co-Polyamino Acid B4-2: poly-L-benzylglutamate Modified at the Extremities Thereof by Molecule A3.

By means of a similar method to that used for the preparation of co-polyamino acid B2-2 applied to co-polyamino acid B4-1 (10.0 g, 3.12 mmol) and to molecule A3 (4.412 g, 6.26 mmol), a poly-L-benzylglutamate modified at the extremities thereof with molecule A3 is obtained.

Co-Polyamino Acid B4

By means of a similar method to that used for the preparation of co-polyamino acid B3 applied to co-polyamino acid B4-2 (12.0 g, 37.3 mmol), a sodium poly-L-glutamate modified at the extremities thereof with molecule A3 is obtained.

Dry extract: 21.7 mg/g
DP (estimated as per $^1$H NMR): 14
As per $^1$H NMR: i=0.134
The calculated average molar mass of co-polyamino acid B4 is 3464 g/mol.
HPLC-Organic SEC (PEG calibrator): Mn=2500 g/mol.

Example B5: Co-Polyamino Acid B5—Sodium poly-L-glutamate Modified at the Extremities Thereof by Molecule A3 and Having a Number Average Molar Mass (Mn) of 2800 g/mol Co-Polyamino Acid B5-1: poly-L-benzylglutamate Obtained from the Polymerization of γ-benzyl-L-glutamate N-carboxyanhydride Initiated by Ethylenediamine.

By means of a similar method to that used for the preparation of co-polyamino acid B2-1 applied to ethylene diamine (0.95 g, 15.83 mmol) and to γ-benzyl-L-glutamate N-carboxyanhydride (100.0 g, 380 mmol), co-polyamino acid B5-1 is obtained.

Co-Polyamino Acid B5-2: poly-L-benzylglutamate Modified at the Extremities Thereof by Molecule A3.

By means of a similar method to that used for the preparation of co-polyamino acid B2-2 applied to co-polyamino acid B5-1 (20.0 g, 3.71 mmol) and to molecule A3 (5.233 g, 7.42 mmol), a poly-L-benzylglutamate modified at the extremities thereof with molecule A3 is obtained.

Co-Polyamino Acid B5

By means of a similar method to that used for the preparation of co-polyamino acid B1 applied to co-polyamino acid B5-2 (15.6 g, 55.93 mmol), a sodium poly-L-glutamate modified at the extremities thereof with molecule A3 is obtained.

Dry extract: 27.4 mg/g
DP (estimated as per $^1$H NMR): 24
As per $^1$H NMR: i=0.077
The calculated average molar mass of co-polyamino acid B5 is 4956 g/mol.
HPLC-Organic SEC (PEG calibrator): Mn=2800 g/mol.

Example B6: Co-Polyamino Acid B6: Sodium poly-L-glutamate Modified at the Extremities Thereof by Molecule A4 and Having a Number Average Molar Mass (Mn) of 2900 g mol Co-Polyamino Acid B6-1: poly-L-benzylglutamate Obtained from the Polymerization of γ-benzyl-L-glutamate N-carboxyanhydride Initiated by Ethylenediamine.

By means of a similar method to that used for the preparation of co-polyamino acid B2-1 applied to ethylene diamine (0.951 g, 15.83 mmol) and to γ-benzyl-L-glutamate N-carboxyanhydride (100.0 g, 380 mmol), co-polyamino acid B6-1 is obtained.

Co-Polyamino Acid B6-2: poly-L-benzylglutamate Modified at the Extremities Thereof by Molecule A4.

By means of a similar method to that used for the preparation of co-polyamino acid B2-2 applied to co-polyamino acid B6-1 (20.0 g, 3.71 mmol) and to molecule A4 (6.649 g, 8.74 mmol), a poly-L-benzylglutamate modified at the extremities thereof with molecule A4 is obtained.

Co-Polyamino Acid B6

By means of a similar method to that used for the preparation of co-polyamino acid B1 applied to co-polyamino acid B6-2 (19.7 g, 69.47 mmol), a sodium poly-L-glutamate modified at the extremities thereof with molecule A4 is obtained.

Dry extract: 28.7 mg/g
DP (estimated as per $^1$H NMR): 24
As per $^1$H NMR: i=0.0812
The calculated average molar mass of co-polyamino acid B6 is 5135 g/mol.
HPLC-Organic SEC (PEG calibrator): Mn=2900 g/mol.

Example B9: Co-Polyamino Acid B9—Sodium poly-L-glutamate Modified at the Extremities Thereof by Molecule A7 Wherein the Side Chains are Deprotected and Having a Number Average Molar Mass (Mn) of 3200 g/mol Co-polyamino Acid B9-1: poly-L-benzylglutamate Obtained from the Polymerization of γ-benzyl-L-glutamate N-carboxyanhydride Initiated by Ethylenediamine.

By means of a similar method to that used for the preparation of co-polyamino acid B2-1 applied to ethylene diamine (0.96 g, 15.94 mmol) and to γ-benzyl-L-glutamate N-carboxyanhydride (100.0 g, 380 mmol), co-polyamino acid B9-1 is obtained.

Co-Polyamino Acid B9-2: poly-L-benzylglutamate Modified at the Extremities Thereof by Molecule A7.

By means of a similar method to that used for the preparation of co-polyamino acid B2-2 applied to co-polyamino acid B9-1 (25.0 g, 4.64 mmol) and to molecule A7 (10.49 g, 9.27 mmol), a poly-L-benzylglutamate modified at the extremities thereof with molecule A7 is obtained.

Co-Polyamino Acid B9-3: poly-L-benzylglutamate Modified at the Extremities Thereof by Molecule A7 Wherein the Side Chains are Deprotected.

Co-polyamino acid B9-2 (18.6 g) is solubilized in TFA (100 mL). After 2 h under stirring, the reaction medium is concentrated under reduced pressure.

Co-Polyamino Acid B9

By means of a similar method to that used for the preparation of co-polyamino acid B3 applied to co-polyamino acid B9-3 (18.0 g, 59.0 mmol), a sodium poly-L-glutamate modified at the extremities thereof with molecule A7 is obtained.

Dry extract: 21.8 mg/g
DP (estimated as per $^1$H NMR): 24
As per $^1$H NMR: i=0.0833
The calculated average molar mass of co-polyamino acid B9 is 5776 g/mol.
HPLC-Organic SEC (PEG calibrator): Mn=3200 g/mol.

Example B13: Co-Polyamino Acid B13—Sodium poly-L-glutamate Modified at the Extremities Thereof by Molecule all Wherein the Esters are Deprotected and Having a Number Average Molar Mass (Mn) of 3200 g/mol Co-Polyamino Acid B13-1: poly-L-benzylglutamate Obtained from the Polymerization of γ-benzyl-L-glutamate N-carboxyanhydride Initiated by Ethylenediamine.

By means of a similar method to that used for the preparation of co-polyamino acid B2-1 applied to ethylene diamine (4.76 g, 15.94 mmol) and to γ-benzyl-L-glutamate N-carboxyanhydride (500.0 g, 1900 mmol), co-polyamino acid B13-1 is obtained.

Co-Polyamino Acid B13-2: poly-L-benzylglutamate Modified at the Extremities Thereof by Molecule A11.

To a solution of co-polyamino acid B13-1 (12.0 g) in DMF (40 mL) at 0° C. are successively added a solution of molecule A11 (5.88 g, 6.67 mmol) in DMF (20 mL), N-2-hydroxypyridine oxide (HOPO, 0.82 g, 7.34 mmol), N-(3-dimethylaminopropyl)-N'-ethylcarbodiimide (EDC) (1.66 g, 8.68 mmol), followed by DIPEA (0.97 mL, 5.56 mmol). The reaction medium is stirred at 0° C. for 16 h and at 20° C. for 2 h. Dichloromethane (150 mL) is added and the organic phase is washed with a 0.1 N HCl aqueous solution (6×75 mL), dried over $Na_2SO_4$ then filtered. The organic phase is then poured onto IPE (600 mL), then left to stand for 18 h. The white precipitate is retrieved by filtration, washed with IPE (2×150 mL) then dried under reduced pressure at 30° C.

Co-Polyamino Acid B13-3: poly-L-benzylglutamate Modified at the Extremities Thereof by Molecule A11 Wherein the Esters are Deprotected Co-polyamino acid B13-2 is solubilized in TFA (60 mL), and the solution is stirred for 2 h at ambient temperature then is poured dropwise onto diisopropylether under stirring (600 mL). After 18 h, the white precipitate is retrieved by filtration, triturated with IPE and dried under reduced pressure.

Co-Polyamino Acid B13

By means of a similar method to that used for the preparation of co-polyamino acid B3 applied to co-polyamino acid B13-3 (14.5 g), a sodium poly-L-glutamate modified at the extremities thereof with molecule A11 wherein the esters are deprotected is obtained.

Dry extract: 18.0 mg/g

DP (estimated as per $^1$H NMR): 24

As per $^1$H NMR: i=0.079

The calculated average molar mass of co-polyamino acid B13 is 5194 g/mol.

HPLC-Organic SEC (PEG calibrator): Mn=3200 g/mol

Example B14: Co-Polyamino Acid B14—Sodium poly-L-glutamate Modified at the Extremities Thereof by Molecule A12 Wherein the Esters are Deprotected and Having a Number Average Molar Mass (Mn) of 3700 g/mol Co-Polyamino Acid B14-1: poly-L-benzylglutamate Obtained from the Polymerization of γ-benzyl-L-glutamate N-carboxyanhydride Initiated by Ethylenediamine.

By means of a similar method to that used for the preparation of co-polyamino acid B2-1 applied to ethylene diamine (4.76 g, 15.94 mmol) and to γ-benzyl-L-glutamate N-carboxyanhydride (500.0 g, 1900 mmol), co-polyamino acid B14-1 is obtained.

Co-Polyamino Acid B14-2: poly-L-benzylglutamate Modified at the Extremities Thereof by Molecule A12

By means of a similar method to that used for the preparation of co-polyamino acid B2-2 applied to molecule A12 (2.67 g, 1.43 mmol) and to co-polyamino acid B14-1 (3.5 g), a poly-L-benzylglutamate modified at the two extremities thereof with molecule A12 is obtained.

Co-Polyamino Acid B14-3: poly-L-benzylglutamate Modified at the Extremities Thereof by Molecule A12 Wherein the Esters are Deprotected By means of a similar method to that used for the preparation of co-polyamino acid B13-3 applied to co-polyamino acid B14-2, a poly-L-benzylglutamate modified at the two extremities thereof with molecule A12 wherein the esters are deprotected is obtained.

Co-Polyamino Acid B14

By means of a similar method to that used for the preparation of co-polyamino acid B3 applied to co-polyamino acid B14-3 (1.97 g), in a hydrogen atmosphere (1 atm, 48 h, 65° C.), a sodium poly-L-glutamate modified at the two extremities thereof with molecule A12 wherein the esters are deprotected is obtained.

Dry extract: 13.2 mg/g

DP (estimated as per $^1$H NMR): 24

As per $^1$H NMR: i=0.072

The calculated average molar mass of co-polyamino acid B14 is 6537 g/mol.

HPLC-Organic SEC (PEG calibrator): Mn=3700 g/mol

Example B15: Co-Polyamino Acid B15
—Butyltetracarboxylic Acid Substituted with Molecule A13 Wherein the Esters are Deprotected and Having a Number Average Molar Mass (Mn) of 2700 g/mol Molecule A13

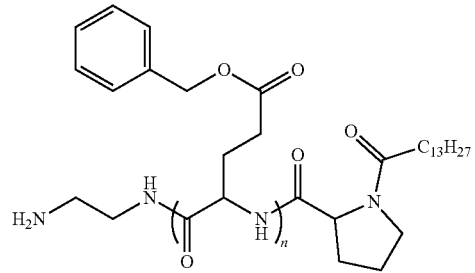

i = 0.182, DP (n) = 5.5

Molecule 31: Product Obtained by Polymerization of γ-benzyl-L-glutamate N-carboxyanhydride Initiated by N-Boc-ethylenediamine.

A solution of BocEDA (12.00 g, 74.9 mmol) in DMF (12 mL) is prepared. In a reaction vessel, γ-benzyl-L-glutamate N-carboxyanhydride (78.87 g, 300.0 mmol) is solubilized in DMF (165 mL) at 25° C. The mixture is then stirred until complete dissolution, cooled to −10° C., then the BocEDA solution is introduced rapidly. The reaction medium is stirred at 0° C. for 4 h then a solution of HCl in 1,4-dioxane (3.33 M, 19.8 mL, 65.34 mmol) is added. The reaction medium is stirred at ambient temperature then the solution is poured onto a solution of MeOH/IPE (245 mL/990 mL) cooled by an ice bath. After 62 h of stirring at ambient temperature, the white precipitate is filtered on a sintered filter, washed with IPE (2×160 mL) and dried at 30° C. at reduced pressure.

¹H NMR (DMSO-d6, ppm): 1.35 (9H); 1.70-2.10 (10H); 2.26-2.65 (10H); 2.85-3.18 (4H); 3.85 (1H); 4.14-4.42 (4H); 4.87-5.24 (10H); 6.34-6.86 (1H); 7.11-7.56 (25H); 7.90-8.44 (7H); 8.69 (1H).

DP (estimated as per ¹H NMR): 5.0

The calculated average molar mass of molecule 31 in hydrochloride salt form is 1292.9 g/mol.

Molecule 32: Product Obtained by Coupling Molecule 31 and Molecule A1.

Molecule 31 (10.0 g, 7.73 mmol) is solubilized in a mixture of DCM (90 mL) and DIPEA (1.585 g, 9.32 mmol) at 0° C. To this solution are added successively HOPO (1.242 g, 11.18 mmol), molecule A1 (3.335 g, 10.25 mmol) and EDC (2.141 g, 11.17 mmol). After stirring overnight, the reaction medium is washed twice with a 0.1 N HCl solution (2×100 mL), twice with a 5% $Na_2CO_3$ aqueous solution (2×100 mL) followed by a saturated NaCl solution (100 mL). The organic phase is dried over $Na_2SO_4$, filtered and concentrated under reduced pressure. The residue is solubilized in DCM (30 mL) and the solution is poured onto isopropyl alcohol (600 mL) under stirring at 0° C. The precipitate formed is retrieved by vacuum filtration then dried under vacuum at 30° C.

Yield: 7.58 g (62%)

¹H NMR ($CDC_3$, ppm): 0.87 (3H); 1.06-2.76 (58.6H); 3.06-4.45 (12.4H); 4.88-5.25 (10.8H); 5.72-8.40 (34.4H).

DP (estimated as per ¹H NMR): 5.4

The calculated average molar mass of molecule 32 in hydrochloride salt form is 1651.6 g/mol.

Molecule A13

After solubilizing molecule 32 (5.93 g, 3.59 mmol) in DCM (40 mL), the solution is cooled to 0° C. and TFA (40 mL) is added. The reaction medium is stirred at 0° C. for 3 h then is dry concentrated under reduced pressure at ambient temperature. The residue is taken up with DCM (120 mL) and washed with an aqueous carbonate buffer solution at pH 10.4 (3×240 mL) then by a 0.1 N HCl aqueous solution (2×240 mL). The organic solution is dried over $Na_2SO_4$, filtered and concentrated under reduced pressure. A white solid of molecule A13 in hydrochloride salt form is obtained.

Yield: 5.17 g (91%)

¹H NMR (TFA-d, ppm): 0.87 (3H); 1.06-1.46 (20H); 1.46-1.68 (2H); 1.68-2.81 (28H); 3.13-4.59 (12.5H); 4.83-5.25 (11H); 7.02-9.13 (37H)

DP (estimated as per ¹H NMR): 5.5

The calculated average molar mass of molecule A13 in hydrochloride salt form is 1609.8 g/mol.

Co-polyamino acid B15-1: Molecule A13 (3.47 g, 2.16 mmol) is solubilized in DCM (17 mL) then is added successively at 0° C. butyltetracarboxylic acid (BTCA, 115 mg, 0.49 mmol), HOPO (275 mg, 2.48 mmol), DIPEA (377 µL, 2.16 mmol) followed by EDC (473 mg, 2.47 mmol). After placing under stirring overnight at 0° C., the reaction medium is poured onto MeOH (220 mL) under stirring at 0° C. After leaving overnight, the white precipitate is retrieved by vacuum filtration, triturated with cold MeOH then dried under vacuum at 30° C.

Co-Polyamino Acid B15

A solution of co-polyamino acid B15-1 (2.33 g, 0.362 mmol) in DMAc (33 mL) is placed under a hydrogen atmosphere (1 atm) in the presence of 5% palladium on alumina (465 mg) then the solution is heated to 60° C. After overnight, the solution is cooled, filtered on Celite® then the filtrate is poured onto a 15% NaCl solution at pH 2 (500 mL). After overnight, the precipitate is filtered on a sintered filter then washed twice with a 15% NaCl solution (2×8 mL). The solid obtained is then solubilized in water (70 mL) by adjusting the pH to 7 by adding an aqueous solution of 1 N sodium hydroxide. After solubilization, the solution is filtered on a 0.45 µm filter then purified by ultrafiltration against a 0.9% NaCl solution, followed by water until the conductimetry of the permeate is less than 50 ρS/cm. The solution obtained is filtered on a 0.2 µm filter and stored at 2-8° C.

Dry extract: 25.8 mg/g

¹H NMR ($D_2O$, ppm): 0.90 (10.2H); 1.18-1.46 (68H); 1.53-1.9 (6.8H); 1.86-3.04 (101.2H); 3.17-3.80 (20.4H); 4.19-4.68 (22.1H)

DP (estimated as per ¹H NMR): 5.5

As per ¹H NMR: i=3.4

The calculated average molar mass of co-polyamino acid B15 is 4261.3 g/mol.

HPLC-Organic SEC (PEG calibrator): Mn=2700 g/mol.

Example B16: Co-Polyamino Acid B16—Sodium poly-L-glutamate Modified at the Extremities Thereof by Molecule A14 Wherein the Esters are Deprotected and Having a Number Average Molar Mass (Mn) of 3200 g/mol Co-Polyamino Acid B16-1: poly-L-benzylglutamate Obtained from the Polymerization of γ-benzyl-L-glutamate N-carboxyanhydride Initiated by 1-amino-4,7,10-trioxa-13-tridecane amine (TOTA).

By means of a similar method to that used for the preparation of co-polyamino acid B2-1 applied to TOTA (13.96 g, 63.37 mmol) and to γ-benzyl-L-glutamate N-carboxyanhydride (400.0 g, 1519 mmol), co-polyamino acid B16-1 is obtained.

Co-Polyamino Acid B16

To a solution of molecule A14 (6.74 g, 13.5 mmol) in DMAc (38 mL) are successively added HOPO (1.65 g, 14.8 mmol)m, and EDC (3.36 g, 17.6 mmol).

To a solution of co-polyamino acid B16-1 (30.0 g) in DMAc (113 mL) at ambient temperature are successively added DIPEA (1.90 mL, 13.5 mmol) followed by the solution of molecule A14 previously prepared.

After 24 h of stirring at ambient temperature, DMAc (82 mL) is added and the solution is placed at 60° C. under 10 bar hydrogen in the presence of 5% palladium on alumina (7.0 g). After 17 h of reaction, the reaction medium is filtered on a sintered filter then on a 0.2 µm PTFE filter.

The filtrate is placed under stirring, then a 300 g/L sodium carbonate solution (46 mL) followed by acetone (275 mL) are then added successively dropwise. After 3 h, the precipitate is filtered on a sintered filter, washed with acetone (3×70 mL) and dried under reduced pressure.

After solubilizing the solid obtained in water (1.3 L) then diluting with ethanol (0.7 L), the solution is basified by adding 10 N sodium hydroxide (13 mL) until a pH of 13 is obtained. After 3 h of stirring at ambient temperature, the solution is neutralized by adding 1 N HCl solution (190 mL) then the solution is filtered on an R53SLP carbon filter (3M), then on a 0.2 µm PES filter. The solution is then purified by ultrafiltration against a 0.9% NaCl solution, followed by water until the conductimetry of the permeate is less than 50 µS/cm. The solution obtained is filtered on a 0.2 µm filter and stored at 2-8° C.

Dry extract: 21.4 mg/g

DP (estimated as per ¹H NMR): 24

As per ¹H NMR: i=0.078

The calculated average molar mass of co-polyamino acid B16 is 4761 g/mol.

HPLC-Organic SEC (PEG calibrator): Mn=3200 g/mol.

Example B17: Co-Polyaminoacid B17—Sodium poly-L-glutamate Modified at the Two Extremities Thereof by Molecule A15 and Having a Number Average Molar Mass (Mn) of 3200 g/mol Co-Polyamino Acid B17-1: poly-L-benzylglutamate Obtained from the Polymerization of γ-benzyl-L-glutamate N-carboxyanhydride Initiated by Ethylenediamine.

By means of a similar method to that used for the preparation of co-polyamino acid B2-1 applied to ethylenediamine (4.77 g, 79.37 mmol) and to γ-benzyl-L-glutamate N-carboxyanhydride (500.0 g, 1899 mmol), co-polyamino acid B17-1 is obtained.

Co-Polyamino Acid B17

By means of a similar method to that used for the preparation of co-polyamino acid B16 applied to co-polyamino acid B17-1 (15.0 g) and to molecule A15 (3.45 g) with a saponification step at pH 12 for 50 min, co-polyamino acid B17 is obtained.

Dry extract: 20.3 mg/g
DP (estimated as per $^1$H NMR): 24
As per $^1$H NMR: i=0.048
The calculated average molar mass of co-polyamino acid B17 is 4237 g/mol.
HPLC-Organic SEC (PEG calibrator): Mn=3200 g/mol

Example B18: Co-Polyaminoacid B18—Sodium poly-L-glutamate Modified at the Two Extremities Thereof by Molecule A16 and Having a Number Average Molar Mass (Mn) of 3150 g/mol Co-Polyamino Acid B18-1: poly-L-benzylglutamate Obtained from the Polymerization of γ-benzyl-L-glutamate N-carboxyanhydride Initiated by Ethylenediamine.

By means of a similar method to that used for the preparation of co-polyamino acid B2-1 applied to ethylenediamine (4.74 g, 78.89 mmol) and to γ-benzyl-L-glutamate N-carboxyanhydride (498.4 g, 1893 mmol), co-polyamino acid B18-1 is obtained.

Co-Polyamino Acid B18

By means of a similar method to that used for the preparation of co-polyamino acid B17 applied to co-polyamino acid B18-1 (14.0 g) and to molecule A16 (4.26 g), co-polyamino acid B18 is obtained.

Dry extract: 9.7 mg/g
DP (estimated as per $^1$H NMR): 24
As per $^1$H NMR: i=0.075
The calculated average molar mass of co-polyamino acid B18 is 4839 g/mol.
HPLC-Organic SEC (PEG calibrator): Mn=3150 g/mol

Example B19: Co-Polyamino acid B19—Sodium poly-L-glutamate Modified at the Extremities Thereof by Molecule A17 Wherein the Esters are Deprotected and Having a Number Average Molar Mass (Mn) of 3400 g/mol By means of a similar method to that used for the preparation of co-polyamino acid B16 applied to co-polyamino acid B18-1 (20.39 g) and to molecule A17 (7.553 g), co-polyamino acid B19 is obtained.

Dry extract: 18.6 mg/g
DP (estimated as per $^1$H NMR): 24
As per $^1$H NMR: i=0.066
The calculated average molar mass of co-polyamino acid B19 is 4936 g/mol.
HPLC-Organic SEC (PEG calibrator): Mn=3400 g/mol

Example B20: Co-Polyaminoacid B20—Sodium poly-L-glutamate Modified at the Two Extremities Thereof by Molecule A18 and Having a Number Average Molar Mass (Mn) of 3200 g/mol By means of a similar method to that used for the preparation of co-polyamino acid B17 applied to co-polyamino acid B17-1 (12.45 g) and to molecule A18 (3.56 g), co-polyamino acid B20 is obtained.

Dry extract: 16.8 mg/g
DP (estimated as per $^1$H NMR): 24
As per $^1$H NMR: i=0.075
The calculated average molar mass of co-polyamino acid B20 is 4784 g/mol.
HPLC-Organic SEC (PEG calibrator): Mn=3200 g/mol

Example B21: Co-Polyaminoacid B21—Sodium poly-L-glutamate Modified at the Two Extremities Thereof by Molecule A19 and Having a Number Average Molar Mass (Mn) of 3600 g/mol By means of a similar method to that used for the preparation of co-polyamino acid B17 applied to co-polyamino acid B17-1 (12.16 g) and to molecule A19 (4.16 g), co-polyamino acid B21 is obtained.

Dry extract: 26.4 mg/g
DP (estimated as per $^1$H NMR): 24
As per $^1$H NMR: i=0.077
The calculated average molar mass of co-polyamino acid B21 is 5023 g/mol.
HPLC-Organic SEC (PEG calibrator): Mn=3600 g/mol

Example B23: Co-Polyaminoacid B23—Sodium Poly-L-Glutamate Modified at the Two Extremities Thereof by Molecule A21 and Having a Number Average Molar Mass (Mn) of 3350 g/mol By means of a similar method to that used for the preparation of co-polyamino acid B17 applied to co-polyamino acid B17-1 (18.68 g) and to molecule A21 (7.03 g), co-polyamino acid B23 is obtained.

Dry extract: 23.2 mg/g
DP (estimated as per $^1$H NMR): 24
As per $^1$H NMR: i=0.080
The calculated average molar mass of co-polyamino acid B23 is 5140 g/mol.
HPLC-Organic SEC (PEG calibrator): Mn=3350 g/mol

Example B24: Co-Polyamino Acid B24—Sodium poly-L-glutamate Modified at the Extremities Thereof by Molecule A1 and Having a Number Average Molar Mass (Mn) of 2300 g/mol Co-polyamino acid B24-1: poly-L-benzylglutamate obtained from the polymerization of γ-benzyl-L-glutamate N-carboxyanhydride initiated by molecule 4 and modified at the extremities thereof by molecule A1.

To a suspension of molecule 4 (9.92 mmol) in anhydrous DMF (80 mL) cooled to 0° C. is rapidly added a solution of -benzyl-L-glutamate N-carboxyanhydride (26.11 g, 99.2 mmol) in anhydrous DMF (20 mL) at 0° C. After 24 h of stirring at 0° C., a freshly prepared solution of molecule A1 (16.1 g, 49.6 mmol), HATU (18.9 g, 49.6 mmol) and DIPEA (8.64 mL, 49.6 mmol) in DMF (80 mL) is added to the medium and the mixture is stirred from 0° C. to 25° C. for 3.5 h. The resin is filtered, washed successively with DMF (3×100 mL), isopropanol (1×100 mL) and DCM (3×100 mL). The resin obtained is then treated with an 80:20 DCM/HFIP mixture (120 mL). After 30 min of stirring at ambient temperature, the resin is filtered and washed successively with DCM (3×100 mL). The solvents are evaporated at reduced pressure to produce co-polyamino acid B24-1

Co-Polyamino Acid B24

By means of a similar method to that used for the hydrogenation step of co-polyamino acid B16 applied to co-polyamino acid B24-1 (27.4 g), with a saponification step at pH 12 for 50 min but without the carbofiltration step, co-polyamino acid B24 is obtained.

Dry extract: 14.1 mg/g

DP (estimated as per $^1$H NMR): 14

As per $^1$H NMR: i=0.143

The calculated average molar mass of co-polyamino acid B24 is 2899 g/mol.

HPLC-Organic SEC (PEG calibrator): Mn=2300 g/mol.

Example B25: Co-Polyaminoacid B25—Sodium Poly-L-Glutamate Modified at the Extremities Thereof by Molecule A22 and Having a Number Average Molar Mass (Mn) of 3050 g/mol By means of a similar method to that used for the preparation of co-polyamino acid B17 applied to co-polyamino acid B18-1 (30.0 g) and molecule A22 (8.56 g) using a four-fold greater quantity of 300 g/L sodium carbonate solution to precipitate the polymer after the hydrogenolysis step, co-polyamino acid B25 is obtained.

Dry extract: 23.7 mg/g

DP (estimated as per $^1$H NMR): 24

As per $^1$H NMR: i=0.074

The calculated average molar mass of co-polyamino acid B25 is 4743 g/mol.

HPLC-Organic SEC (PEG calibrator): Mn=3050 g/mol

Example B26: Co-Polyaminoacid B26—Sodium poly-L-glutamate Modified at the Two Extremities Thereof by Molecule A23 and Having a Number Average Molar Mass (Mn) of 3400 g/mol By means of a similar method to that used for the preparation of co-polyamino acid B25 applied to co-polyamino acid B17-1 (25.78 g) and to molecule A23 (8.27 g), co-polyamino acid B21 is obtained.

Dry extract: 11.8 mg/g

DP (estimated as per $^1$H NMR): 24

As per $^1$H NMR: i=0.073

The calculated average molar mass of co-polyamino acid B21 is 4902 g/mol.

HPLC-Organic SEC (PEG calibrator): Mn=3400 g/mol

Example B27: Co-Polyamino Acid B27—Butyltetracarboxylic Acid Substituted with Molecule A24 Wherein the Esters are Deprotected and Having a Number Average Molar Mass (Mn) of 2500 g/mol Molecule A24

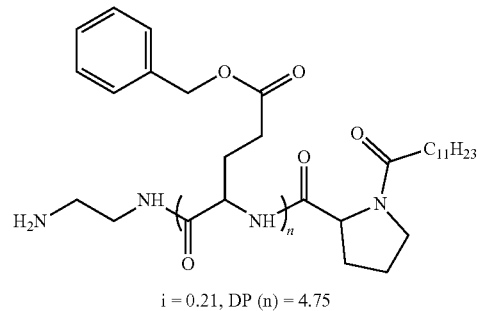

i = 0.21, DP (n) = 4.75

Molecule 53: Product Obtained by Polymerization of γ-benzyl-L-glutamate N-carboxyanhydride Initiated by N-Boc-ethylenediamine then Capped with Molecule 2.

A solution of BocEDA (12.00 g, 74.9 mmol) in DMF (12 mL) is prepared. In a reaction vessel, γ-benzyl-L-glutamate N-carboxyanhydride (78.87 g, 300.0 mmol) is solubilized in DMF (165 mL) at 25° C. The mixture is then stirred until complete dissolution, cooled to -10° C., then the BocEDA solution is introduced rapidly. The reaction medium is stirred at 0° C. for 3 h then are introduced successively DMF (100 mL), molecule 2 (26.73 g, 89.88 mmol), HOPO (9.99 g, 89.88 mmol) and EDC (17.23 g, 89.88 mmol). The reaction mixture is stirred at 0° C. for 1 h, from 0° C. to 20° C. for 2 h then at 20° C. for 16 h. It is then poured onto a 1:1 2-propanol/H$_2$O solution (10 V) under stirring. After 3 h, the white precipitate is filtered on a sintered filter, washed with a 1:1 2-propanol/H$_2$O mixture (2×360 mL) and dried at 30° C. at reduced pressure.

Yield: 70 g (71%)

$^1$H NMR (TFA-d, ppm): 0.99 (3H); 1.34-1.59 (16H); 1.68-2.85 (36H); 3.52-3.62 (2H); 3.79-3.99 (4H); 4.70-4.92 (5.75H); 5.20-5.38 (9.5H); 7.36-7.52 (23.75H).

DP (estimated as per $^1$H NMR): 4.75

The calculated average molar mass of molecule 53 is 1481.0 g/mol.

Molecule A24

By means of a similar method to that used for the preparation of molecule A13 applied to molecule 53 (34.00 g, 22.96 mmol), a white solid of molecule A24 in hydrochloride salt form is obtained.

Yield: 29.40 g (90%)

$^1$H NMR (TFA-d, ppm): 1.00 (3H); 1.35-1.61 (16H); 1.79-1.93 (2H); 2.05-2.90 (25H); 3.53-3.65 (2H); 3.79-4.02 (4H); 4.74-4.94 (5.75H); 5.20-5.43 (9.5H); 7.32-7.58 (23.75H).

DP (estimated as per $^1$H NMR): 4.75

The calculated average molar mass of molecule A13 in hydrochloride salt form is 1417.2 g/mol.

Co-Polyamino Acid B27-1:

By means of a similar method to that used for the preparation of co-polyamino acid B15-1 applied to molecule A24 (11.9 g, 8.40 mmol) and to BTCA (0.41 g, 1.75 mmol) in solution in DMF, a white solid is obtained after drying at 30° C. at reduced pressure.

Co-Polyamino Acid B27

By means of a similar method to that used for the preparation of co-polyamino acid B15 applied to co-polyamino acid B27-1 (9.31 g, 1.64 mmol), under hydrogen pressure (6 bar) and with a saponification step at pH 12 for 1 h prior to the ultrafiltration step, co-polyamino acid B27 is obtained.

Dry extract: 19.9 mg/g
DP (estimated as per $^1$H NMR): 4.75
As per $^1$H NMR: i=3.7
The calculated average molar mass of co-polyamino acid B27 is 4085.8 g/mol.
HPLC-Organic SEC (PEG calibrator): Mn=2500 g/mol.

Example B28: Co-polyamino Acid B28—Tricarballylic Acid Substituted with Molecule A25 Wherein the Esters are Deprotected and Having a Number Average Molar Mass (Mn) of 2200 g/mol Molecule A25

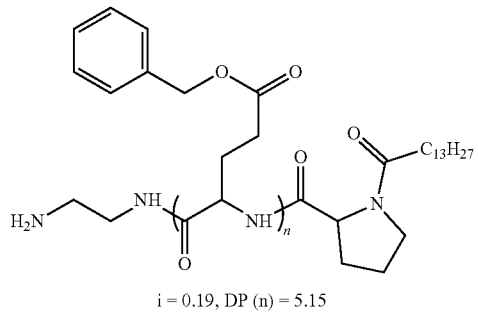

i = 0.19, DP (n) = 5.15

Molecule 54:

Product obtained by polymerization of γ-benzyl-L-glutamate N-carboxyanhydride initiated by N-Boc-ethylenediamine then capped with molecule A1. By means of a similar method to that used for the preparation of molecule 53 applied to BocEDA (6.00 g, 37.45 mmol), to γ-benzyl-L-glutamate N-carboxyanhydride (39.44 g, 150.00 mmol) and to molecule A1 (14.63 g, 44.94 mmol), a white solid of molecule 54 is obtained.

Yield: 23.71 g (40%)
$^1$H NMR (CDCl$_3$, ppm): 0.87 (3H); 1.12-2.76 (57.6H); 3.06-4.50 (12.15H); 4.90-5.25 (10.3H); 5.91-8.49 (32.9H).
DP (estimated as per $^1$H NMR): 5.15
The calculated average molar mass of molecule 54 is 1596.8 g/mol.

Molecule A25

By means of a similar method to that used for the preparation of molecule A13 applied to molecule 54 (23.29 g, 14.59 mmol), a translucent solid of molecule A25 in hydrochloride salt form is obtained.

Yield: 19.08 g (85%)
$^1$H NMR (CDCl$_3$, ppm): 0.87 (3H); 1.17-1.32 (20H); 1.48-1.63 (2H); 1.69-2.78 (29.6H); 3.15-4.40 (12.15H); 4.89-5.18 (10.3H); 7.06-9.13 (31.9H).
DP (estimated as per $^1$H NMR): 5.15
The calculated average molar mass of molecule A25 in hydrochloride salt form is 1533.1 g/mol.

Co-Polyamino Acid B28-1:

By means of a similar method to that used for the preparation of co-polyamino acid B15-1 applied to molecule A25 (3.93 g, 2.56 mmol) and to tricarballylic acid (TCA, 125.2 mg, 0.71 mmol) in solution in DMF, a white solid is obtained after drying at 30° C. at reduced pressure.

Co-Polyamino Acid B28

By means of a similar method to that used for the preparation of co-polyamino acid B15 applied to co-polyamino acid B28-1 (2.98 g, 0.65 mmol) and with a saponification step at pH 12 for 1 h prior to the ultrafiltration step, co-polyamino acid B28 is obtained.

Dry extract: 25.8 mg/g
DP (estimated as per $^1$H NMR): 5.15
As per $^1$H NMR: i=3.0
The calculated average molar mass of co-polyamino acid B28 is 3559.2 g/mol.
HPLC-Organic SEC (PEG calibrator): Mn=2200 g/mol.

Example B29: Co-Polyamino Acid B29—4,7,10-trioxa-1,13-tridecanediamine (TOTA) Substituted with Molecule A12 Wherein the Esters are Deprotected and Having a Number Average Molar Mass (Mn) of 2000 g/mol Co-Polyamino Acid B29-1:

To a solution of molecule A12 (3.70 g, 1.98 mmol) in chloroform (31 mL) at ambient temperature are added successively HOBt (304 mg, 1.98 mmol) and 4,7,10-trioxa-1,13-tridecanediamine (TOTA, 208 mg, 0.94 mmol). The mixture is cooled to 0° C. then EDC (380 mg, 1.98 mmol) is added. The reaction medium is stirred for 15 min at 0° C. followed by 18 h at ambient temperature. The organic phase is washed with a 0.1 N HCl aqueous solution (2×28 mL), and the organic phase is dried over Na$_2$SO$_4$, filtered and concentrated under reduced pressure. The solid obtained is solubilized in CHCl$_3$ (40 mL) and the solution is added dropwise to IPE (400 mL) under stirring. The suspension is placed in an ice bath without stirring for 17 h. The suspension is centrifuged at 3200 rpm for 10 min at 25° C. The colorless supernatant is removed and the solid obtained is concentrated under reduced pressure.

Yield: 4.59 g (quant.)
$^1$H NMR (CDCl$_3$, ppm): 0.88 (12H); 1.12-1.58 (192H); 1.58-2.17 (48H); 2.17-2.62 (44H); 3.08 (2H); 3.13-3.38 (6H); 3.48 (4H); 3.53-3.66 (12H); 3.74-3.83 (4H); 3.92 (2H); 4.00-4.12 (4H); 4.12-4.33 (10H); 4.37 (2H); 6.72-6.84 (4H); 7.06 (2H); 7.31 (2H); 7.52 (2H); 7.82 (2H); 7.94 (2H); 8.57-8.69 (4H).

Co-Polyamino Acid B29

Molecule B29-1 (3.67 g, 0.93 mmol) is solubilized in TFA (11.5 mL) and the solution is stirred at ambient temperature for 6 h. The solution is poured dropwise onto IPE (18 mL) at 5° C. then water (18 mL) is added. The suspension is placed in an ice bath under stirring for 15 h. The suspension is filtered and triturated with IPE (10 mL) and water (2×10 mL). The residue is dried under reduced pressure then solubilized in a 1 N NaOH solution (56 mL) with regular addition of 1 N NaOH to maintain the pH at 7. The solution is diluted to 20 g/L theoretical with water then purified by ultrafiltration against a 0.9% NaCl solution, followed by water until the conductimetry of the permeate is less than 50 µS/cm. The solution obtained is filtered on a 0.2 µm filter and stored at 2-8° C.

Dry extract: 8.0 mg/g
The calculated average molar mass of co-polyamino acid B29 is 3520 g/mol.
HPLC-Organic SEC (PEG calibrator): Mn=2000 g/mol.

Example B30: Co-Polyamino Acid B30—Tricarballylic Acid Substituted with Molecule A26 Wherein the Esters are Deprotected and Having a Number Average Molar Mass (Mn) of 2100 g/mol Co-Polyamino Acid B30-1:

By means of a similar method to that used for the preparation of co-polyamino acid B15-1 applied to molecule A26 (10.87 g, 11.33 mmol) and to tricarballylic acid (TCA, 0.605 g, 3.43 mmol) in solution in DMF, a white solid is obtained after 2 consecutive precipitations of the product in solution in DMF in a 50:50 $H_2O$/MeCN mixture (10V), filtration, trituration with a 50:50 $H_2O$/MeCN mixture followed by drying under reduced pressure at 30° C.

Co-Polyamino Acid B30

Co-polyamino acid B30-1 (8.53 g, 2.95 mmol) is solubilized in TFA (30 mL), and the solution is stirred for 3 h at ambient temperature then is poured dropwise onto water under stirring (300 mL). After 1 h, the white precipitate is retrieved by filtration, triturated with water and dried under reduced pressure. The solid obtained is then solubilized in water (350 mL) by adjusting the pH to 7 adding an aqueous solution of 1 N sodium hydroxide. The solution is filtered on a 0.2 µm filter then purified by ultrafiltration against a 0.9% NaCl solution, followed by water until the conductimetry of the permeate is less than 50 µS/cm. The solution obtained is filtered on a 0.2 µm filter and stored at 2-8° C.

Dry extract: 28.8 mg/g

The molar mass of co-polyamino acid B30 is 2585 g/mol.

HPLC-Organic SEC (PEG calibrator): Mn=2100 g/mol.

Example B31: Co-Polyamino Acid B31—Sodium poly-L-glutamate Modified at the Extremities Thereof by Molecule A27 Wherein the Esters are Deprotected and Having a Number Average Molar Mass (Mn) of 3800 g/mol By means of a similar method to that used for the preparation of co-polyamino acid B16 applied to co-polyamino acid B18-1 (28.6 g) and to molecule A27 (6.799 g), co-polyamino acid B31 is obtained.

Dry extract: 20.5 mg/g

DP (estimated as per $^1$H NMR): 24

As per $^1$H NMR: i=0.075

The calculated average molar mass of co-polyamino acid B31 is 4591 g/mol.

HPLC-Organic SEC (PEG calibrator): Mn=3800 g/mol

Part C: Compositions

The glucagon used is human glucagon obtained from a peptide synthesis process. It is supplied by Bachem (reference 4074733).

Example C1: 2 mg/mL Glucagon Solution

Into a 50 mL Falcon tube is introduced 94.7 mg of glucagon DS powder followed by 45 mL of a 0.003 N hydrochloric acid solution containing 2 mg/mL of L-methionine. The glucagon powder is mixed by inverting the tube repeatedly until the glucagon has completely dissolved. The 2 mg/mL glucagon solution is then filtered on a membrane (0.22 µm).

Example C2: 4 mg/ml Glucagon Solution

Glucagon (160 mg) powder is introduced into a 45 ml Falcon tube then 40 mL of the 0.006 N hydrochloric acid aqueous solution containing 2 mg/mL of L-methionine is added. The glucagon powder is mixed by inverting the tube repeatedly until the glucagon has completely dissolved. The 4 mg/ml glucagon solution is then filtered on a membrane (0.22 µm).

Example CA0: Preparation of a 1 mg/ml glucagon Solution Containing Different Co-Polyamino Acids According to the Invention, a Phosphate Buffer (2 mM) and Glycerin at pH 7.2

In a flask containing concentrated solutions of excipients (phosphate, glycerol (to obtain 300 mosmole/kg in the final formulation)) and potentially additives (m-cresol, citrate), is added a co-polyamino acid solution. The composition is briefly stirred until the co-polyamino acid has dissolved, then the solution is filtered on a membrane (0.22 µM).

The equivolume mixture of this solution with the freshly prepared glucagon solution, as described in example C1, results in the final compositions CA1 to CA68 containing 1 mg/ml of glucagon. The pH of the solution is adjusted to pH 7.2±0.1 by adding 1 N NaOH/HCl then filtered on a membrane (0.22 µm). The details of the compositions are summarized in Table 1.

A visual inspection is carried out to determine whether a clear solution is obtained or not (by way of comparison, the glucagon solution at neutral pH is not soluble above 0.2 mg/ml). The visual inspection of the samples is carried out in order to detect visible particles, or turbidity. This inspection is carried out as per the recommendations of the European Pharmacopeia (EP 2.9.20): the samples are placed under lighting of at least 2000 lux and are observed against a white background and a black background. When particles are visible in half of the samples, the composition is deemed to be unclear.

TABLE 1

Compositions and visual appearance of 1 mg/mL glucagon solutions at pH 7.2 at different co-polyamino acid concentrations containing phosphate buffer (2 mM) and 1 mg/mL of L-methionine.

| Composition | Co-polyamino acid | Co-polyamino acid concentration (mg/mL) | Ratio of Co-polyamino acid/glucagon | Additive | Glycerin (mM) | Visual appearance of solution |
|---|---|---|---|---|---|---|
| CA1 | B5 | 5.25 | 3.7 | — | 290 | clear |
| CA2 | | 4.70 | 3.3 | — | 290 | clear |
| CA3 | | 3.90 | 2.7 | — | 290 | clear |
| CA4 | | 2.71 | 1.9 | 10 mM citrate | 255 | clear |

TABLE 1-continued

Compositions and visual appearance of 1 mg/mL glucagon solutions at pH 7.2 at different co-polyamino acid concentrations containing phosphate buffer (2 mM) and 1 mg/mL of L-methionine.

| Composition | Co-polyamino acid | Co-polyamino acid concentration (mg/mL) | Ratio of Co-polyamino acid/glucagon | Additive | Glycerin (mM) | Visual appearance of solution |
|---|---|---|---|---|---|---|
| CA5 | | 2.85 | 2.0 | 10 mM citrate | 255 | clear |
| CA6 | B6 | 2.89 | 2.0 | — | 290 | clear |
| CA7 | | 2.61 | 1.8 | — | 290 | clear |
| CA8 | | 2.23 | 1.5 | — | 290 | clear |
| CA9 | | 2.8 | 1.9 | 10 mM citrate | 250 | clear |
| CA10 | | 2.95 | 2 | 10 mM citrate | 250 | clear |
| CA11 | B9 | 2.49 | 1.5 | 10 mM citrate | 255 | clear |
| CA12 | | 2.82 | 1.7 | 10 mM citrate | 255 | clear |
| CA13 | | 2.49 | 1.5 | — | 295 | clear |
| CA14 | | 2.82 | 1.7 | — | 295 | clear |
| CA16 | B5 | 1.42 | 1 | — | 290 | clear |
| CA17 | | 1.71 | 1.2 | — | 290 | clear |
| CA18 | | 2.13 | 1.5 | — | 290 | clear |
| CA19 | | 1.42 | 1 | 10 mM citrate | 260 | clear |
| CA20 | | 2.13 | 1.5 | 10 mM citrate | 260 | clear |
| CA21 | B6 | 1.18 | 0.8 | — | 290 | clear |
| CA22 | | 1.47 | 1.0 | — | 290 | clear |
| CA23 | | 1.77 | 1.2 | — | 290 | clear |
| CA23-2 | | 1.18 | 0.8 | 10 mM citrate | 260 | clear |
| CA24 | | 1.47 | 1 | 10 mM citrate | 260 | clear |
| CA25 | | 1.77 | 1.2 | 10 mM citrate | 260 | clear |
| CA27 | B9 | 1.66 | 1 | 10 mM citrate | 260 | clear |
| CA28 | | 1.99 | 1.2 | 10 mM citrate | 260 | clear |
| CA29 | | 1.66 | 1 | — | 300 | clear |
| CA30 | | 1.99 | 1.2 | — | 300 | clear |
| CA31 | B18 | 5.56 | 4.0 | 10 mM citrate | 260 | clear |
| CA32 | | 6.25 | 4.5 | 10 mM citrate | 260 | clear |
| CA35 | B29 | 2.02 | 2.0 | 10 mM citrate | 260 | clear |
| CA36 | | 2.53 | 2.5 | 10 mM citrate | 260 | clear |
| CA37 | | 2.02 | 2.0 | — | 283 | clear |
| CA38 | | 2.53 | 2.5 | — | 283 | clear |
| CA39 | B26 | 2.82 | 2.0 | 10 mM citrate | 260 | clear |
| CA40 | | 3.53 | 2.5 | 10 mM citrate | 260 | clear |
| CA41 | | 2.82 | 2.0 | 10 mM citrate + 290 µM Zn | 260 | clear |
| CA42 | | 3.39 | 2.4 | 10 mM citrate + 290 µM Zn | 260 | clear |

TABLE 1-continued

Compositions and visual appearance of 1 mg/mL glucagon solutions at pH 7.2 at different co-polyamino acid concentrations containing phosphate buffer (2 mM) and 1 mg/mL of L-methionine.

| Composition | Co-polyamino acid | Co-polyamino acid concentration (mg/mL) | Ratio of Co-polyamino acid/glucagon | Additive | Glycerin (mM) | Visual appearance of solution |
|---|---|---|---|---|---|---|
| CA43 |  | 2.82 | 2.0 | — | 283 | clear |
| CA44 |  | 3.53 | 2.5 | — | 283 | clear |
| CA45 | B23 | 6.50 | 4.5 | — | 295 | clear |
| CA46 |  | 6.78 | 4.7 | — | 295 | clear |
| CA47 |  | 6.50 | 4.5 | 25 mM NaCl | 245 | clear |
| CA48 |  | 6.78 | 4.7 | 25 mM NaCl | 245 | clear |
| CA49 |  | 6.50 | 4.5 | 50 mM NaCl | 195 | clear |
| CA50 |  | 6.78 | 4.7 | 50 mM NaCl | 195 | clear |
| CA51 |  | 6.50 | 4.5 | 75 mM NaCl | 145 | clear |
| CA52 |  | 6.78 | 4.7 | 75 mM NaCl | 145 | clear |
| CA53 |  | 6.50 | 4.5 | 100 mM NaCl | 95 | clear |
| CA54 |  | 6.78 | 4.7 | 100 mM NaCl | 95 | clear |
| CA55 |  | 5.97 | 4.0 | 10 mM citrate | 260 | clear |
| CA56 |  | 6.72 | 4.5 | 10 mM citrate | 260 | clear |
| CA57 |  | 5.97 | 4.0 | 10 mM citrate + 290 μM Zn | 260 | clear |
| CA58 |  | 7.02 | 4.7 | 10 mM citrate + 290 μM Zn | 260 | clear |
| CA59 |  | 6.50 | 4.5 | 10 mM citrate + 25 mM NaCl | 205 | clear |
| CA60 |  | 6.78 | 4.7 | 10 mM citrate + 25 mM NaCl | 205 | clear |
| CA61 | B2 | 7.47 | 5 | — | 295 | clear |
| CA62 |  | 7.47 | 5 | 10 mM NaCl | 275 | clear |
| CA63 |  | 7.47 | 5 | 50 mM NaCl | 195 | clear |
| CA64 |  | 10.4 | 7 | — | 295 | clear |
| CA65 |  | 10.4 | 7 | 10 mM NaCl | 275 | clear |
| CA66 |  | 10.4 | 7 | 50 mM NaCl | 195 | clear |
| CA67 | B26 | 3.8 | 2.7 | 10 mM citrate | 244 | clear |
| CA68 | B23 | 9.7 | 6.5 | 10 mM citrate | 244 | clear |

Example CB0: Preparation of a 2 mg/ml Glucagon Solution Containing Different Co-Polyamino Acids According to the Invention, a Phosphate Buffer (2 mM), 1 mg/ml of L-methionine and Glycerin at pH 7.2

Similarly to example CA0, 2 mg/mL glucagon compositions containing different co-polyamino acids, glycerol (to obtain 300 mOsmoles/kg in the final formulation), a phosphate buffer (2 mM) and additives are prepared. They are shown in Table 2 below:

TABLE 2

Compositions and visual appearance of 2 mg/mL glucagon solutions at pH 7.2 at different co-polyamino acid concentrations containing phosphate buffer (2 mM) and 1 mg/mL of L-methionine.

| Composition | Co-polyamino acid | Co-polyamino acid concentration (mg/mL) | Ratio of co-polyamino acid/glucagon | Additive | Glycerin (mM) | Visual appearance of solution |
|---|---|---|---|---|---|---|
| CB1 | B5 | 8.5 | 3 | — | 290 | clear |
| CB2 | | 8.5 | 3 | 10 mM citrate | 255 | clear |
| CB3 | B6 | 7.4 | 2.5 | — | 290 | clear |
| CB4 | | 7.4 | 2.5 | 10 mM citrate | 250 | clear |
| CB5 | B9 | 6.6 | 2 | 10 mM citrate | 255 | clear |
| CB6 | | 5.6 | 1.7 | — | 295 | clear |

Monitoring of Physical Stability of Compositions

The previously prepared compositions were transferred into cartridges (OMPI 3 ml easy-to-fill—Ref P40B4100.3250) at a rate of 1 mL per cartridge and placed under static conditions at 37° C.

The visual inspection of the samples placed under static conditions at 37° C. is carried out at 0, 1, 2, 3, 4, 5, 6 weeks at 37° C. so as to detect the appearance of visible particles, fibrils or turbidity. This inspection is carried out as per the recommendations of the European Pharmacopeia (EP 2.9.20): the samples are placed under lighting of at least 2000 Lux and are observed against a white background and a black background to comply with European Pharmacopeia requirements. When particles are visible in half of the samples, the composition is deemed to be unstable. Therefore, stable means that, on the day of the inspection, at least half of the samples were free from particles, fibrils or turbidity.

The results of the visual inspections are reported in the following table.

The physical stability study of the compositions of examples CA1, CA6, CA8, CA9, CA13 and CA61 to CA68 described in Table 3 hereinafter was conducted on 1 ml volumes of composition in cartridges with a capacity of 3 ml (OMPI—ref: P40B4100.3250). By way of comparison, the 1 mg/mL glucagon solution at acidic pH is only stable for 2 days at 37° C.

TABLE 3

Physical stability at 37° C. of co-polyamino acid compositions in cartridges.

| Composition | Co-polyamino acid | Co-polyamino acid concentration (mg/mL) | Additive | Stability (weeks) |
|---|---|---|---|---|
| CA1 | B5 | 5.25 | — | >4 |
| | | | | >5 |
| CA6 | B6 | 2.89 | — | >4 |
| | | | | >22 |
| CA8 | | 2.23 | — | >4 |
| | | | | >6 |
| CA9 | | 2.8 | 10 mM citrate | >4 |
| | | | | >19 |
| CA13 | B9 | 2.49 | — | >2 |
| CA61 | B2 | 10.4 | — | >1 |
| CA62 | | | | |
| CA63 | | | | |
| CA64 | | | | |
| CA65 | | 10.4 | 10 mM NaCl | >8 |
| CA66 | | 10.4 | 50 mM NaCl | >20 |
| CA67 | B26 | 3.8 | 10 mM citrate | >16 |
| CA68 | B23 | 9.7 | 10 mM citrate | >16 |

The compositions according to the invention exhibit a physical stability at 37° C. under static conditions of greater than two weeks at 37° C. Adding co-polyamino acid makes it possible to solubilize and stabilize the glucagon at neutral pH whereas the glucagon in solution at acidic pH is only stable for a few days at 37° C. (2 days).

Results of Visual Observations on Mixture and Fibrillation Measurements by ThT

Principle

The poor stability of a peptide may give rise to the formation of amyloid fibrils, defined as organized macromolecular structures. These may potentially result in gel formation in the sample.

The thioflavin T (ThT) fluorescence monitoring test is used to analyze the physical stability of the solutions. Thioflavin is a small molecular probe having a characteristic fluorescence signature when it binds to amyloid type fibrils (Naiki et al. (1989) Anal. BioChem. 177, 244-249; LeVine (1999) Methods. Enzymol. 309, 274-284).

This method makes it possible to monitor fibril formation for low ThT concentrations in undiluted solutions. This monitoring is carried out under accelerated stability conditions: under stirring and at 37° C.

Experimental Conditions

Each composition is described in the associated example. Thioflavin T was added in the composition using a concentrated stock solution so as to induce a negligible dilution of the composition. The Thioflavin T concentration in the composition is 40 µM.

A 150 µL volume of the composition was introduced into a well of a 96-well plate then 2.7 µL of concentrated ThT solution was introduced. Each composition was analyzed in three tests (triplicate) in the same plate. The plate was sealed with transparent film so as to prevent the evaporation of the composition.

This plate was then placed in the enclosure of a plate reader (Xenius XC, SAFAS). The temperature is set to 37° C., and lateral stirring of 960 rpm with 1 mm amplitude is applied.

A fluorescence intensity reading in each well is carried out with an excitation wavelength of 442 nm, and an emission wavelength of 482 nm over time.

The fibrillation process is conveyed by a significant increase in fluorescence after an interval known as the latent period.

The lag time is determined graphically, taking the time when the tangent to the linear growth phase intersects with the x-axis.

The value of the latent period reported corresponds to the mean of the latent period measurements made on three wells.

The latent period results obtained are presented in Table 4 below. By way of comparison, under these conditions, glucagon alone is insoluble in solution at physiological pH and the 1 mg/mL glucagon at acidic pH displays a fibrillation time of about 0.5 h.

TABLE 4

Measurement of latent period of co-polyamino acid compositions.

| Composition | Co-polyamino acid | Co-polyamino acid concentration (mg/mL) | Additive | Fibrillation time (h) |
|---|---|---|---|---|
| CA16 | B5 | 1.42 | — | >10 |
| CA17 |  | 1.71 | — | >10 |
| CA18 |  | 2.13 | — | >15 |
| CA19 |  | 1.42 | 10 mM citrate | >7 |
| CA20 |  | 1.71 | 10 mM citrate | >10 |
| CA21 | B6 | 1.18 | — | >15 |
| CA22 |  | 1.47 | — | >15 |
| CA23 |  | 1.77 | — | >30 |
| CA24 |  | 1.47 | 10 mM citrate | >15 |

TABLE 4-continued

Measurement of latent period of co-polyamino acid compositions.

| Composition | Co-polyamino acid | Co-polyamino acid concentration (mg/mL) | Additive | Fibrillation time (h) |
|---|---|---|---|---|
| CA25 |  | 1.77 | 10 mM citrate | >20 |
| CA27 | B9 | 1.66 | 10 mM citrate | >20 |
| CA28 |  | 1.99 | 10 mM citrate | >40 |
| CA29 |  | 1.66 | — | >30 |
| CA30 |  | 1.99 | — | >30 |
| CA31 | B18 | 5.56 | 10 mM citrate | >80 |
| CA32 |  | 6.25 | 10 mM citrate | >115 |
| CA35 | B29 | 2.02 | 10 mM citrate | >40 |
| CA36 |  | 2.53 | 10 mM citrate | >90 |
| CA37 |  | 2.02 | — | 20 < t < 25 |
| CA38 |  | 2.53 | — | 40 < t < 50 |
| CA39 | B26 | 2.82 | 10 mM citrate | >25 |
| CA40 |  | 3.53 | 10 mM citrate | >90 |
| CA42 |  | 3.39 | 10 mM citrate + 290 µM Zn | >115 |
| CA44 |  | 3.53 | — | 10 < t < 15 |
| CA46 | B23 | 6.78 | — | 5 < t < 8 |
| CA48 |  | 6.78 | 25 mM NaCl | >10 |
| CA50 |  | 6.78 | 50 mM NaCl | >20 |
| CA52 |  | 6.78 | 75 mM NaCl | >30 |
| CA54 |  | 6.78 | 100 mM NaCl | >35 |
| CA56 |  | 6.72 | 10 mM citrate | >40 |
| CA61 | B2 | 7.47 | — | 5 < t < 7 |
| CA62 |  | 7.47 | 10 mM NaCl | >13 |
| CA63 |  | 7.47 | 50 mM NaCl | >50 |

The compositions containing co-polyamino acids makes it possible to increase the latent period compared to the solution of glucagon alone at acidic pH which is only stable for a few minutes under these measurement conditions. Adding salt and optionally zinc makes it possible to increase stability, in particular for compounds B2, B23, B26 and B29.

The invention claimed is:

1. A composition in the form of an injectable aqueous solution, wherein the pH is from 6.0 to 8.0, comprising at least:
   a) human glucagon;
   b) a co-polyamino acid consisting of glutamic or aspartic units chosen among the co-polyamino acids according to formula I as defined below:

[Q(PLG)$_k$][Hy]$_j$[Hy]$_{j'}$,  Formula I wherein:
   j≥1; 0≤j'≤n'1; k≥2
   said co-polyamino acid according to formula I bearing carboxylate charges and at least one hydrophobic radical -Hy, the co-polyamino acid including at least two chains of glutamic or aspartic units PLG bound together by an at least divalent linear or branched radical or spacer Q[-*]$_k$ consisting of an alkyl chain comprising one or a plurality of heteroatoms chosen from the group consisting of nitrogen and oxygen atoms and/or bearing one or a plurality of heteroatoms consisting of nitrogen and oxygen radicals and/or radicals bearing one or a plurality of heteroatoms consisting of nitrogen and oxygen atoms and/or carboxyl functions,
   said radical or spacer Q[-*]$_k$ being bound to at least two glutamic or aspartic unit chains PLG by an amide function,
   said amide functions binding said radical or spacer Q[-*]$_k$ bound to said at least two chains of glutamic or aspartic units result from the reaction between an amine function and an acid function respectively borne either by a precursor Q' of the radical or spacer Q[-*]$_k$ or by a glutamic or aspartic unit, and said hydrophobic radical -Hy being bound either to a terminal amino acid unit and then j≥1, or to a carboxyl function borne by one of the chains of the glutamic or aspartic units PLG and then j'=n'1 and n'1 is the mean number of monomeric units bearing a hydrophobic radical -Hy.

2. The composition according to claim 1, wherein said radical or spacer Q[-*]$_k$ is chosen among the radicals according to formula II:

Q[-*]$_k$=([Q']$_q$)[-*]$_k$        Formula II wherein 1≤q≤5.

3. The composition according to claim 2, wherein said radicals Q', identical or different, are chosen from the group consisting of the radicals according to formulas III to VII hereinafter, to form Q[-*]k by a radical according to formula III:

*-F$_a$-[-CH$_2$-]$_t$-F$_{a'}$-*        Formula III wherein 1≤t≤8 by a radical according to formula IV:

*—F$_b$-[CH$_2$-]$_u$[-O-(-CH$_2$-)$_{u'_1}$]$_{u''_1}$[-O-(-CH$_2$-)$_{u'_2}$]$_{u''_2}$-F$_{b'}$—*        Formula IV wherein:
at least one of u$_1$" or u$_2$" is not 0,
if u$_1$"≠0 then u$_1$'≠0 and if u$_2$"≠0 then u$_2$'≠0,
u$_1$' and u$_2$' are identical or different and,
2≤u≤4,
0≤u$_1$'≤4,
0≤u$_1$"≤4,
0≤u$_2$'≤4,
0≤u$_2$"≤4, by a radical according to formula V:

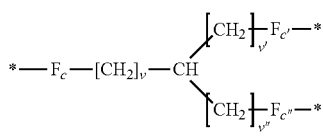

Formula V wherein:
v, v' and v" identical or different, are integers≥0, and v+v'+v"≤15, by a radical according to formula VI:

*—F$_d$—(CH$_2$)$_{\overline{w_1}}$[F$_y$-(CH$_2$-)$_{\overline{w'_1}}$]$_{w''_1}$[F$_y$-(CH$_2$-)$_{\overline{w'_2}}$]$_{w''_2}$(CH$_2$-)$_{\overline{w_2}}$F$_{d'}$—*        Formula VI wherein:
w$_1$' is not 0,
0≤w$_2$"≤1,
w$_1$≤6 and w$_1$'≤6 and/or w$_2$≤6 and w$_2$'≤6
where Fa, Fb, Fc, Fd, Fa', Fb', Fc', Fc" and Fd', are identical or different, each being selected from —NH— or —CO—, and Fy representing a trivalent nitrogen atom —N=, two radicals Q' being bound together by a covalent bond between a carbonyl function, Fa, Fb, Fc, Fd, Fa', Fb', Fc', Fc" and Fd'=—CO—, and an amine function Fa Fb, Fc, Fd, Fa', Fb', Fc', Fc" and Fd'=—NH— or Fy=—N=, thus forming an amide bond.

4. The composition according to claim 1, wherein the hydrophobic radical -Hy is chosen among the radicals according to formula X as defined hereinafter:

*-(-GpR-)$_r$-(-GpG-)$_g$-(-GpA-)$_a$-[-(GpL-)$_l$-[-(GpH-)$_h$-GpC]$_l$]$_{a'}$        Formula X wherein GpR is chosen among the radicals according to formulas VII, VII' or VII":

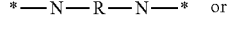

Formula VII

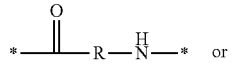

Formula VII'

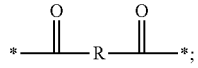

Formula VII"

GpG and GpH identical or different are chosen among the radicals according to formulas XI or XI':

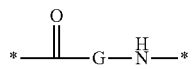

Formula XI

Formula XI'

GpA is chosen among the radicals according to formula VIII:

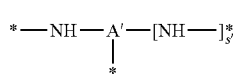

Formula VIII wherein A' is chosen among the radicals according to VIII', VIII" or VIII'":

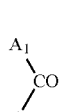

Formula VIII'

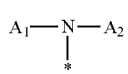

Formula VIII"

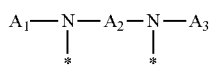

Formula VIII'"

-GpL is chosen among the radicals according to formula XII:

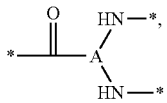

Formula XII

GpC is a radical according to formula IX:

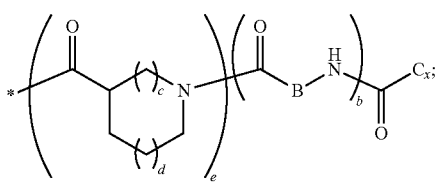

Formula IX the * indicates the binding sites of the different groups bound by amide functions;
a is an integer equal to 0 or to 1 and a'=1 if a=0 and a'=1, 2 or 3 if a=1;
a' is an integer equal to 1, to 2 or to 3;
b is an integer equal to 0 or to 1;
c is an integer equal to 0 or to 1, and if c is equal to 0 then d is equal to 1 or to 2;
d is an integer equal to 0, to 1 or to 2;
e is an integer equal to 0 or to 1;
g is an integer equal to 0, to 1, to 2, to 3 to 4 to 5 or to 6;
h is an integer equal to 0, to 1, to 2, to 3 to 4 to 5 or to 6;
l is an integer equal to 0 or 1 and l'=1 if l=0 and l'=2 if l=1;
r is an integer equal to 0, to 1 or to 2, and
s' is an integer equal to 0 or 1;
A, $A_1$, $A_2$ and $A_3$ identical or different are linear or branched alkyl radicals comprising from 1 to 8 carbon atoms and and/or substituted by a radical from a saturated, unsaturated or aromatic ring;
B is a radical chosen from the group consisting of a non-substituted ether or polyether radical comprising from 4 to 14 carbon atoms and from 1 to 5 oxygen atoms or a linear or branched alkyl radical, and/or comprising an aromatic nucleus, comprising from 1 to 9 carbon atoms;
$C_x$ is a radical chosen from the group consisting of a linear or branched monovalent alkyl radical, and/or comprising a cyclic part, wherein x indicates the number of carbon atoms and 6≤x≤25:
when the hydrophobic radical -Hy bears 1 -GpC, then 9≤x≤25,
when the hydrophobic radical -Hy bears 2 -GpC, then 9≤x≤15,
when the hydrophobic radical -Hy bears 3 -GpC, then 7≤x≤13,
when the hydrophobic radical -Hy bears 4 -GpC, then 7≤x≤11,
when the hydrophobic radical -Hy bears at least 5 -GpC, then 6≤x≤11,
G is a branched alkyl radical of 1 to 8 carbon atoms, said alkyl radical bearing one or a plurality of free carboxylic acid function(s);

R is a radical chosen from the group consisting of a linear or branched, divalent alkyl radical comprising from 1 to 12 carbon atoms, a linear or branched, divalent alkyl radical comprising from 1 to 12 carbon atoms bearing one or a plurality of functions —$CONH_2$ or a non-substituted ether or polyether radical comprising from 4 to 14 carbon atoms and from 1 to 5 oxygen atoms;
the hydrophobic radical(s) -Hy according to formula X being bound to the PLG:
via a covalent bond between a carbonyl of the hydrophobic radical -Hy and a nitrogen atom borne by the PLG thus forming an amide function obtained from the reaction of an amine function borne by the PLG and an acid function borne by the precursor -Hy' of the hydrophobic radical -Hy, and
via a covalent bond between a nitrogen atom of the hydrophobic radical -Hy and a carbonyl borne by the PLG thus forming an amide function obtained from the reaction of an amine function of the precursor -Hy' of the hydrophobic radical -Hy and an acid function borne by the PLG,
a ratio M between the number of hydrophobic radicals and the number of glutamic or aspartic units being between 0<M≤0.5;
when a plurality of hydrophobic radicals are borne by a co-polyamino acid then they are identical or different,
a degree of polymerization (DP) in glutamic or aspartic units for the PLG chains is from 5 to 250;
the free carboxylic acid functions being in the form of alkali cation salt chosen from the group consisting of $Na^+$ and $K^+$.

5. The composition according to claim 1, wherein the co-polyamino acid bearing carboxylate charges and at least one hydrophobic radical -Hy is chosen among the co-polyamino acids according to formula XXXb hereinafter:

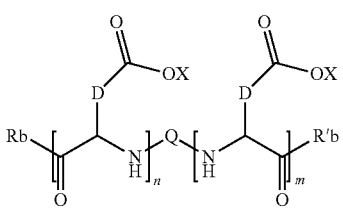

formula XXXb wherein,
D represents, independently, either a group —$CH_2$— or a group —$CH_2$—$CH_2$—,
X represents a cationic entity chosen from the group comprising alkali cations,
Rb and R'b, identical or different, are either a hydrophobic radical -Hy, or a radical chosen from the group consisting of an H, a C2 to C10 linear acyl group, a C3 to C10 branched acyl group, a benzyl, a terminal amino acid unit and a pyroglutamate,
at least one of Rb and R'b is a hydrophobic radical -Hy,
Q and Hy are as defined above,
n+m represents the degree of polymerization (DP) of the co-polyamino acid, namely the mean number of monomeric units per co-polyamino acid chain and 5≤n+m≤250.

6. The composition according to claim 1, wherein the co-polyamino acid bearing carboxylate charges and at least one hydrophobic radical -Hy is chosen among the co-polyamino acids according to formula XXXa hereinafter:

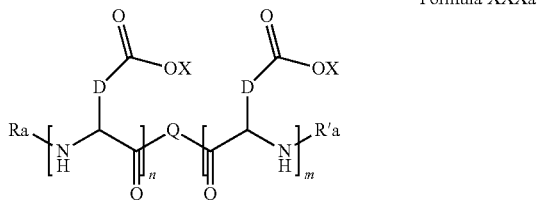

Formula XXXa wherein,
- D represents, independently, either a group —$CH_2$— or a group —$CH_2$—$CH_2$—,
- X represents a cationic entity chosen from the group comprising alkali cations,
- $R_a$ and $R'_a$, identical or different, are either a hydrophobic radical -Hy, or a radical chosen from the group consisting of a H, a C2 to C10 linear acyl group, a C3 to C10 branched acyl group, a benzyl, a terminal amino acid unit and a pyroglutamate,
  at least one of $R_a$ and $R'_a$ being a hydrophobic radical -Hy,
- Q and -Hy are as defined above,
- n+m represents the degree of polymerization (DP) of the co-polyamino acid, namely the mean number of monomeric units per co-polyamino acid chain and 5≤n+m≤250.

7. The composition according to claim 6, wherein the co-polyamino acid is chosen among the co-polyamino acids wherein the group D is a group —$CH_2$—$CH_2$—.

8. The composition according to claim 1, wherein the co-polyamino acid bearing carboxylate charges and hydrophobic radicals is chosen among the co-polyamino acids according to formula XXXb hereinafter:

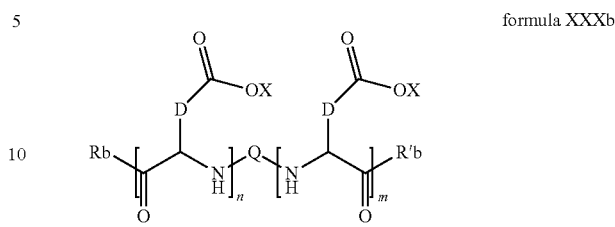

formula XXXb wherein,
- D represents, independently, either a group —$CH_2$— or a group —$CH_2$—$CH_2$—,
- X represents a cationic entity chosen from the group comprising alkali cations,
- Rb and R'b, identical or different, are either a hydrophobic radical -Hy, or a radical chosen from the group consisting of an H, a C2 to C10 linear acyl group, a C3 to C10 branched acyl group, a benzyl, a terminal amino acid unit and a pyroglutamate,
  at least one of Rb and R'b is a hydrophobic radical -Hy,
- Q and Hy are as defined above,
- n+m represents the degree of polymerization DP of the co-polyamino acid, namely the mean number of monomeric units per co-polyamino acid chain and 5≤n+m≤250.

9. The composition according to claim 8, wherein the co-polyamino acid is chosen among the co-polyamino acids wherein the group D is a group —$CH_2$—$CH_2$—.

10. The composition according to claim 1, wherein the co-polyamino acid bearing carboxylate charges and hydrophobic radicals is chosen among the co-polyamino acids according to formulas XXXa, XXXb, XXXa' or XXXb':

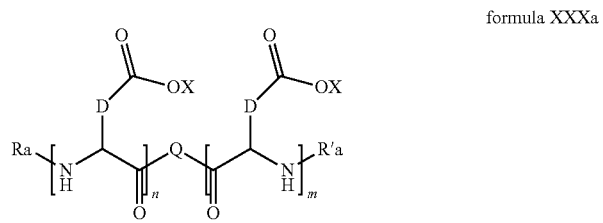

formula XXXa

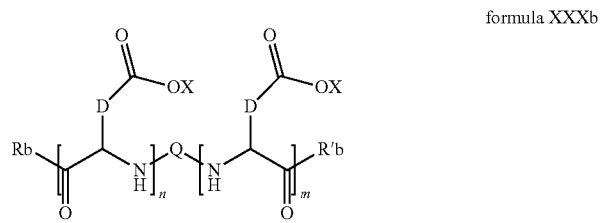

formula XXXb

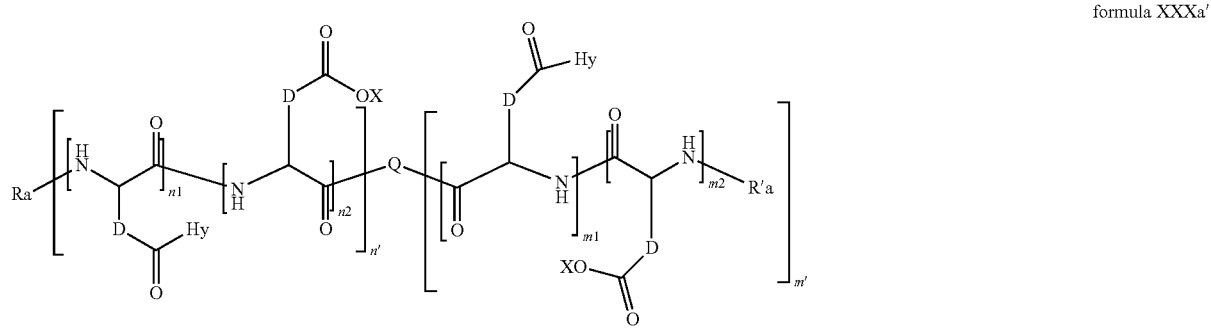

formula XXXa'

-continued

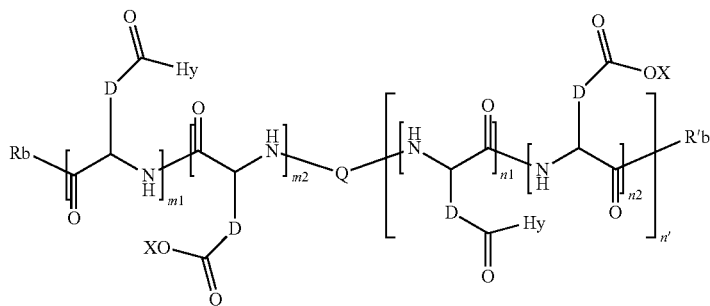

formula XXXb' wherein the co-polyamino acid is chosen among the co-polyamino acids wherein the group D is a group —CH$_2$—CH$_2$—.

11. The composition according to claim 1, wherein the concentration of co-polyamino acid bearing carboxylate charges and hydrophobic radicals is not more than 40 mg/mL.

12. The composition according to claim 1, wherein the concentration of human glucagon is from 0.25 to 5 mg/mL.

13. The composition according to claim 1, wherein the molar ratio of [hydrophobic radical]/[human glucagon] is less than 15.

14. The composition according to claim 1, wherein it further comprises a polyanionic compound.

15. The composition according to claim 1, wherein the composition further comprises a zinc salt.

16. The composition according to claim 1, wherein the composition further comprises a gut hormone.

17. The composition according to claim 16, wherein the gut hormone is selected from the group consisting of exenatide, liraglutide, lixisenatide, albiglutide and dulaglutide, the analogs thereof and the pharmaceutically acceptable salts thereof.

18. The composition according to claim 17, wherein the concentration of gut hormone is in a range from 0.01 to 10 mg/mL.

19. The composition according to claim 16, wherein the concentration of gut hormone is in a range from 0.01 to 10 mg/mL.

20. The composition according to claim 1, wherein the co-polyamino acid bearing carboxylate charges and at least one hydrophobic radical -Hy is chosen among the co-polyamino acids according to formula XXXb' hereinafter:

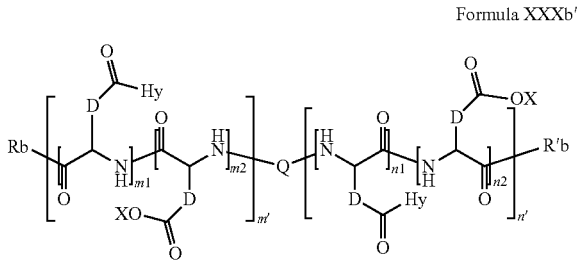

Formula XXXb' wherein:
D and X are as defined above,
Q and Hy are as defined above,
Rb and R'b, identical or different, are either a hydrophobic radical -Hy, or a radical chosen from the group consisting of an —OH, an amine group, a terminal amino acid unit and a pyroglutamate,
at least one of Rb and R'b is a hydrophobic radical -Hy,
n1+m1 represents the number of glutamic units or aspartic units of the PLG chains of the co-polyamino acid bearing a radical -Hy,
n2+m2 represents the number of glutamic units or aspartic units of the PLG chains of the co-polyamino acid not bearing a radical -Hy,
n1+n2=n' and m1+m2=m',
n'+m' represents the degree of polymerization (DP) of the co-polyamino acid, namely the mean number of monomeric units per co-polyamino acid chain and $5 \leq n'+m' \leq 250$.

21. The composition according to claim 1, wherein the co-polyamino acid bearing carboxylate charges and at least one hydrophobic radical -Hy is chosen among the co-polyamino acids according to formula XXXa' hereinafter:

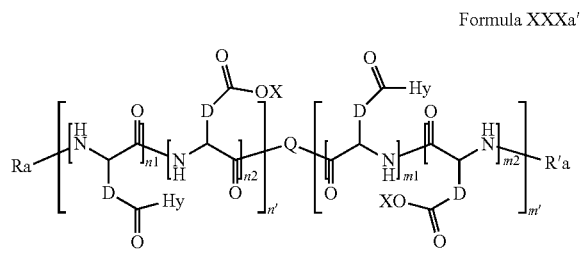

Formula XXXa' wherein:
D, X, Ra and R'a are as defined above,
Q and Hy are as defined above,
$n_1+m_1$ represents the number of glutamic units or aspartic units of the PLG chains of the co-polyamino acid bearing a radical -Hy,
$n_2+m_2$ represents the number of glutamic units or aspartic units of the PLG chains of the co-polyamino acid not bearing a radical -Hy, and
$n_1+n_2=n'$ and $m_1+m_2=m'$.

22. A co-polyamino acid bearing carboxylate charges and at least one hydrophobic radical, wherein the co-polyamino acid is chosen from among co-polyamino acids according to formula I:

[Q(PLG)$_k$][Hy]$_j$[Hy]$_{j'}$   Formula I wherein:
$j \geq 1$; $0 \leq j' \leq n'1$ and $j+j' \geq 1$ and $k \geq 2$
said co-polyamino acid according to formula I bearing carboxylate charges and at least one hydrophobic radical -Hy, the co-polyamino acid including at least two chains of glutamic or aspartic units PLG bound together by an at least divalent linear or branched radical or spacer Q[-*]$_k$ consisting of an alkyl chain comprising one or a plurality of heteroatoms chosen from the group consisting of nitrogen and oxygen atoms and/or bearing one or a plurality of heteroatoms consisting of nitrogen and oxygen radicals and/or radicals bearing one or a plurality of heteroatoms consisting of nitrogen and oxygen atoms and/or carboxyl functions, said radical or spacer Q[-*]$_k$ being bound to at least two glutamic or aspartic unit chains PLG by an amide function, said amide functions binding said radical or spacer Q[-*]$_k$ bound to said at least two chains of glutamic or aspartic units result from the reaction between an amine function and an acid function respectively borne either by the precursor Q' of the radical or spacer Q[-*]$_k$ or by a glutamic or aspartic unit, and said hydrophobic radical -Hy being bound either to a terminal amino acid unit and then j≥1, or to a carboxyl function borne by one of the chains of the glutamic or aspartic units PLG and then j'=n'1 and n'1 is the mean number of monomeric units bearing a hydrophobic radical -Hy, and wherein the at least one hydrophobic radical is according to formula X defined hereinafter:

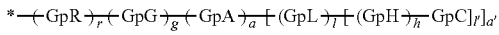

Formula X wherein

GpR is chosen from among the radicals according to formulas VII, VII' or VII":

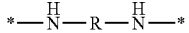

Formula VII

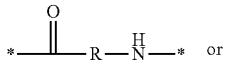

Formula VII' or

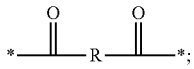

Formula VII"

GpG and GpH identical or different are chosen from among the radicals according to formulas XI or XI':

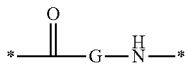

Formula XI

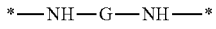

Formula XI'

GpA is chosen from among the radicals according to formula VIII:

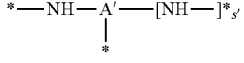

Formula VIII wherein A' is chosen from among the radicals according to VIII', VIII" or VIII"':

Formula VIII'

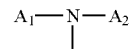

Formula VIII"

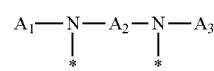

Formula VIII"'

GpL is chosen among the radicals according to formula XII:

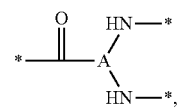

Formula XII

GpC is a radical according to formula IX:

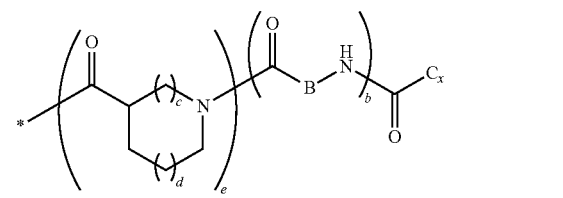

Formula IX the * indicates the binding sites of the different groups bound by amide functions;

a is an integer equal to 0 or to 1 and a'=1 if a=0 and a'=1, 2 or 3 if a=1;

a' is an integer equal to 1, to 2 or to 3;

b is an integer equal to 0 or to 1;

c is an integer equal to 0 or to 1, and if c is equal to 0 then d is equal to 1 or to 2;

d is an integer equal to 0, to 1 or to 2;

e is an integer equal to 0 or to 1;

g is an integer equal to 0, to 1, to 2, to 3 to 4 to 5 or to 6;

h is an integer equal to 0, to 1, to 2, to 3 to 4 to 5 or to 6;

l is an integer equal to 0 or 1 and l'=1 if l=0 and l'=2 if l=1;

r is an integer equal to 0, to 1 or to 2, and s' is an integer equal to 0 or 1;

A, A$_1$, A$_2$ and A$_3$ identical or different are linear or branched alkyl radicals comprising from 1 to 8 carbon atoms and and/or substituted by a radical from a saturated, unsaturated or aromatic ring;

B is a radical chosen from the group consisting of a non-substituted ether or polyether radical comprising from 4 to 14 carbon atoms and from 1 to 5 oxygen atoms or a linear or branched alkyl radical, and/or comprising an aromatic nucleus, comprising from 1 to 9 carbon atoms;

$C_x$ is a radical chosen from the group consisting of a linear or branched monovalent alkyl radical, and/or comprising a cyclic part, wherein x indicates the number of carbon atoms and $6 \leq x \leq 25$:

when the hydrophobic radical -Hy bears 1 -GpC, then $9 \leq x \leq 25$, when the hydrophobic radical -Hy bears 2 -GpC, then $9 \leq x \leq 15$, when the hydrophobic radical -Hy bears 3 -GpC, then $7 \leq x \leq 13$, when the hydrophobic radical -Hy bears 4 -GpC, then $7 \leq x \leq 11$, when the hydrophobic radical -Hy bears at least 5 -GpC, then $6 \leq x \leq 11$, G is a branched alkyl radical of 1 to 8 carbon atoms, said alkyl radical bearing one or a plurality of free carboxylic acid function(s);

R is a radical chosen from the group consisting of a linear or branched, divalent alkyl radical comprising from 1 to 12 carbon atoms, a linear or branched, divalent alkyl radical comprising from 1 to 12 carbon atoms bearing one or a plurality of functions —$CONH_2$ or a non-substituted ether or polyether radical comprising from 4 to 14 carbon atoms and from 1 to 5 oxygen atoms;

the hydrophobic radical(s) -Hy according to formula X being bound to the PLG:

via a covalent bond between a carbonyl of the hydrophobic radical -Hy and a nitrogen atom borne by the PLG thus forming an amide function obtained from the reaction of an amine function borne by the PLG and an acid function borne by the precursor -Hy' of the hydrophobic radical -Hy, and via a covalent bond between a nitrogen atom of the hydrophobic radical -Hy and a carbonyl borne by the PLG thus forming an amide function obtained from the reaction of an amine function of the precursor -Hy' of the hydrophobic radical -Hy and an acid function borne by the PLG;

a ratio M between the number of hydrophobic radicals and the number of glutamic or aspartic units being between $0 < M \leq 0.5$;

when a plurality of hydrophobic radicals are borne by a co-polyamino acid then they are identical or different;

a degree of polymerization (DP) in glutamic or aspartic units for the PLG chains is from 5 to 250;

the free carboxylic acid functions being in the form of alkali cation salt chosen from the group consisting of $Na^+$ and $K^+$.

23. A method for improving the physicochemical stability of the composition according to claim 1, by adding one or more ionic species chosen from among the group of anions, cations and zwitterions.

\* \* \* \* \*